(12) United States Patent
Kishore et al.

(10) Patent No.: US 10,028,458 B2
(45) Date of Patent: *Jul. 24, 2018

(54) YIELD TRAITS FOR MAIZE

(71) Applicant: Syngenta Participations AG, Basel (CH)

(72) Inventors: Venkata Krishna Kishore, Bangalore (IN); Andres Gutierrez-Rojas, Santiago (CL); Zhigang Guo, Research Triangle Park, NC (US); Joseph Byrum, Slater, IA (US)

(73) Assignee: Syngenta Participations AG, Basel (CH)

( * ) Notice: Subject to any disclaimer, the term of this patent is extended or adjusted under 35 U.S.C. 154(b) by 1024 days.

This patent is subject to a terminal disclaimer.

(21) Appl. No.: 14/323,005

(22) Filed: Jul. 3, 2014

(65) Prior Publication Data

US 2014/0317773 A1    Oct. 23, 2014

Related U.S. Application Data

(63) Continuation of application No. 12/536,147, filed on Aug. 5, 2009, now Pat. No. 8,809,621.

(51) Int. Cl.
| | |
|---|---|
| *A01H 1/04* | (2006.01) |
| *A01H 5/10* | (2018.01) |
| *A01H 3/00* | (2006.01) |
| *C12Q 1/6895* | (2018.01) |
| *C12N 15/82* | (2006.01) |

(52) U.S. Cl.
CPC ............... *A01H 1/04* (2013.01); *A01H 3/00* (2013.01); *A01H 5/10* (2013.01); *C12N 15/8261* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| 7,074,984 B2 | 7/2006 | Kermicle et al. |
| 7,335,828 B2 | 2/2008 | Pinnisch |
| 2011/0214200 A1 | 9/2011 | Wang et al. |

OTHER PUBLICATIONS

Stich, B. et al., "A new test for family-based association mapping with inbred lines from plant breeding programs," Theor Appl Genet, 2006, 113, p. 1121-1130.
Pritchard, J.K. et al., "Inference of population structure using multilocus genotype data," Genetics Society of America, University of Oxford, 2000, 155, p. 945-959.
Price, A.L. et al., "Principal components analysis corrects for stratification in genome-wide association studies," Nature Genetics, 2006, 38(8), p. 904-909.
Patterson, N., et al. "Population structure and eigenanalysis," PLoS Genetics, 2006, 2(12), p. 2074-2093.
Liu, K. and Muse, S.V., "PowerMarker: an integrated analysis environment for genetic marker analysis," BioInformatics, 21(9), 2005, p. 2128-2129.
Hardy, O.J. and Vekemans, X., "Spagedi: a versatile computer program to analyse spatial genetic structure at the individual or population levels," 2002, 2, p. 618-620.
Evanno, et al., "Detecting the number of clusters of individuals using the software structure: a simulation study," Molecular Ecology, 2005, 14, p. 2611-2620.
Bradbury, P.J. et al., "TASSEL: software for association mapping of complex traits in diverse samples," BioInformatics, 2007, 23(19), p. 2633-2635.
Lai et al., 2004, Genome Res., 14: 1932-1937.
Campbell et al., 2007, J. Plant Registrations, vol. 1.

*Primary Examiner* — Brent T Page
(74) *Attorney, Agent, or Firm* — Kevin Markham

(57) ABSTRACT

Methods for introgressing an allele of interest of a locus associated with a yield trait into *Zea mays* germplasm are provided. In some embodiments, the methods include providing a *Zea mays* plant that contains an allele of interest of a locus associated with a yield trait, wherein the locus associated with the yield trait is identifiable by PCR amplification of a *Zea mays* nucleic acid with a pair of oligonucleotides primers as disclosed herein, and introgressing the allele of interest into *Zea mays* germplasm that lacks the allele. Also provided are methods for identifying *Zea mays* plants that contain at least one allele associated with improved yield, improved maize plants, elite *Zea mays* plants, biomass produced from improved *Zea mays* plants, isolated and purified genetic markers, and compositions that include an amplification primer pair capable of amplifying a *Zea mays* nucleic acid to generate a *Zea mays* marker amplicon.

9 Claims, 3 Drawing Sheets

SEQUENCE LISTING

```
<160> NUMBER OF SEQ ID NOS: 173

<210> SEQ ID NO 1
<211> LENGTH: 828
<212> TYPE: DNA
<213> ORGANISM: Zea mays
<220> FEATURE:
<221> NAME/KEY: misc_feature
<222> LOCATION: (30)..(753)
<223> OTHER INFORMATION: n is a, c, g, or t
<220> FEATURE:
<221> NAME/KEY: misc_feature
<222> LOCATION: (701)..(701)
<223> OTHER INFORMATION: y is c or t

<400> SEQUENCE: 1
cccttggtgt agccggtgcg acaacattgn cgccaccacc gttgcccatg taaagtccct      60
gctggaagcc cttcaccact ccagctccac agatggcacc caggcattgc atgatnatgt     120
agaagagggc cctagtcagg gacagcttcc tggctaagaa cagcccgaaa gtcacagctg     180
ggttgatgtg tcctcctgtt gcagtagcag gtaacaacca ttagtggtgt ctttggttgt     240
tgtagttgtg ttcttggtct atgcttgctg aattgcatgg attctttcac agttcgangc     300
tttgaaatta agcatgtatc tggagtcaat tacacaaacc atgaccagga aagtactatg     360
caaattaacc atatgtcgga ccactactgt ttttgagatg gaatgaccac tgtaggttaa     420
ctgatatagt tttctatgta cacacctcac aagttaaaat ggtgccttt gtactttaat      480 ctttaatttt ttacacacaa ctgtggcccn aagtgctnga catgaactac tagcntgttt     540
ggtttgagga atgagctagt ccatcatatt ctcactcctc actttttttg tttggtttgt     600
ggaatagaat gagttgatct atcatcacct cattccttat agttagttag ttagtactaa     660
```

```
tatgaggaat ggggtcatcc caccaaattt gaggaatgga yccatgatgc accaccatat    720
tttggatgga ntgattcctc aaaccaaaca ccncctacat ctggcagttg atgatgcctt    780
tgcataatta cacgcagcac atgctatagt agtacagtat gttacatg                828
```

<210> SEQ ID NO 2
<211> LENGTH: 22
<212> TYPE: DNA
<213> ORGANISM: Zea mays

<400> SEQUENCE: 2

```
gggtcatccc accaaatttg ag                                            22
```

<210> SEQ ID NO 3
<211> LENGTH: 23
<212> TYPE: DNA
<213> ORGANISM: Zea mays

<400> SEQUENCE: 3

```
gcatcatcaa ctgccagatg tag                                           23
```

<210> SEQ ID NO 4
<211> LENGTH: 743
<212> TYPE: DNA
<213> ORGANISM: Zea mays
<220> FEATURE:
<221> NAME/KEY: misc_feature
<222> LOCATION: (18)..(729)
<223> OTHER INFORMATION: n is a, c, g, or t
<220> FEATURE:
<221> NAME/KEY: misc_feature
<222> LOCATION: (498)..(498)
<223> OTHER INFORMATION: y is c or t

<400> SEQUENCE: 4

```
caaattaaag atcagctnnn ncaagttaat tancacggca cacatatanc attacattct    60
tattcagaga tactcncaca cannnnnaca cnncagacaa ctgaaaatac annncngact    120
cacacggtca aaatacaacg cnaggttcnc tcactnnnnn nnngacactt gaanncacac    180
ncncncacnc nnattcactc tgaactggtc attattctag ntgnaaatca acacggagat    240
ggagcgngca nnnannnann nngnnnannn ncatgaccgc taaggnncag gnagaccagt    300
aagtaacgat cgattgcccn ctcctccnaa cacatagaat gatttagatg gagagaggga    360
gacctggaag aaaggcttag ccttcccttg ccgataagac ttgccttctt tcttgtgcac    420 cgccaagca tccntgctca cacgccacca gcccgcggcg ccgaagctcc nggcggacgg     480
catggcaagc atgcttcytc gctgcatgca ctcacaccgc cnatgatggc ggtgngacga    540
ccagnnnnnc ttcgctcaca gcaccttctt cttctttgcc cctcttnttc ctcttcctcg    600
acatcatacg atgnaannnn nntgtgcttc acagntcgg tgtgagtggg ncnnnnacac     660
tngtnnggcc ttagcttggc caatnttcct ttcttttata ggcatcttct cgtcaactga    720
atcacgcang tctgtgcgag cga                                           743
```

<210> SEQ ID NO 5
<211> LENGTH: 16
<212> TYPE: DNA
<213> ORGANISM: Zea mays

<400> SEQUENCE: 5

```
gacggcatgg caagca                                                   16
```

```
<210> SEQ ID NO 6
<211> LENGTH: 24
<212> TYPE: DNA
<213> ORGANISM: Zea mays

<400> SEQUENCE: 6
tcgtatgatg tcgaggaaga ggaa                                            24

<210> SEQ ID NO 7
<211> LENGTH: 743
<212> TYPE: DNA
<213> ORGANISM: Zea mays
<220> FEATURE:
<221> NAME/KEY: misc_feature
<222> LOCATION: (18)..729
<223> OTHER INFORMATION: n is a, c, g, or t
<220> FEATURE:
<221> NAME/KEY: misc_feature
<222> LOCATION: (587)..(587)
<223> OTHER INFORMATION: y is c or t

<400> SEQUENCE: 7
caaattaaag atcagctnnn ncaagttaat tancacggca cacatatanc attacattct       60
tattcagaga tactcncaca cannnnnaca cnncagacaa ctgaaaatac annncngact      120
cacacggtca aaatacaacg cnaggttcnc tcactnnnnn nnngacactt gaanncacac      180
ncncncacnc nnattcactc tgaactggtc attattctag ntgnaaatca acacggagat      240
ggagcgngca nnnannnann nngnnnannn ncatgaccgc taaggnncag gnagaccagt      300
aagtaacgat cgattgcccn ctcctccnaa cacatagaat gatttagatg gagagaggga      360
gacctggaag aaaggcttag ccttcccttg ccgataagac ttgccttctt tcttgtgcac      420
cgccgaagca tccntgctca cacgccacca gcccgcggcg ccgaagctcc nggcggacgg      480
catggcaagc atgcttcntc gctgcatgca ctcacaccgc cnatgatggc ggtgngacga      540
ccagnnnnnc ttcgctcaca gcaccttctt cttctttgcc cctcttyttc ctcttcctcg      600
acatcatacg atgnaannnn nntgtgcttc acgagntcgg tgtgagtggg ncnnnnacac      660
tngtnnggcc ttagcttggc caatnttcct ttcttttata ggcatcttct cgtcaactga      720
atcacgcang tctgtgcgag cga                                             743

<210> SEQ ID NO 8
<211> LENGTH: 24
<212> TYPE: DNA
<213> ORGANISM: Zea mays

<400> SEQUENCE: 8
ctcacagcac cttcttcttc tttg                                            24

<210> SEQ ID NO 9
<211> LENGTH: 28
<212> TYPE: DNA
<213> ORGANISM: Zea mays

<400> SEQUENCE: 9
gacgagaaga tgcctataaa agaaagga                                        28

<210> SEQ ID NO 10
<211> LENGTH: 832
<212> TYPE: DNA
<213> ORGANISM: Zea mays
<220> FEATURE:
<221> NAME/KEY: misc_feature
```

```
<222> LOCATION: (8)..(801)
<223> OTHER INFORMATION: n is a, c, g, or t
<220> FEATURE:
<221> NAME/KEY: misc_feature
<222> LOCATION: (708)..(708)
<223> OTHER INFORMATION: r is a or g

<400> SEQUENCE: 10
ataatttnat ggaaagaagc atgtacttac ttganttggg atattgtcag tttgtcacct      60
taatttattg agttaataca tcactataag accataaaca ggaccccaaa tntgcacact     120
tctaatccag catatgcnnn nnnnattatt ttataaanat gataatgatt tgntcnacca     180
gccatggttt cacgaatnac tgttgagtca gtaatgtgtt ttaagtgcaa aacttttaac     240
tgcaaaagcc nctcacaatt ttttnnnntn aanttnnant tnnnattttt ttnannnaaa     300
ctgattctgt acttctagtt ggaaacttag aatgcangac tgctaaagcn actcctaatt     360
ggaatgcatg acatttngta tngtttanga tttnatttcc tttgaaanat ttgganagaa     420 atttntatt anaagtttga gggnacatag atattgtgtc aaatgntttt ttgtgaatag      480
ttnaaaaaag acagacccag tgttggagac tcatacatgn gtgggctcnn ggaangggat     540
aaaccaagnn aaggcaagcc tttctntgta aatgcgngga ggctgcttcg aatccacgac     600
ctggtgactc antgaggcgg ctctccncac tgcaccagcc ctgcccttnt ttctgttgaa     660
tagctgattg aaaaaannct ggaaatncat tctgctgtaa catattcrga atgataccat     720
gaggatttnt tctgctgtgt ttcttgttct ttggcatgnt tggtagggng ngnaccttgt     780
aacatgatat tctaaataac ntgcagatga tagttaacag atcacgagct aa             832

<210> SEQ ID NO 11
<211> LENGTH: 16
<212> TYPE: DNA
<213> ORGANISM: Zea mays

<400> SEQUENCE: 11
caccagccct gccctt                                                     16

<210> SEQ ID NO 12
<211> LENGTH: 25
<212> TYPE: DNA
<213> ORGANISM: Zea mays

<400> SEQUENCE: 12
ccaaagaaca agaaacacag cagaa                                           25

<210> SEQ ID NO 13
<211> LENGTH: 878
<212> TYPE: DNA
<213> ORGANISM: Zea mays
<220> FEATURE:
<221> NAME/KEY: misc_feature
<222> LOCATION: (409)..(618)
<223> OTHER INFORMATION: n is a, c, g, or t
<220> FEATURE:
<221> NAME/KEY: misc_feature
<222> LOCATION: (140)..(140)
<223> OTHER INFORMATION: the t at this position can be absent

<400> SEQUENCE: 13
ctgctgcctt tggtactaag gctgttgcag ttggtgccga tatctcactt gatactgcaa      60
ctgggaactt gactaaatac aatgctgcac tgaggttcac tcatgaagac cttgtcgcat     120
ccctgaacct gtgagttttt caaagtgtag taatcctata tacttaggca ctgtatgcga     180
```

```
ctgttatttg gcagcacttg taatatcatt atttatggtt aagtacaaat ccctgcttga    240
tgtgtctcaa cttaaagctg ttgtgtaagt ggtttagtgc ataaaagtta gtcaaaatgt    300
taatatattg gtcaccgtga tttcacctttt tctcagacat ttctcaaatt gagttttgaa   360
agaagaaact ttacaatttg actttactta gatcgtttgc aacaaactnn nnnnnnnnnn    420
ncagattatt gcatgtacag aaattgatcg aagtaactga ctttgctaag tgttttttnn    480
gtttcattga gaaaatgat ctattgcatt aagctggtag caatatggct aatattgagc     540
cgtacctcca ggaagggtct gatatgctca gtattttggt tttctaattg agtgaaaagt    600
cctatgtata atcttnnnat attaaatgaa attgatgtca tagcttttca acagatgtaa    660
ccctgtttct tttaggacgt ttactgtctt attttttgc agtgcctgcc aaatttcatg     720
taactgaccc aaccttctct tgcaggaaca acaagggaga cagccttact ggagcctact    780
atcacaaggt gagcgaattg accaacacag ctgttggggc agagcttacc cacagcttct    840
cgaccaatga aaacaccctc acctttggcg ggcagcac                            878

<210> SEQ ID NO 14
<211> LENGTH: 21
<212> TYPE: DNA
<213> ORGANISM: Zea mays

<400> SEQUENCE: 14
tgctgcactg aggttcactc a                                              21

<210> SEQ ID NO 15
<211> LENGTH: 25
<212> TYPE: DNA
<213> ORGANISM: Zea mays

<400> SEQUENCE: 15
ttacaagtgc tgccaaataa cagtc                                          25

<210> SEQ ID NO 16
<211> LENGTH: 660
<212> TYPE: DNA
<213> ORGANISM: Zea mays
<220> FEATURE:
<221> NAME/KEY: misc_feature
<222> LOCATION: (452)..(533)
<223> OTHER INFORMATION: n is a, c, g, or t
<220> FEATURE:
<221> NAME/KEY: misc_feature
<222> LOCATION: (116)..(116)
<223> OTHER INFORMATION: r is a or g

<400> SEQUENCE: 16
tacagttgca agaggtgtgg gacaaccact tgttatttct cagtgacgaa ggactgtgac     60
agttaaaaaa ataaaaaata aaaacgcatg aaagaatgag ccacccggtg agccaraaac    120
tctacaaaat tgccgccgca cgaagtacag tcgctttacg gcttctgaat cagtcgttgt    180
gttttcagtt gcgtcacagc gggtgcttct tccatctcac caaggaattg aggaacccca    240
tcacctgtgt gacagacaag cagacacaca gattagagtc accagactag accgaacgaa    300
gccgacaggg tagaagcaag trctgaagga aaaaaaaga ccmcragagg tttacttcag    360
acgggtctct cagcgagtag aaggcttcag tgtccttggg cacctgcgag actaggattc    420
cgtatccaca gyttcgctct cgcagtrcct gngagcgagc gagagagaga gagagagaga    480
gagngnnnca acaggagatt ctgatgagtc tagaacnggc tcnaaacnat gcngagtgtg    540
agatgcacaa gtttcctgag aagatgtagc aaccttgaag gcgtcttcgt ctgttcgatc    600
```

```
gtctccgatg tagataggaa ccacatcttc ggagtcgctt aggccgagcg accgaagcag      660
```

<210> SEQ ID NO 17
<211> LENGTH: 21
<212> TYPE: DNA
<213> ORGANISM: Zea mays

<400> SEQUENCE: 17

```
acgcatgaaa gaatgagcca c                                                21
```

<210> SEQ ID NO 18
<211> LENGTH: 21
<212> TYPE: DNA
<213> ORGANISM: Zea mays

<400> SEQUENCE: 18

```
cagaagccgt aaagcgactg t                                                21
```

<210> SEQ ID NO 19
<211> LENGTH: 1363
<212> TYPE: DNA
<213> ORGANISM: Zea mays
<220> FEATURE:
<221> NAME/KEY: misc_feature
<222> LOCATION: (194)..(1322)
<223> OTHER INFORMATION: n is a, c, g, or t
<220> FEATURE:
<221> NAME/KEY: misc_feature
<222> LOCATION: (269)..(269)
<223> OTHER INFORMATION: r is a or g

<400> SEQUENCE: 19

```
cttccttgag ccttcctcgc tgaatcttgt tgaacagctc tccacccttta acatgttcca     60 gcacaaagta tattttggtt ttggtggcca tgacctcata gagctgtacg atgtttggat     120
gcctaacaag cttcatcaca gaaatttctc gctggatttg atcaatgaga ccaaccttca     180
taaccttctc cttntcaatc actttgatcg cgacactttc ngaagtcgcc gtgttacgag     240
catggtaaac cttggcaaag gtgccttgrc caagcaattt ccccatctca tacttgtgca     300
agagaacgtt ccctttatgc tctgccatct gtgcctgtgt atgctacgta tggtggnnnn     360
nnnatgcaca cagaggtcac ttgcttatcc ttgacagtna nanaaaannn gagacagcaa     420
agaggtcgag agggtgtgaa gacttcaacc gtctccaccg agatggtgat ctaagaagac     480
ggttgagccg ccacgtcgaa ccccattgtg cgaaagcacg aggtggagat acgtgtactc     540
ttgagcttcg aagtcatcaa gagnnggcan agaatgaaga gtatgcgtg ctttcctgcc      600 aagtccctca caaagtagct cttcgacgtg caagcacatc tttctgcatt ccctaaggcg     660
ttttctgctc cttactgaaa acccaatact gccgaagatg taaaaagaga aaggcatcag     720
ttataagatc aatacaacac atatatatct atctgtatat aaaaatataa ctgttagtat     780
gagagggaaa aaatcaagga taatgaaaaa ttggaagaag aaaacaaagg agcagatatt     840
tcttgcacga acatgtgtgc gcaagttagt tcagacaatc gttacgggga gtttggctaa     900
tctgattttt agacataagt agcaaaaacta aaaaaaatct acttttataac cagatccaac     960 agggttgttg acaccttctt acccgattta acaggttgg tgacaccttt tccccaaat     1020 taaacatgtt ggtggcttta ccataacccg aaaacggcct tgataattct tttgttctaa    1080
aaaaactttg ttgggacccc ncaaaaaaaa caaaaaccac ctgaacctct tgggaggggt    1140
tttttattgg tttttataacc cagagaaaaa aaaggggga aaggaaaccc ttcgcctccc    1200
```

```
catgaatata aattcgcggc atttaataa aaaagggccc gagggggggc gttaaatgaa      1260
agaaaatttt tctgtggaac aacacccttg gggggggccc tttaatttct ctccacccc      1320 cnaccggcac cggggggaaa ggatccccc tctcgatata ggc                        1363
```

<210> SEQ ID NO 20
<211> LENGTH: 23
<212> TYPE: DNA
<213> ORGANISM: Zea mays

<400> SEQUENCE: 20

```
gagcatggta aaccttggca aag                                              23
```

<210> SEQ ID NO 21
<211> LENGTH: 25
<212> TYPE: DNA
<213> ORGANISM: Zea mays

<400> SEQUENCE: 21

```
gaacgttctc ttgcacaagt atgag                                            25
```

<210> SEQ ID NO 22
<211> LENGTH: 1635
<212> TYPE: DNA
<213> ORGANISM: Zea mays
<220> FEATURE:
<221> NAME/KEY: misc_feature
<222> LOCATION: (403)..(1633)
<223> OTHER INFORMATION: n is a, c, g, or t
<220> FEATURE:
<221> NAME/KEY: misc_feature
<222> LOCATION: (280)..(280)
<223> OTHER INFORMATION: y is c or t

<400> SEQUENCE: 22

```
cacctccttc tccgtcttgc gccccttctt ggacttgtag tacacgctca tgaacgtgcc      60
caccgccccg tactttggc ggcagtgctc gtagtgcgac gcgtcgaaca tgcgccagaa      120
gtccttctcg ttcagctccg acaccgcgta ctgcggctgg tagctgtggt tctcgatcag     180
ccactgctcc agcctgtgca cagcctccgc gccgttgaac tcctccccc tcagcaccgc     240 cccgggggcg tagtacacgc ccacgtccgt gaacatctgy gcgtagctcg tgtcgccctg     300
cctgtgctgg tgctcgaacc caggctccgg gtacaccatc gtcttcaccg gcagcttgta     360
cagccggtga gggcacagcc acagaggata cacctaccaa aangaatttc aattattatt     420
agtatatcca gtcaactact cataaagcaa gcngcaccag caccagcacc agccanccat     480
tgtacctcca tctcgcggtg cacgaactcc agcgcntccc caaccttgta cagcggcacc     540 agcatnnct ggatcacatg gttgtcgngg tagtagttcc tgatagcctc gccctgggtc     600
gccttcagca gggacacctt cggtggcatc agccagccca gcaggaacct gaaccagaac     660
tggtcgccga agggcaggat cagcttcccc tcccagtaca ggcaccgggt gtgccggtgg     720
tagnannccc tcgtcgggat gtactccaca aactcgcccc tcttcangcg ccgtctgagc     780
gtgctggtag aaccagggct taaaccacca ccccacgcag ttgatcttgt tgcccttctt     840
cttcgcctct tctttngnag cgtacacgcc cgtcatcatg acaccctcgc tctctgtgta     900
caccatccct tcaacaaagt cagggacctt tgccgggtca ccgtccctcg gngcgaaaga     960
atccgcgtag gcctgcgcga tctccttag nccccccttg actggagtgt aggtgagctt    1020
catgtactcn tnnnngggga tcagcttgat ctcngcagag acaaggaacc ccagtgttcc    1080
ctgggaccag ggaatnccat agaaaaggtc agagtactcg ttgtccttgg tggctctnac    1140
```

```
gacccggcca tctgcgagaa caacctccat cgcgacaacc gtgtcngaga aaaggccata    1200
gaggtgagag ctcccctcga tgccgtaacc gttgatcagc ccaccaacag tgaggtcgtc    1260
gagctcggcg acgaccgcaa gggcaaggtt cattgggcag gtagctctgg ttatctgacc    1320
catgttgaca aggggctcga ccttggcaac catcctctct tgtcnatct caaggatgtt     1380 cctgaaggaa gaaaggtcga cctcgaaatg cctcgcacgc ttgtagtcca cgttgcgcat    1440
gccaacagcg atccagggct tcctggccgt gcaaacaaga ccgtccttct tcgggttcct    1500
ctgcttgagc cgcttcacga ccttctgcac gttctcgtng tgctgctttnt ggcgcttctt   1560 ctccgacttc anggcggacc acatgtcgcc caggaagatg ttgaagtaga tcagagttaa    1620
nntaggaagg acnac                                                     1635
```

<210> SEQ ID NO 23
<211> LENGTH: 16
<212> TYPE: DNA
<213> ORGANISM: Zea mays

<400> SEQUENCE: 23

```
cgcccacgtc cgtgaa                                                      16
```

<210> SEQ ID NO 24
<211> LENGTH: 15
<212> TYPE: DNA
<213> ORGANISM: Zea mays

<400> SEQUENCE: 24

```
aggcagggcg acacg                                                       15
```

<210> SEQ ID NO 25
<211> LENGTH: 874
<212> TYPE: DNA
<213> ORGANISM: Zea mays
<220> FEATURE:
<221> NAME/KEY: misc_feature
<222> LOCATION: (11)..(863)
<223> OTHER INFORMATION: n is a, c, g, or t
<220> FEATURE:
<221> NAME/KEY: misc_feature
<222> LOCATION: (374)..(374)
<223> OTHER INFORMATION: k is g or t

<400> SEQUENCE: 25

```
tctgttcatc nnntgttcaa ttaattgagt gatcacagag gccancagct ggtgcgctaa      60
aanaactcag tggaagagga tgcacgtcct atgaaaaatt aacagaaatg cattaagcta     120
gnttcaccan tcttgttgcg cctagatttt tttnagataa aaaantgatc aaagtggtga    180
nttccgttat tgatattngc gtagccatgc agcctgaatt ttcaactaaa ctaggtggcc    240
gtggaattat ccaacaacta tttggcagcc ctgtccaaaa tcntgatncc ncgagcataa    300
cttaattcac aacgtgntgc ttatgtatgc tggcgcgctt accgatggtg gggatggtgg    360
tgacgatctc gcckagcttn agcttgtaga ggatggtggt ctttccggcg cgtcgagtc     420 ccaccatcag gatccgcatc tccttcttgg cgaacagccg gctgaacagc ttggtgaacg    480
tnagccccat ntnttccctc tcncctgcag cagacacgaa acccaggtca tcaggacgcc    540
gatcnatccc acgcatgtcc ctcacacggc cacaggncgc tagatntacg cgtcgcagcg    600
cccagatcca cctagggncc gaacngaagg ccggcggta cgagatccgc aggaaatggn     660
gagcggatnn naccggcacn gcagcccaga gcgcgcgaac ggtcggcgag agcgttctac    720
```

```
ctnaggatag atcccgtgcg cggggnggagc gatcctccgt ggnggannnn nngnnnnggg      780
annggnagcg gggtaggcgn gnnnnnaggg cgctggttct caccttgtcg gcggatccga      840
ttcgcggtgt cgggctcgcc ggngacgcag ccgg                                  874
```

<210> SEQ ID NO 26
<211> LENGTH: 15
<212> TYPE: DNA
<213> ORGANISM: Zea mays
<400> SEQUENCE: 26

```
gctggcgcgc ttacc                                                        15
```

<210> SEQ ID NO 27
<211> LENGTH: 22
<212> TYPE: DNA
<213> ORGANISM: Zea mays
<400> SEQUENCE: 27

```
agaccaccat cctctacaag ct                                                22
```

<210> SEQ ID NO 28
<211> LENGTH: 526
<212> TYPE: DNA
<213> ORGANISM: Zea mays
<220> FEATURE:
<221> NAME/KEY: misc_feature
<222> LOCATION: (20)..(519)
<223> OTHER INFORMATION: n is a, c, g, or t
<220> FEATURE:
<221> NAME/KEY: misc_feature
<222> LOCATION: (236)..(236)
<223> OTHER INFORMATION: r is a or g
<400> SEQUENCE: 28

```
ggcacactaa cccactgccn agcacctcgt ctgatctgat ctgatgctga tgcnnnnnna       60
gggttggcgg ttccgggatg gacgtcagga gcaaagccag ggtcagtagt agtacacgct      120
tttgttcacc ttcaatctta tccttatctt ggnagtgtaa annttttttg tacttttgtt      180
ggaagataga tagatagata tatgtgcctt tgcaagtgtg tcnctttttca tgggcrtctt      240 cttcacacga agaaaaatgt caaagtgcat gacatctcac cctgcctttt ttttgggagg      300
gtactcanac gctgtccgga cctgttgatg accccagcaa gcttccgaag tggaacttcg      360
acggctccag caccggccaa gctccgggcg acgacagcga agtcatcctt tggtacccgc      420
nnnctttctc tcnagtccac tctccnnnng tnttcncnca ccttgacgtg tgtgcctcac      480
tncccttgct aatgccacgt tgcgctgatt cacnntgant cttccgg                    526
```

<210> SEQ ID NO 29
<211> LENGTH: 26
<212> TYPE: DNA
<213> ORGANISM: Zea mays
<400> SEQUENCE: 29

```
agatatatgt gcctttgcaa gtgtgt                                            26
```

<210> SEQ ID NO 30
<211> LENGTH: 23
<212> TYPE: DNA
<213> ORGANISM: Zea mays
<400> SEQUENCE: 30

```
gggtgagatg tcatgcactt tga                                               23
```

```
<210> SEQ ID NO 31
<211> LENGTH: 765
<212> TYPE: DNA
<213> ORGANISM: Zea mays
<220> FEATURE:
<221> NAME/KEY: misc_feature
<222> LOCATION: (1)..(765)
<223> OTHER INFORMATION: b is c, g, or t
<220> FEATURE:
<221> NAME/KEY: misc_feature
<222> LOCATION: (1)..(765)
<223> OTHER INFORMATION: k is g or t
<220> FEATURE:
<221> NAME/KEY: misc_feature
<222> LOCATION: (1)..(765)
<223> OTHER INFORMATION: m is a or c
<220> FEATURE:
<221> NAME/KEY: misc_feature
<222> LOCATION: (1)..(765)
<223> OTHER INFORMATION: r is a or g
<220> FEATURE:
<221> NAME/KEY: misc_feature
<222> LOCATION: (1)..(765)
<223> OTHER INFORMATION: s is c or g
<220> FEATURE:
<221> NAME/KEY: misc_feature
<222> LOCATION: (1)..(765)
<223> OTHER INFORMATION: w is a or t
<220> FEATURE:
<221> NAME/KEY: misc_feature
<222> LOCATION: (1)..(765)
<223> OTHER INFORMATION: y is c or t

<400> SEQUENCE: 31
cmagtggttc catcgaytat ggagagttcc tagcygcaac tttacatctg aacaaagtcg      60
agcgagaaga caacctcttc gcagcattct catactttga taaagacggc agcggttata     120
ttactcayga tgagctacaa aaagcatgyg aggaattygg tatagaagat gcacacctag     180
aagatatcat ccatgacgtt gatcaggaca atgtaagtag atttgcatct yatcaygcts     240 tgtgttttaaa tctaaaggcc aagagttgca tctyacttgg ttatcaatcc aggatggtcg    300
gatcgactac aacgagtttg taacaatgat gcagaaggga ataacccac tagggaaaaa     360 ggggcactgc cagatgagct ttggtcttag agaagcattg aagcttggct aastggtaac    420
tggtgttttc cctytgcact tctttccttt tgttcgctt agcaatccag taatycacat      480
gaattcttgt gtttctggtt cctgttccat bgattrtgct ctatggcayg tgctsaatmc    540
aatatacgct atatgcttac tgtttggttg cttttcgcag gcatgatcaa tcctgtgtga     600
agtgycattc ggcttcatat gccaacttta gctgatgaaa ctaagtccgt gaatttggga    660
cgccggtacc aaaggtggag caagtgcgcg rtacgattag cttygggata ccaactaagc    720
agtkagcatg caggaacaca ttggtgatct ttcgtcgtwa mccccc                   765

<210> SEQ ID NO 32
<211> LENGTH: 21
<212> TYPE: DNA
<213> ORGANISM: Zea mays

<400> SEQUENCE: 32
ttcgcaggca tgatcaatcc t                                               21

<210> SEQ ID NO 33
<211> LENGTH: 26
<212> TYPE: DNA
<213> ORGANISM: Zea mays
```

```
<400> SEQUENCE: 33
cccaaattca cggacttagt ttcatc                                          26

<210> SEQ ID NO 34
<211> LENGTH: 825
<212> TYPE: DNA
<213> ORGANISM: Zea mays
<220> FEATURE:
<221> NAME/KEY: misc_feature
<222> LOCATION: (9)..(811)
<223> OTHER INFORMATION: n is a, c, g, or t
<220> FEATURE:
<221> NAME/KEY: misc_feature
<222> LOCATION: (349)..(351)
<223> OTHER INFORMATION: the cga trinucleotide can be absent

<400> SEQUENCE: 34
ggctcgggnc caagccgtac gggctcaact cggaggcgnt cgcgtgacag cgccgtcgtc      60
atcatgaccc atgccaacct cgtcgaaatn ctcatggacg tggtatgnnn nnnnnnnnn     120 natnnatgnn ncanncannt acatttgatc gatcagcagc tgattatgnt tgctggcttc    180 tnaacttta attcgatttt cttntgcnca gaancagtat gcggccgtgt tctcgagtat     240
ngtgtcgaga gccgcgacgc tggaggtgnt atcaaccggc gtggctggga actacaatgg    300
tgcattgcaa gtggtgcgtg cnnnnntgca tgttctgaaa tttgatgacg atgcatnnnn    360
nnnngcatnn nnngcnnnnn gnnagcnnnn cgtttgatgn natctgctg  tncattnnnn    420 ctgcagatgt cggtggagtt tcaggtgcct tccccactgg tgccgaccag ggaaagctac    480
ttcgtgaggt nctgcaagca gaacgccgac ggaacatggg ccgtcgtcga cgtctcgctg    540
gacggcctgc gccccggcgc agtcctcaag tgccggcgcc ggccntcggg atgcctgatc    600
caggaaatgc ccaaggcta ctcnaaggtg acctgggtgg agcacgtcga ggtggacgac     660
aggtcggtgc ncagcatcta caagctgctg gtgagctcgg ggctggcntt cggtgcacgc    720
cgatgggttg ggacgctgga ncgccagtgc gagcgccttg ccagtgtcat ggcnncagca    780
acatcccgac cagngacatc ggtggtgaga nttctgagac ctgca                    825

<210> SEQ ID NO 35
<211> LENGTH: 18
<212> TYPE: DNA
<213> ORGANISM: Zea mays

<400> SEQUENCE: 35
gcattgcaag tggtgcgt                                                   18

<210> SEQ ID NO 36
<211> LENGTH: 22
<212> TYPE: DNA
<213> ORGANISM: Zea mays

<400> SEQUENCE: 36
cctgaaactc caccgacatc tg                                              22

<210> SEQ ID NO 37
<211> LENGTH: 800
<212> TYPE: DNA
<213> ORGANISM: Zea mays
<220> FEATURE:
<221> NAME/KEY: misc_feature
<222> LOCATION: (18)..(788)
<223> OTHER INFORMATION: n is a, c, g, or t
<220> FEATURE:
<221> NAME/KEY: misc_feature
```

<222> LOCATION: (389)..(389)
<223> OTHER INFORMATION: r is a or g

<400> SEQUENCE: 37

```
tgcatcgcag cccaatantg aaacagntaa aaatacatta ancagtanag agttgtanca      60
agagagaaca gaacttactt cctgagcntg agctggggtg gcgactttgc cagttccaat     120
agcccagact ggttcatagg caagaacaac gttgctccag tccttgatct tctctgtaaa     180
acaaacagcc atttgatcca ttnagcctga tttttcgtat agggtcaaaa aanncttggt     240
aacttcaaan caaggcacta aatgttcaca tgaacaaaac aaagggcaga cccagctccc     300
acatgaatgt ggggtctttc ccccacaaat gnggaaagga aaatccagca tgtaaattca     360
tccaagcaac anaaacaaaa actcggccrg ggaaggaaan acnncctcc cggtattcta      420
ttaagaagag accgaaacat ggtcccgncc gaaaaaatcc ccnaaccta gcccccatc       480
actagttggc cgncatcgcn nactctncaa atgcccancc ggagggtggg gnngcatgac     540
ntaacncgag ngcgggcngg ncacaacgan nggatttttt aaccaagccn gaaattngcc     600
cncaaggggg atcgaanccg ggacctngag gtgctanttg gaagcnttaa ccattacgct     660
anaggcccctt tcgcagcgac agaaacacac ataagttgat tcctaaacta aagcngttac    720
agaaaaacag taatgtccga actccggata tgtagattat ctaacagaac tgatcaccag     780
aagcaaanngg cctgttcagt                                                800
```

<210> SEQ ID NO 38
<211> LENGTH: 25
<212> TYPE: DNA
<213> ORGANISM: Zea mays

<400> SEQUENCE: 38

```
ccagcatgta aattcatcca agcaa                                            25
```

<210> SEQ ID NO 39
<211> LENGTH: 25
<212> TYPE: DNA
<213> ORGANISM: Zea mays

<400> SEQUENCE: 39

```
ggaccatgtt tcggtctctt cttaa                                            25
```

<210> SEQ ID NO 40
<211> LENGTH: 556
<212> TYPE: DNA
<213> ORGANISM: Zea mays
<220> FEATURE:
<221> NAME/KEY: misc_feature
<222> LOCATION: (48)..(531)
<223> OTHER INFORMATION: n is a, c, g, or t
<220> FEATURE:
<221> NAME/KEY: misc_feature
<222> LOCATION: (76)..(76)
<223> OTHER INFORMATION: r is a or g

<400> SEQUENCE: 40

```
gtgacaagcc caagagtttg ggttccacgg acaagatcaa aaccatangc agtcacactg      60
ctcagrgatg ttagggtcct gcattcaaaa gnacagcaag tatgatgtca tcacaaaagg     120
gtctaggagg ancaatggct gagaaaaggg tgagctancn acataaataa catacttgta     180
ggactcagca ggaacatcag caaagtaagt ctcaacaagc acattcaatc cagaaagtac     240
agattcaagt tctgcntatg cagcagagaa tgcagccaat ttgtcagaat caaggtcgag     300
```

```
gacaagagtg ggctcatcaa actgaatcca tgaagcccca gctgccttca actcagcant    360
gacctcccta caatcatcaa ncatcaaatt atcaactgaa gattcnaggg ccagagcagc    420
caataacttc tttataatct tacttgtaga ctggnaggat gctgctaaga agggnaaaga    480
agagggaatc ccttctccac acccttggcn ggctttgaga gcaacaggta ngagactggt    540
ccaacaagta ctggca                                                   556
```

<210> SEQ ID NO 41
<211> LENGTH: 25
<212> TYPE: DNA
<213> ORGANISM: Zea mays

<400> SEQUENCE: 41

```
ttccacggac aagatcaaaa ccata                                         25
```

<210> SEQ ID NO 42
<211> LENGTH: 25
<212> TYPE: DNA
<213> ORGANISM: Zea mays

<400> SEQUENCE: 42

```
ctcctagacc cttttgtgat gacat                                         25
```

<210> SEQ ID NO 43
<211> LENGTH: 506
<212> TYPE: DNA
<213> ORGANISM: Zea mays
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: m is a or c
<220> FEATURE:
<221> NAME/KEY: misc_feature
<222> LOCATION: (10)..(10)
<223> OTHER INFORMATION: r is a or g
<220> FEATURE:
<221> NAME/KEY: misc_feature
<222> LOCATION: (279)..(279)
<223> OTHER INFORMATION: y is c or t

<400> SEQUENCE: 43

```
cccagtnamr acgtaattga ggaaagggag caagccattc aagatatcca acagcagatt    60
ggtgaagtac atgaagtgtt caaagatctt gctacccttg tgcattccca aggaatcata   120
atcggcaagt ctttacattg tatttgtcat atgctgtcct agttttttagc ttcttatagc   180 taacgtgtac actgccctgt tccagaggaa atcgacatga acattgaaaa ttctgcagca   240
gtgaccaaag aggcaaagac agaggtcgcc aaagcagyca agactcagaa atcgaattcg   300
tccctggtaa attcagacta atgcgaacta cagaagcatt gttgccgtgt ctattctgca   360
ctctgacaaa tcatttcgtt ggcagatttg cttgcttatg gtcatatttg gggtcgtgct   420
gcttgttgtg attatagttt tggcagcttg agacatgcaa cctttcctct tacagagcta   480
ttccgcggag ttcagaattg tgattt                                        506
```

<210> SEQ ID NO 44
<211> LENGTH: 16
<212> TYPE: DNA
<213> ORGANISM: Zea mays

<400> SEQUENCE: 44
gcagcagtga ccaaag                                                        16

<210> SEQ ID NO 45
<211> LENGTH: 27
<212> TYPE: DNA
<213> ORGANISM: Zea mays

<400> SEQUENCE: 45
catgtctcaa gctgccaaaa ctataat                                            27

<210> SEQ ID NO 46
<211> LENGTH: 761
<212> TYPE: DNA
<213> ORGANISM: Zea mays
<220> FEATURE:
<221> NAME/KEY: misc_feature
<222> LOCATION: (1)..(761)
<223> OTHER INFORMATION: d is a, g, or t
<220> FEATURE:
<221> NAME/KEY: misc_feature
<222> LOCATION: (1)..(761)
<223> OTHER INFORMATION: h is a, c, or t
<220> FEATURE:
<221> NAME/KEY: misc_feature
<222> LOCATION: (1)..(761)
<223> OTHER INFORMATION: k is g or t
<220> FEATURE:
<221> NAME/KEY: misc_feature
<222> LOCATION: (1)..(761)
<223> OTHER INFORMATION: m is a or c
<220> FEATURE:
<221> NAME/KEY: misc_feature
<222> LOCATION: (1)..(761)
<223> OTHER INFORMATION: n is a, c, g, or t
<220> FEATURE:
<221> NAME/KEY: misc_feature
<222> LOCATION: (1)..(761)
<223> OTHER INFORMATION: r is a or g
<220> FEATURE:
<221> NAME/KEY: misc_feature
<222> LOCATION: (1)..(761)
<223> OTHER INFORMATION: s is c or g
<220> FEATURE:
<221> NAME/KEY: misc_feature
<222> LOCATION: (1)..(761)
<223> OTHER INFORMATION: w is a or t
<220> FEATURE:
<221> NAME/KEY: misc_feature
<222> LOCATION: (1)..(761)
<223> OTHER INFORMATION: y is c or t

<400> SEQUENCE: 46
ctctgctgcc tacartttsa aacacatgag acgagnacag gacgcgact ycatgtgaca         60 ctcacgcgtg cagtggctca catcacatgc atgcgannnn ngtgataata cacnygraga      120
agcdaaggct actgascgaa scaaaacggy taatcaacam cahcctaacg acaatggcgg      180
ttgnacacac gacggcracg gcgacggcga catgaarraa rscacamcac aggycgcgag      240
atrgcscgac raccncccwt gtccgcannt mgcatcacac gtgcgggtnr cagtagatng      300
atcttcatct sctggacgtt gcggcagtcg ccgctggscw cctggtgcac ggagcagcgg      360
sccctggatg gcgcagccga cggcggggca gcggccctgc agcgrcgagc cgtgcggsgt      420
gacggagacc gggacgcgct ggcccggctg cgcgttgggg gcyaggtaga aggagccgcc      480
gtcgacgccg acgtggaact ccacctgggc sggcgtcrgg cgcgcgcagg gcsccccgtc      540
caccagcaca cggkgaaact cggcgtggct gcgcsggtgc arcgtgtagg tgcccgcgaa      600
cagcggcggg ctgktggccc agcggctcca gcgtcagcgt cacgtcgtgg ctgcacaggt      660

| | |
|---|---|
| tctgcaccgt caccttcytg ttcttcamgc agttgtsgtk crtckcsgsg cgcrscagcr | 720 |
| scagcacrgg ccgccgccrc caggaggagc agggccgccg a | 761 |

<210> SEQ ID NO 47
<211> LENGTH: 13
<212> TYPE: DNA
<213> ORGANISM: Zea mays

<400> SEQUENCE: 47

| | |
|---|---|
| ccggctgcgc gtt | 13 |

<210> SEQ ID NO 48
<211> LENGTH: 17
<212> TYPE: DNA
<213> ORGANISM: Zea mays

<400> SEQUENCE: 48

| | |
|---|---|
| gcccaggtgg agttcca | 17 |

<210> SEQ ID NO 49
<211> LENGTH: 835
<212> TYPE: DNA
<213> ORGANISM: Zea mays
<220> FEATURE:
<221> NAME/KEY: misc_feature
<222> LOCATION: (1)..(835)
<223> OTHER INFORMATION: k is g or t
<220> FEATURE:
<221> NAME/KEY: misc_feature
<222> LOCATION: (1)..(835)
<223> OTHER INFORMATION: m is a or c
<220> FEATURE:
<221> NAME/KEY: misc_feature
<222> LOCATION: (1)..(835)
<223> OTHER INFORMATION: r is a or g
<220> FEATURE:
<221> NAME/KEY: misc_feature
<222> LOCATION: (1)..(835)
<223> OTHER INFORMATION: s is c or g
<220> FEATURE:
<221> NAME/KEY: misc_feature
<222> LOCATION: (1)..(835)
<223> OTHER INFORMATION: w is a or t
<220> FEATURE:
<221> NAME/KEY: misc_feature
<222> LOCATION: (1)..(835)
<223> OTHER INFORMATION: y is c or t

<400> SEQUENCE: 49

| | |
|---|---|
| aawgcataca katttraccg ttagttgcac ctgtttccga tccaacgacg cayggagaca | 60 |
| rgtcagtgca gcgccactac acaattccaa ttkgctccat ttattttctm gcgaagtaga | 120 |
| aaatatcatc aragcctgag cctggaagct atccmacaaa tatagataaa tatcggcact | 180 |
| tmtgtgtgca gcttccarat gctgtgctgc tcttgctgcc wcacaccgag ccaaatgact | 240 |
| gatcgaggtt acaaaaaaaa catgatcatt caacagttgt gaaaaatggt acggcygtga | 300 |
| aaagacctgc tcatttgcaa atgcgsctga acaaaccctt gtatattagc atatatcctt | 360 |
| ttgaaactgc caccacctcc aagcagtcgt cagaattgct cgttccagtg ccttacatat | 420 |
| tacaacaacc aattattctc ctgtcttaaa atccattcca ggacaaaact acagtccata | 480 |
| acacatactc tgcttctgat tttactgccr aacagatcca ccgaatctcg tgtcmtttgt | 540 |
| gacaaatgtg gggcatatta caaaaaaaga amtggccacc gaccacaacc tgaactcatt | 600 |
| atgcgtattt gtacgaactc cctcataaaa tacatgagag aaaactaatc tagcacacta | 660 |
| tgttcattag gtttgggcta aatctaccca ctgccaaacc ttgagctcac cagttccatc | 720 | cccggtaaaa aataaaccac caggacccat ctgtattgcc ctaatttctt ttttggagaa    780 taatctgcct ctgtcactga acctataaaa caaacaagag tcactcccga tagca          835

<210> SEQ ID NO 50
<211> LENGTH: 27
<212> TYPE: DNA
<213> ORGANISM: Zea mays

<400> SEQUENCE: 50
agtcgtcaga attgctcgtt ccagtgc                                         27

<210> SEQ ID NO 51
<211> LENGTH: 20
<212> TYPE: DNA
<213> ORGANISM: Zea mays

<400> SEQUENCE: 51
cgagattcgg tggatctgtt                                                 20

<210> SEQ ID NO 52
<211> LENGTH: 959
<212> TYPE: DNA
<213> ORGANISM: Zea mays
<220> FEATURE:
<221> NAME/KEY: misc_feature
<222> LOCATION: (1)..(959)
<223> OTHER INFORMATION: k is g or t
<220> FEATURE:
<221> NAME/KEY: misc_feature
<222> LOCATION: (1)..(959)
<223> OTHER INFORMATION: m is a or c
<220> FEATURE:
<221> NAME/KEY: misc_feature
<222> LOCATION: (1)..(959)
<223> OTHER INFORMATION: r is a or g
<220> FEATURE:
<221> NAME/KEY: misc_feature
<222> LOCATION: (1)..(959)
<223> OTHER INFORMATION: s is c or g
<220> FEATURE:
<221> NAME/KEY: misc_feature
<222> LOCATION: (1)..(959)
<223> OTHER INFORMATION: w is a or t
<220> FEATURE:
<221> NAME/KEY: misc_feature
<222> LOCATION: (1)..(959)
<223> OTHER INFORMATION: y is c or t

<400> SEQUENCE: 52
tctgtcgaat cgtgactcgt cgcttttca tgtcttcaga ttttgtccat ctgtcaaatc      60
atgtggaaaa wttggcatat cttcttgtat tctcttcctg tccttttaa tgcctccagc    120 ggattaattt ytakctagtt ccgttccatt gatctgcctc ttcagataat ataacttaaa   180
ttctcgcttt cttatgcaaa gaactaaatt acttgcrttg ctggctgctt tcagctgaga   240
tctccagcat ggggagggga aggattgaga tcaagaggat cgagaacaac acgagccggc   300
aggtcacctt ctgcaarcgc cgcaatgggc tcctcaagaa ggcstacgag ctctccgtcc   360
tmtgcgacgc cgaggtggcg ctcgtcgtct tctccagccg cggacgcctc tacgagtacg   420
ccaacaacag gtgcgtgcgt gatgcgtgca ctgcrgaccw agctgtcatt tcatgcacaa   480
gtgatcgaat ggctgattgt tgttgcctcc tcatcatggg taytagcact actggtagat   540
gtgtaatyar cagaaaaaat gaatgtgrat tcattttggt agtgcartgg cckgcgcctg   600
tacgtgggmc rgattagtt cctcattggt cgttcatgaa tacattggtt artgaggatt    660

```
tctatataca aaatttagtt tttttgggt tcattcayac ayatatctcc gctagytttg      720
atgtgttttg taaggagmtg gtctcattcc tcttactagc gataaagcca gatatttgtt      780
tttcattatc caaaaagtgt tatttagatt cyctgagcty aaacatccat ggtctagttt      840
aattaaycta tttctcgttc atcatacatt aggttcaacc aaattgacaa aggatgcatt      900
ttcgtattgg tgctagatga wgaagtttgc ccacacstct tctgccctgt caaatgcca       959
```

<210> SEQ ID NO 53
<211> LENGTH: 20
<212> TYPE: DNA
<213> ORGANISM: Zea mays

<400> SEQUENCE: 53

```
atcgtgactc gtcgcttttt                                                 20
```

<210> SEQ ID NO 54
<211> LENGTH: 18
<212> TYPE: DNA
<213> ORGANISM: Zea mays

<400> SEQUENCE: 54

```
aggcagatca atggaacg                                                   18
```

<210> SEQ ID NO 55
<211> LENGTH: 783
<212> TYPE: DNA
<213> ORGANISM: Zea mays
<220> FEATURE:
<221> NAME/KEY: misc_feature
<222> LOCATION: (1)..(783)
<223> OTHER INFORMATION: k is g or t
<220> FEATURE:
<221> NAME/KEY: misc_feature
<222> LOCATION: (1)..(783)
<223> OTHER INFORMATION: m is a or c
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (1)..(783)
<223> OTHER INFORMATION: r is a or g
<220> FEATURE:
<221> NAME/KEY: misc_feature
<222> LOCATION: (1)..(783)
<223> OTHER INFORMATION: s is c or g
<220> FEATURE:
<221> NAME/KEY: misc_feature
<222> LOCATION: (1)..(784)
<223> OTHER INFORMATION: v is a, c, or g
<220> FEATURE:
<221> NAME/KEY: misc_feature
<222> LOCATION: (1)..(783)
<223> OTHER INFORMATION: w is a or t
<220> FEATURE:
<221> NAME/KEY: misc_feature
<222> LOCATION: (1)..(783)
<223> OTHER INFORMATION: y is c or t

<400> SEQUENCE: 55

```
tggcaggttg gcagaacnag taccagaagg tggagagtct tccagtggcc tacttgtcaa      60
gaagggattc acrtatcaga ttatggctcc tgaagatctc cgtgtgttca crcagttrtc     120
tacagctaac atcattcagc gtatcgcggt cccttactct ggatcttttg aagtcataag     180
gtacagactg aaacaaatat acgagagcgt ggagtcagca acagaggaat ctgatgttcc     240
racgttaatc gtgcatgaaa gagtgacggt tcgcctggat tcagaaagtt atgttacact     300
```

```
gcagtggtcg tccgatccca tcagcgacat ggtktctgat tctgtggtgg ctatggtctt    360
gaacatyggt cggggcccca aagttgttcc ggtcgaagaa gckgtgaaga ccaaagagga    420
gaykgagaag gctgcyctaa aggtggtgta tgctcttatg acatcgcttt tcggtgacgt    480
taragtcgca gaggaaggga aatttgtcat atctgtagat gggaatgtgg cvcacttgga    540
tgggaggagt ggcgatgtcg aatgtgaaaa tgctacgctg aaggaacgga tcaagaccgc    600
sttccgtcgy atacagggcg ccgtgagacc aatcccacty tcagcctckt rayaacttgt    660
ttgacatttc ccatttgaac atagcattct ctgtttacac cagagtaccg ggttkttttty   720 yycwmtcwat cgaaakgaay cccagatgcc ttgtacggca tgctactcaa gaggatttga    780
ttg                                                                   783

<210> SEQ ID NO 56
<211> LENGTH: 22
<212> TYPE: DNA
<213> ORGANISM: Zea mays

<400> SEQUENCE: 56
ctgattctgt ggtggctatg gt                                              22

<210> SEQ ID NO 57
<211> LENGTH: 21
<212> TYPE: DNA
<213> ORGANISM: Zea mays

<400> SEQUENCE: 57
cttcgaccgg aacaactttg g                                               21

<210> SEQ ID NO 58
<211> LENGTH: 654
<212> TYPE: DNA
<213> ORGANISM: Zea mays
<220> FEATURE:
<221> NAME/KEY: misc_feature
<222> LOCATION: (1)..(654)
<223> OTHER INFORMATION: k is g or t
<220> FEATURE:
<221> NAME/KEY: misc_feature
<222> LOCATION: (1)..(654)
<223> OTHER INFORMATION: r is a or g
<220> FEATURE:
<221> NAME/KEY: misc_feature
<222> LOCATION: (1)..(654)
<223> OTHER INFORMATION: s is c or g
<220> FEATURE:
<221> NAME/KEY: misc_feature
<222> LOCATION: (70)..(70)
<223> OTHER INFORMATION: n is a, c, g, or t

<400> SEQUENCE: 58
atcggaacgg tcagttactc aatttttagc tcttttctgc acgagtcaaa cacacgcata    60
tggtaccgan ctgtactgtt ttggactgta cgccgtgtgg cggtgtggga acttaaaast   120
atgacttgac atctagtgca atccagaaga agcggaaaat gtgacagcga catgtatttt   180
cttggtcgga gacgcaggtc gtagcggntg gcccaggccc cctggacgag ganggcgaga   240
ggctcgcgct gtccgtctcc gcggggagca ctgtcctgta ctccaagtac gccggcagcg   300
agttcaaggg cgccgacgnc acgaactaca tcgtgctgag ggcgtcggat ctgatggccg   360
ttctctcctg aactgggctt ggnctggagg acgaacgagg tgcaggnnnn nnagcaggct   420
tagcaatacn gtaggnttcc tcgcggcttt ccsntcccct ccccsctcct acttggttgt   480
```

```
cttgtttgac tgtcttctga ggaaccgaac aacagtaata agcacaccga tgccgttcat    540
acagatnacn gtctgcctgc cctgcctaca cccgtgacag ccccaacccg atcagagtac    600
cccagctgcc acaaaagnac agtcctgacc gttnngnncc ccnaaacacc gcac          654
```

<210> SEQ ID NO 59
<211> LENGTH: 17
<212> TYPE: DNA
<213> ORGANISM: Zea mays

<400> SEQUENCE: 59

```
gtggcggtgt gggaact                                                    17
```

<210> SEQ ID NO 60
<211> LENGTH: 23
<212> TYPE: DNA
<213> ORGANISM: Zea mays

<400> SEQUENCE: 60

```
ccgcttcttc tggattgcac tag                                             23
```

<210> SEQ ID NO 61
<211> LENGTH: 449
<212> TYPE: DNA
<213> ORGANISM: Zea mays
<220> FEATURE:
<221> NAME/KEY: misc_feature
<222> LOCATION: (17)..(442)
<223> OTHER INFORMATION: n is a, c, g, or t
<220> FEATURE:
<221> NAME/KEY: misc_feature
<222> LOCATION: (347)..(347)
<223> OTHER INFORMATION: k is g or t

<400> SEQUENCE: 61

```
cagcacgcac agtacangtt gacagaaacc cgtacagatt atcttcgcat nttcaaccca    60
ntcctgaacc tagtcaacaa aaatgccaca cgttggcctg atctccccat gatcgccgac   120
aagcacgtcg gtgcggccca tcttgaccat cgccgnggcg aagtccgcgt agtactcgtc   180
gggcgacgac gccttgncca ccttctcgac gtagcctctg gtgacggggt cgtgcaggag   240
gctgccgtcg gactggaaca gcccgcccgt ggcgagnacg tggcggtagt agctcaggtc   300
gaaggtgtag ttgctgccgg ggtccaaagg caccttgacc ttcctakcat cgtcgnnncc   360
gggtctggga ggnnncgggc agagcttcct gagctcggcg gcgtangccg ggtccagcga   420
cnggtcctgg ccgtccntgt nnccggtga                                      449
```

<210> SEQ ID NO 62
<211> LENGTH: 21
<212> TYPE: DNA
<213> ORGANISM: Zea mays

<400> SEQUENCE: 62

```
caggtcgaag gtgtagttgc t                                               21
```

<210> SEQ ID NO 63
<211> LENGTH: 16
<212> TYPE: DNA
<213> ORGANISM: Zea mays

<400> SEQUENCE: 63

```
ccgccgagct caggaa                                                     16
```

```
<210> SEQ ID NO 64
<211> LENGTH: 747
<212> TYPE: DNA
<213> ORGANISM: Zea mays
<220> FEATURE:
<221> NAME/KEY: misc_feature
<222> LOCATION: (17)..(746)
<223> OTHER INFORMATION: n is a, c, g, or t
<220> FEATURE:
<221> NAME/KEY: misc_feature
<222> LOCATION: (356)..(356)
<223> OTHER INFORMATION: r is a or g

<400> SEQUENCE: 64
caaacaaatg aataacnctt tnnntttntt tttcttttnt aaagagaata tgacatnaac      60
ttcattnnna ttaacctttg catttggcat gtttggataa cttagatcaa gctgcttcca     120
tatcaagtct tttatccaat tctgtacact gnttaaccaa atctaagcat aaatcacatc     180
tgaaccgaca acagtaaatg caaagcaaaa nttgtttaaa cagagaanag tacagtggaa     240
gcaatagcaa atagctcagt acctgttctc ttgagttccc ctgattgcaa caattatcga     300
attcagacta tgatctacac caacaaatgc ctgttacatt attcatccaa agaacrgtag     360
gtgaagggaa gaatatatct tgaaaagctt gataaagttt natagcaaag agtcatacaa     420
cttcactgaa aanttatgat angttaatcc aaaatgccga ggcataggta cctgcaagca     480
gttctccaca tcaacaatta gagntctcat ctngaatccc tatttcaaca atatgaaacc     540
atatnaaaac tanaagccag ccactctaaa gnacaacttt ntgtttnaaa gaatttcatt     600
aagctgaaga gaacaaactt ganggtctct tacttgagtc aagtcattgc atcttgagca     660
tgtccacgta aacagagcgg ttaaatctgt catatacacc tagagannnn nnncaacana     720
aaatcatgag attaagctca ctttgnc                                         747

<210> SEQ ID NO 65
<211> LENGTH: 25
<212> TYPE: DNA
<213> ORGANISM: Zea mays

<400> SEQUENCE: 65
tctacaccaa caaatgcctg ttaca                                            25

<210> SEQ ID NO 66
<211> LENGTH: 27
<212> TYPE: DNA
<213> ORGANISM: Zea mays

<400> SEQUENCE: 66
ttcagtgaag ttgtatgact ctttgct                                          27

<210> SEQ ID NO 67
<211> LENGTH: 16
<212> TYPE: DNA
<213> ORGANISM: Zea mays

<400> SEQUENCE: 67
catcatggat ccattc                                                      16

<210> SEQ ID NO 68
<211> LENGTH: 16
<212> TYPE: DNA
<213> ORGANISM: Zea mays

<400> SEQUENCE: 68
```

```
catcatgggt ccattc                                              16

<210> SEQ ID NO 69
<211> LENGTH: 13
<212> TYPE: DNA
<213> ORGANISM: Zea mays

<400> SEQUENCE: 69
cagcgaggaa gca                                                 13

<210> SEQ ID NO 70
<211> LENGTH: 13
<212> TYPE: DNA
<213> ORGANISM: Zea mays

<400> SEQUENCE: 70
cagcgaagaa gca                                                 13

<210> SEQ ID NO 71
<211> LENGTH: 15
<212> TYPE: DNA
<213> ORGANISM: Zea mays

<400> SEQUENCE: 71
cccctctttt tcctc                                               15

<210> SEQ ID NO 72
<211> LENGTH: 15
<212> TYPE: DNA
<213> ORGANISM: Zea mays

<400> SEQUENCE: 72
cccctcttct tcctc                                               15

<210> SEQ ID NO 73
<211> LENGTH: 20
<212> TYPE: DNA
<213> ORGANISM: Zea mays

<400> SEQUENCE: 73
ctgtaacata ttcggaatga                                          20

<210> SEQ ID NO 74
<211> LENGTH: 20
<212> TYPE: DNA
<213> ORGANISM: Zea mays

<400> SEQUENCE: 74
ctgtaacata ttcagaatga                                          20

<210> SEQ ID NO 75
<211> LENGTH: 17
<212> TYPE: DNA
<213> ORGANISM: Zea mays

<400> SEQUENCE: 75
aacctgtgag ttttcaa                                             17

<210> SEQ ID NO 76
<211> LENGTH: 15
<212> TYPE: DNA
<213> ORGANISM: Zea mays

<400> SEQUENCE: 76
```
cctgtgagtt tttca                                                                15

<210> SEQ ID NO 77
<211> LENGTH: 12
<212> TYPE: DNA
<213> ORGANISM: Zea mays

<400> SEQUENCE: 77
tgagccaaaa ac                                                                   12

<210> SEQ ID NO 78
<211> LENGTH: 13
<212> TYPE: DNA
<213> ORGANISM: Zea mays

<400> SEQUENCE: 78
tgagccagaa act                                                                  13

<210> SEQ ID NO 79
<211> LENGTH: 15
<212> TYPE: DNA
<213> ORGANISM: Zea mays

<400> SEQUENCE: 79
ccttgaccaa gcaat                                                                15

<210> SEQ ID NO 80
<211> LENGTH: 14
<212> TYPE: DNA
<213> ORGANISM: Zea mays

<400> SEQUENCE: 80
cttggccaag caat                                                                 14

<210> SEQ ID NO 81
<211> LENGTH: 15
<212> TYPE: DNA
<213> ORGANISM: Zea mays

<400> SEQUENCE: 81
agctacgcac agatg                                                                15

<210> SEQ ID NO 82
<211> LENGTH: 15
<212> TYPE: DNA
<213> ORGANISM: Zea mays

<400> SEQUENCE: 82
agctacgcgc agatg                                                                15

<210> SEQ ID NO 83
<211> LENGTH: 16
<212> TYPE: DNA
<213> ORGANISM: Zea mays

<400> SEQUENCE: 83
acgatctcgc ctagct                                                               16

<210> SEQ ID NO 84
<211> LENGTH: 16
<212> TYPE: DNA
<213> ORGANISM: Zea mays

```
<400> SEQUENCE: 84
acgatctcgc cgagct                                                    16

<210> SEQ ID NO 85
<211> LENGTH: 13
<212> TYPE: DNA
<213> ORGANISM: Zea mays

<400> SEQUENCE: 85
atgggcgtct tct                                                       13

<210> SEQ ID NO 86
<211> LENGTH: 14
<212> TYPE: DNA
<213> ORGANISM: Zea mays

<400> SEQUENCE: 86
catgggcatc ttct                                                      14

<210> SEQ ID NO 87
<211> LENGTH: 14
<212> TYPE: DNA
<213> ORGANISM: Zea mays

<400> SEQUENCE: 87
ccgaatggca cttc                                                      14

<210> SEQ ID NO 88
<211> LENGTH: 14
<212> TYPE: DNA
<213> ORGANISM: Zea mays

<400> SEQUENCE: 88
ccgaatgaca cttc                                                      14

<210> SEQ ID NO 89
<211> LENGTH: 19
<212> TYPE: DNA
<213> ORGANISM: Zea mays

<400> SEQUENCE: 89
aaatttgatg acgatgcat                                                 19

<210> SEQ ID NO 90
<211> LENGTH: 20
<212> TYPE: DNA
<213> ORGANISM: Zea mays

<400> SEQUENCE: 90
tctgaaattt gatgatgcat                                                20

<210> SEQ ID NO 91
<211> LENGTH: 14
<212> TYPE: DNA
<213> ORGANISM: Zea mays

<400> SEQUENCE: 91
cttccccggc cgag                                                      14

<210> SEQ ID NO 92
<211> LENGTH: 17
<212> TYPE: DNA
<213> ORGANISM: Zea mays
```

```
<400> SEQUENCE: 92
ttccttccct ggccgag                                                        17

<210> SEQ ID NO 93
<211> LENGTH: 15
<212> TYPE: DNA
<213> ORGANISM: Zea mays

<400> SEQUENCE: 93
ctgctcaggg atgtt                                                          15

<210> SEQ ID NO 94
<211> LENGTH: 15
<212> TYPE: DNA
<213> ORGANISM: Zea mays

<400> SEQUENCE: 94
ctgctcagag atgtt                                                          15

<210> SEQ ID NO 95
<211> LENGTH: 23
<212> TYPE: DNA
<213> ORGANISM: Zea mays

<400> SEQUENCE: 95
aagacagagg tcgccaaagc agt                                                 23

<210> SEQ ID NO 96
<211> LENGTH: 23
<212> TYPE: DNA
<213> ORGANISM: Zea mays

<400> SEQUENCE: 96
aagacagagg tcgccaaagc agc                                                 23

<210> SEQ ID NO 97
<211> LENGTH: 15
<212> TYPE: DNA
<213> ORGANISM: Zea mays

<400> SEQUENCE: 97
ttctacctgg ccccc                                                          15

<210> SEQ ID NO 98
<211> LENGTH: 16
<212> TYPE: DNA
<213> ORGANISM: Zea mays

<400> SEQUENCE: 98
cttctaccta gccccc                                                         16

<210> SEQ ID NO 99
<211> LENGTH: 24
<212> TYPE: DNA
<213> ORGANISM: Zea mays

<400> SEQUENCE: 99
acacgagatt cggtggatct gttc                                                24

<210> SEQ ID NO 100
<211> LENGTH: 24
<212> TYPE: DNA
```

<213> ORGANISM: Zea mays

<400> SEQUENCE: 100
acacgagatt cggtggatct gttt                                          24

<210> SEQ ID NO 101
<211> LENGTH: 25
<212> TYPE: DNA
<213> ORGANISM: Zea mays

<400> SEQUENCE: 101
ggcagatcaa tggaacggaa ctagc                                         25

<210> SEQ ID NO 102
<211> LENGTH: 25
<212> TYPE: DNA
<213> ORGANISM: Zea mays

<400> SEQUENCE: 102
ggcagatcaa tggaacggaa ctaga                                         25

<210> SEQ ID NO 103
<211> LENGTH: 14
<212> TYPE: DNA
<213> ORGANISM: Zea mays

<400> SEQUENCE: 103
ccgaccaatg ttca                                                     14

<210> SEQ ID NO 104
<211> LENGTH: 14
<212> TYPE: DNA
<213> ORGANISM: Zea mays

<400> SEQUENCE: 104
ccgaccgatg ttca                                                     14

<210> SEQ ID NO 105
<211> LENGTH: 19
<212> TYPE: DNA
<213> ORGANISM: Zea mays

<400> SEQUENCE: 105
atgtcaagtc atagtttta                                                19

<210> SEQ ID NO 106
<211> LENGTH: 19
<212> TYPE: DNA
<213> ORGANISM: Zea mays

<400> SEQUENCE: 106
atgtcaagtc atacttta                                                 19

<210> SEQ ID NO 107
<211> LENGTH: 16
<212> TYPE: DNA
<213> ORGANISM: Zea mays

<400> SEQUENCE: 107
ccttcctagc atcgtc                                                   16

<210> SEQ ID NO 108
<211> LENGTH: 17

```
<212> TYPE: DNA
<213> ORGANISM: Zea mays

<400> SEQUENCE: 108
accttcctat catcgtc                                                        17

<210> SEQ ID NO 109
<211> LENGTH: 19
<212> TYPE: DNA
<213> ORGANISM: Zea mays

<400> SEQUENCE: 109
atccaaagaa cagtaggtg                                                      19

<210> SEQ ID NO 110
<211> LENGTH: 17
<212> TYPE: DNA
<213> ORGANISM: Zea mays

<400> SEQUENCE: 110
ccaaagaacg gtaggtg                                                        17

<210> SEQ ID NO 111
<211> LENGTH: 106
<212> TYPE: DNA
<213> ORGANISM: Zea mays
<220> FEATURE:
<221> NAME/KEY: misc_feature
<222> LOCATION: (60)..(82)
<223> OTHER INFORMATION: n is a, c, g, or t

<400> SEQUENCE: 111
gggtcatccc accaaatttg aggaatggay ccatgatgca ccaccatatt ttggatggan          60
tgattcctca aaccaaacac cncctacatc tggcagttga tgatgc                       106

<210> SEQ ID NO 112
<211> LENGTH: 136
<212> TYPE: DNA
<213> ORGANISM: Zea mays
<220> FEATURE:
<221> NAME/KEY: misc_feature
<222> LOCATION: (47)..(112)
<223> OTHER INFORMATION: n is a, c, g, or t

<400> SEQUENCE: 112
gacggcatgg caagcatgct tcytcgctgc atgcactcac accgccnatg atggcggtgn         60
gacgaccagn nnnncttcgc tcacagcacc ttcttcttct ttgcccctct tnttcctctt        120
cctcgacatc atacga                                                       136

<210> SEQ ID NO 113
<211> LENGTH: 160
<212> TYPE: DNA
<213> ORGANISM: Zea mays
<220> FEATURE:
<221> NAME/KEY: misc_feature
<222> LOCATION: (60)..(131)
<223> OTHER INFORMATION: n is a, c, g, or t

<400> SEQUENCE: 113
ctcacagcac cttcttcttc tttgcccctc ttyttcctct tcctcgacat catacgatgn         60
aannnnnntg tgcttcacga gntcggtgtg agtgggncnn nnacactngt nnggccttag        120
cttggccaat nttcctttct tttataggca tcttctcgtc                              160
```

```
<210> SEQ ID NO 114
<211> LENGTH: 122
<212> TYPE: DNA
<213> ORGANISM: Zea mays
<220> FEATURE:
<221> NAME/KEY: misc_feature
<222> LOCATION: (17)..(97)
<223> OTHER INFORMATION: n is a, c, g, or t

<400> SEQUENCE: 114
caccagccct gcccttnttt ctgttgaata gctgattgaa aaaannctgg aaatncattc      60
tgctgtaaca tattcrgaat gataccatga ggatttnttc tgctgtgttt cttgttctttg   120 gg                                                                   122

<210> SEQ ID NO 115
<211> LENGTH: 121
<212> TYPE: DNA
<213> ORGANISM: Zea mays

<400> SEQUENCE: 115
tgctgcactg aggttcactc atgaagacct tgtcgcatcc ctgaacctgt gagttttca      60 aagtgtagta atcctatata cttaggcact gtatgcgact gttatttggc agcacttgta   120
a                                                                    121

<210> SEQ ID NO 116
<211> LENGTH: 84
<212> TYPE: DNA
<213> ORGANISM: Zea mays

<400> SEQUENCE: 116
acgcatgaaa gaatgagcca cccggtgagc caraaactct acaaaattgc cgccgcacga     60
agtacagtcg ctttacggct tctg                                           84

<210> SEQ ID NO 117
<211> LENGTH: 74
<212> TYPE: DNA
<213> ORGANISM: Zea mays

<400> SEQUENCE: 117
gagcatggta aaccttggca aaggtgcctt grccaagcaa tttccccatc tcatacttgt     60
gcaagagaac gttc                                                      74

<210> SEQ ID NO 118
<211> LENGTH: 46
<212> TYPE: DNA
<213> ORGANISM: Zea mays

<400> SEQUENCE: 118
cgcccacgtc cgtgaacatc tgygcgtagc tcgtgtcgcc ctgcct                    46

<210> SEQ ID NO 119
<211> LENGTH: 74
<212> TYPE: DNA
<213> ORGANISM: Zea mays
<220> FEATURE:
<221> NAME/KEY: misc_feature
<222> LOCATION: (52)..(52)
<223> OTHER INFORMATION: n is a, c, g, or t

<400> SEQUENCE: 119
gctggcgcgc ttaccgatgg tggggatggt ggtgacgatc tcgcckagct tnagcttgta     60
```
gaggatggtg gtct 74

<210> SEQ ID NO 120
<211> LENGTH: 87
<212> TYPE: DNA
<213> ORGANISM: Zea mays
<220> FEATURE:
<221> NAME/KEY: misc_feature
<222> LOCATION: (28)..(28)
<223> OTHER INFORMATION: n is a, c, g, or t

<400> SEQUENCE: 120
agatatatgt gcctttgcaa gtgtgtcnct tttcatgggc rtcttcttca cacgaagaaa 60
aatgtcaaag tgcatgacat ctcaccc 87

<210> SEQ ID NO 121
<211> LENGTH: 86
<212> TYPE: DNA
<213> ORGANISM: Zea mays

<400> SEQUENCE: 121
ttcgcaggca tgatcaatcc tgtgtgaagt gycattcggc ttcatatgcc aactttagct 60
gatgaaacta agtccgtgaa tttggg 86

<210> SEQ ID NO 122
<211> LENGTH: 144
<212> TYPE: DNA
<213> ORGANISM: Zea mays
<220> FEATURE:
<221> NAME/KEY: misc_feature
<222> LOCATION: (21)..(119)
<223> OTHER INFORMATION: n is a, c, g, or t

<400> SEQUENCE: 122
gcattgcaag tggtgcgtgc nnnnntgcat gttctgaaat ttgatgacga tgcatnnnnn 60
nnngcatnnn nngcnnnnng nnagcnnnnc gtttgatgnn natctgctgt ncattnnnnc 120
tgcagatgtc ggtggagttt cagg 144

<210> SEQ ID NO 123
<211> LENGTH: 101
<212> TYPE: DNA
<213> ORGANISM: Zea mays
<220> FEATURE:
<221> NAME/KEY: misc_feature
<222> LOCATION: (28)..(60)
<223> OTHER INFORMATION: n is a, c, g, or t

<400> SEQUENCE: 123
ccagcatgta aattcatcca agcaacanaa acaaaaactc ggccrgggaa ggaaanacnn 60
ccctcccggt attctattaa gaagagaccg aaacatggtc c 101

<210> SEQ ID NO 124
<211> LENGTH: 107
<212> TYPE: DNA
<213> ORGANISM: Zea mays
<220> FEATURE:
<221> NAME/KEY: misc_feature
<222> LOCATION: (26)..(70)
<223> OTHER INFORMATION: n is a, c, g, or t

<400> SEQUENCE: 124
ttccacggac aagatcaaaa ccatangcag tcacactgct cagrgatgtt agggtcctgc 60

```
attcaaaagn acagcaagta tgatgtcatc acaaaagggt ctaggag          107
```

<210> SEQ ID NO 125
<211> LENGTH: 227
<212> TYPE: DNA
<213> ORGANISM: Zea mays

<400> SEQUENCE: 125

```
ttctgcagca gtgaccaaag aggcaaagac agaggtcgcc aaagcagyca agactcagaa    60
atcgaattcg tccctggtaa attcagacta atgcgaacta cagaagcatt gttgccgtgt   120
ctattctgca ctctgacaaa tcatttcgtt ggcagatttg cttgcttatg gtcatatttg   180
gggtcgtgct gcttgttgtg attatagttt tggcagcttg agacatg                227
```

<210> SEQ ID NO 126
<211> LENGTH: 67
<212> TYPE: DNA
<213> ORGANISM: Zea mays

<400> SEQUENCE: 126

```
ccggctgcgc gttgggggcy aggtagaagg agccgccgtc gacgccgacg tggaactcca    60
cctgggc                                                              67
```

<210> SEQ ID NO 127
<211> LENGTH: 146
<212> TYPE: DNA
<213> ORGANISM: Zea mays

<400> SEQUENCE: 127

```
agtcgtcaga attgctcgtt ccagtgcctt acatattaca caaccaatt attctcctgt     60
cttaaaatcc attccaggac aaaactacag tccataacac atactctgct tctgatttta   120
ctgccraaca gatccaccga atctcg                                        146
```

<210> SEQ ID NO 128
<211> LENGTH: 153
<212> TYPE: DNA
<213> ORGANISM: Zea mays

<400> SEQUENCE: 128

```
atcgtgactc gtcgcttttt catgtcttca gattttgtcc atctgtcaaa tcatgtggaa    60
aawttggcat atcttcttgt attctcttcc tgtccttttt aatgcctcca gcggattaat   120
ttytakctag ttccgttcca ttgatctgcc tct                                153
```

<210> SEQ ID NO 129
<211> LENGTH: 66
<212> TYPE: DNA
<213> ORGANISM: Zea mays

<400> SEQUENCE: 129

```
ctgattctgt ggtggctatg gtcttgaaca tyggtcggga rggccccaaa gttgttccgg    60
tcgaag                                                               66
```

<210> SEQ ID NO 130
<211> LENGTH: 59
<212> TYPE: DNA
<213> ORGANISM: Zea mays

<400> SEQUENCE: 130

```
gtggcggtgt gggaacttaa aastatgact tgacatctag tgcaatccag aagaagcgg     59
```

<210> SEQ ID NO 131
<211> LENGTH: 107
<212> TYPE: DNA
<213> ORGANISM: Zea mays
<220> FEATURE:
<221> NAME/KEY: misc_feature
<222> LOCATION: (62)..(81)
<223> OTHER INFORMATION: n is a, c, g, or t

<400> SEQUENCE: 131
caggtcgaag gtgtagttgc tgccggggtc caaaggcacc ttgaccttcc takcatcgtc    60
gnnnccgggt ctgggaggnn ncgggcagag cttcctgagc tcggcgg                 107

<210> SEQ ID NO 132
<211> LENGTH: 117
<212> TYPE: DNA
<213> ORGANISM: Zea mays
<220> FEATURE:
<221> NAME/KEY: misc_feature
<222> LOCATION: (88)..(88)
<223> OTHER INFORMATION: n is a, c, g, or t

<400> SEQUENCE: 132
tctacaccaa caaatgcctg ttacattatt catccaaaga acrgtaggtg aagggaagaa    60
tatatcttga aaagcttgat aaagtttnat agcaaagagt catacaactt cactgaa      117

<210> SEQ ID NO 133
<211> LENGTH: 828
<212> TYPE: DNA
<213> ORGANISM: Zea mays

<400> SEQUENCE: 133
cccttggtgt agccaggtgc gacaacattg gcgccaccac cgttgcccat gtaaagtccc    60
tgctggaagc ccttcaccac tccagctcca cagatggcac ccaggcattg catgatgatg   120
tagaagaggg ccctagtcag ggacagcttc ctggctaaga acagcccgaa agtcacagct   180
gggttgatgt gtcctcctgt tgcagtagca ggtaacaacc attagtggtg tctttggttg   240
ttgtagttgt gttcttggtc tatgcttgct gaattgcatg gattctttca cagttcgatg   300
ctttgaaatt aagcatgtat ctggagtcaa ttacacaaac catgaccagg aaagtactat   360
gcaaattaac catatgtcgg accactactg tttttgagat ggaatgacca ctgtaggtta   420
actgatatag ttttctatgt acacacctca caagttaaaa tggtgccttt tgtactttaa   480
tctttaattt tttacacaca actgtggccc gaagtgctga catgaactac tagcatgttt   540
ggtttgagga atgagctagt ccatcatatt ctcactcctc acttttttg tttggtttgt    600 ggaatagaat gagttgatct atcatcacct cattccttat agttagttag ttagtactaa   660
tatgaggaat ggggtcatcc caccaaattt gaggaatgga tccatgatgc accaccatat   720
tttggatgga atgattcctc aaaccaaaca cccctacat ctggcagttg atgatgcctt    780
tgcataatta cacgcagcac atgctatagt agtacagtat gttacatg                828

<210> SEQ ID NO 134
<211> LENGTH: 719
<212> TYPE: DNA
<213> ORGANISM: Zea mays

<400> SEQUENCE: 134
caaattaaag atcagctcga tcaagttaat taacacggca cacatatagc attacattct    60

| | |
|---|---|
| tattcagaga tactcacaca caaacacac cagacaactg aaaatacgac acggactcac | 120 |
| acggtcaaaa tacaacgcca ggttcactca ctgacacttg aacacacacg ctcacacatt | 180 |
| cactctgaac tggtcattat tctagctgta aatcaacacg gagatggagc acacagtcac | 240 |
| acacacacac agagacatga ccgctaagga tcaggagacc agtaagtaac gatcgattgc | 300 |
| cccctcctcc aaacacatag aatgatttag atggagagag ggagacctgg aagaaaggct | 360 |
| tagccttccc ttgccgataa gacttgcctt ctttcttgtg caccgccgaa gcatccctgc | 420 |
| tcacacgcca ccagcccgcg gcgccgaagc tccgggcgga cggcatggca agcatgcttc | 480 |
| ctcgctgcat gcactcacac cgccgatgat ggcggtgcga cgaccagtgc ttcgctcaca | 540 |
| gcaccttctt cttctttgcc cctctttttc ctcttcctcg acatcatacg atggaaactg | 600 |
| tgcttcacga gttcggtgtg agtgggccgg gaacactggt caggccttag cttggccaat | 660 |
| cttcctttct tttataggca tcttctcgtc aactgaatca cgcaagtctg tgcgagcga | 719 |

<210> SEQ ID NO 135
<211> LENGTH: 796
<212> TYPE: DNA
<213> ORGANISM: Zea mays

<400> SEQUENCE: 135

| | |
|---|---|
| ataatttcat ggaaagaagc atgtacttac ttgatttggg atattgtcag tttgtcacct | 60 |
| taatttattg agttaataca tcactataag accataaaca ggaccccaaa tttgcacact | 120 |
| tctaatccag catatgcatt attttataaa aatgataatg atttgctcaa ccagccatgg | 180 |
| tttcacgaat cactgttgag tcttttaact gcaaaagccg ctcacaattt ttttagttaa | 240 |
| atttgaattt agatttttt ttgaaaactg attctgtact tctagttgga aacttagaat | 300 |
| gcatgactgc taaagccact cctaattgga atgcatgaca ttttgtattg tttatgattt | 360 |
| tatttccttt gaaatatttg gaagaaatt ttctattaga agtttgaggg aacatagata | 420 |
| ttgtgtcaaa tgtttttgt gaatagttaa aaaagacaga cccagtgttg gagactcata | 480 |
| catgtgtggg ctctgggaag gggataaacc aagttaaggc aagccttct ctgtaaatgc | 540 |
| ggggaggctg cttcgaatcc acgacctggt gactcagtga ggcggctctc cccactgcac | 600 |
| cagccctgcc cttctttctg ttgaatagct gattgaaaaa ttctggaaat ccattctgct | 660 |
| gtaacatatt cggaatgata ccatgaggat ttttctgct gtgttcttg ttctttggca | 720 |
| tggttggtag ggggtgaacc ttgtaacatg atattctaaa taacttgcag atgatagtta | 780 |
| acagatcacg agctaa | 796 |

<210> SEQ ID NO 136
<211> LENGTH: 859
<212> TYPE: DNA
<213> ORGANISM: Zea mays

<400> SEQUENCE: 136

| | |
|---|---|
| ctgctgcctt tggtactaag gctgttgcag ttggtgccga tatctcactt gatactgcaa | 60 |
| ctgggaactt gactaaatac aatgctgcac tgaggttcac tcatgaagac cttgtcgcat | 120 |
| ccctgaacct gtgagttttc aaagtgtagt aatcctatat acttaggcac tgtatgtgac | 180 |
| tgttatttgg cagcacttgt aatatcatta tttatggtta agtacaaatc cctgcttgat | 240 |
| gtgtctcaac ttaaagctgt tgtgtaagtg gttagtgca taaagtggg tcaaaatgtt | 300 |
| aatatattgg tcaccgtgat ttcacctttt ctcagacatt tctcaaatgg agttttgaaa | 360 |
| gaagaaactt tacaatttga ctttacttag atcgtttgca acaaactcag attattgcat | 420 |

```
gtacagaaat tgatcgaagt gactgacttt gctaagtgtt ttttgtttca ttgagaaaaa    480
tgatctattg cattaagctg gtagcaatat ggctgatatt gagccgtacc tccaggaagg    540
gtctgatatg ctcagtattt tggttttcta attgagtgaa aagtcctatg tataatctta    600
tattaaatga aattgatgtc atagcttttc aacagatgta accctgtttc ttttaggacg    660
tttactgtct tatttttttg cagtgcctgc caaatttcat gtaaccgacc caaccttctc    720
ttgcaggaac aacaagggag acagccttac tggagcctac tatcacaagg tgagcgaatt    780
gaccaacaca gctgttgggg cagagcttac ccacagcttc tcgaccaatg aaaacaccct    840
cacctttggc gggcagcac                                                 859
```

<210> SEQ ID NO 137
<211> LENGTH: 654
<212> TYPE: DNA
<213> ORGANISM: Zea mays

<400> SEQUENCE: 137

```
tacagttgca agagggtgtg ggacaaccac ttgttatttc tcagtgacga aggactgtga     60
cagttaaaaa aataaaaaat aaaaacgcat gaaagaatga gccacccggt gagccaaaaa    120
ctctacaaaa ttgccgccgc acgaagtaca gtcgctttac ggcttctgaa tcagtcgttg    180
tgttttcagt tgcgtcacag cgggtgcttc ttccatctca ccaaggaatt gaggaacccc    240
atcacctgtg tgacagacaa gcagacacac agattagagt caccagacta gaccgaacga    300
agccgacagg gtagaagcaa gtactgaagg aaaaaaaaag accacaagag gtttacttca    360
gacgggtctc tcagcgagta aaggcttca gtgtccttgg gcacctgcga gactaggatt    420
ccgtatccac agcttcgctc tcgcagtacc tggagcgagc gagagagaga gagagagaga    480
gagaggcaac aggagattct gatgagtcta gaacggctca acatgcgag tgtgagatgc    540 acaagtttcc tgagaagatg tagcaacctt gaaggcgtct tcgtctgttc gatcgtctcc    600
gatgtagata ggaaccacat cttcggagtc gcttaggccg agcgaccgaa gcag         654
```

<210> SEQ ID NO 138
<211> LENGTH: 1093
<212> TYPE: DNA
<213> ORGANISM: Zea mays

<400> SEQUENCE: 138

```
cttccttgag ccttcctcgc tgaatcttgt tgaacagctc tccacccttta acatgttcca     60 gcacaaagta tattttggtt ttggtggcca tgacctcata gagctgtacg atgtttggat    120
gcctaacaag cttcatcaca gaaatttctc gctggatttg atcaatgaga ccaaccttca    180
taaccttctc cttatcaatc actttgatcg cgacactttc cgaagtcgcc gtgttacgag    240
catggtaaac cttggcaaag gtgccttggc caagcaattt ccccatctca tacttgtgca    300
agagaacgtt cccctttatgc tctgccatct gtgcctgtgt atgctacgta tggtggtggt    360
ggtatgcaca cagaggtcac ttgcttatcc ttgacagtta aaaaaaatga dacagcaaag    420
aggtcgagag ggtgtgaaga cttcaaccgt ctccaccgag atggtgatct aagaagacgg    480
ttgagccgcc acgtcgaacc ccattgtgcg aaagcacgag gtggagatac gtgtactctt    540
gagcttcgaa gtcatcaaga ggtggcagag aatgaagagt atggcgtgct tcctgccaa    600 gtccctcaca aagtagctct tcgacgtgca agcacatctt tctgcattcc ctaaggcgtt    660
ttctgctcct tactgaaaac ccaatactgc cgaagatgta aagagaagg gcatcagtta    720
```

| | |
|---|---|
| taagatcaat acaacacata cctatctgta tatagaaata taaaatataa ttgttagtat | 780 |
| gaaaaaatt caaggataat gaaaaattgg aagaaaacag agcagatatt cttgcacgaa | 840 |
| catgtgtgca caagttagtt cagacaatcg ttacgtgagt ttgtctaatc tgattttag | 900 |
| acataagtag caaaactaaa aaaaattcta cttcataacc agatccagac agtgctgttg | 960 |
| acaccttctc aaccagatct agacagtttt gttgacacct tcttaaccag atctagacag | 1020 |
| tgttgttggc ttacgcataa accgcaaaac gaacttgatg gtttcttctg ctctaaaaaa | 1080 |
| aactttgttc gga | 1093 |

<210> SEQ ID NO 139
<211> LENGTH: 1630
<212> TYPE: DNA
<213> ORGANISM: Zea mays

<400> SEQUENCE: 139

| | |
|---|---|
| cacctccttc tccgtcttgc gccccttctt ggacttgtag tacacgctca tgaacgtgcc | 60 |
| caccgccccg tacttttggc ggcagtgctc gtagtgcgac gcgtcgaaca tgcgccagaa | 120 |
| gtccttctcg ttcagctccg acaccgcgta ctgcggctgg tagctgtggt tctcgatcag | 180 |
| ccactgctcc agcctgtgca cagcctccgc gccgttgaac tcctccccc tcagcaccgc | 240 |
| cccgggggcg tagtacacgc ccacgtccgt gaacatctgt gcgtagctcg tgtcgccctg | 300 |
| cctgtgctgt tgctcgaacc caggctccgg gtacaccatc gtcttcaccg gcagcttgta | 360 |
| cagccggtga gggcacagcc acagaggata cacctaccaa aagaatttca attattatta | 420 |
| gtatatccag tcaactactc ataaagcaag cagcaccagc accagcacca gccagccatt | 480 |
| gtacctccat ctcgcggtgc acgaactcca gcgcatcccc aaccttgtac agcggcacca | 540 |
| gcatgtcctg gatcacatgg ttgtcgtggt agtagttcct gatagcctcg ccctgggtcg | 600 |
| ccttcagcag ggacaccttc ggtggcatca gccagcccag caggaacctg aaccagaact | 660 |
| ggtcgccgaa gggcaggatc agcttccct cccagtacag gcaccgggtg tgccggtggt | 720 |
| agtactccct cgtcgggatg tactccacaa actcgcccct cttcagcgcc gtctgagcgt | 780 |
| gctggtagaa ccagggctta aaccaccacc ccacgcagtt gatcttgttg ccctttcttct | 840 |
| tcgcctcttc tttggaagcg tacacgcccg tcatcatgac accctcgctc tctgtgtaca | 900 |
| ccatcccttc aacaaagtca gggaccttg ccgggtcacc gtccctcggc gcgaaagaat | 960 |
| ccgcgtaggc ctgcgcgatc tcctttagac cccccttgac tggagtgtag gtgagcttca | 1020 |
| tgtactcctt gatggggatc agcttgatct ccgcagagac aaggaacccc agtgttccct | 1080 |
| gggaccaggg aatgccatag aaaaggtcag agtactcgtt gtccttggtg gctctgacga | 1140 |
| cccggccatc tgccgagaaca acctccatcg cgacaaccgt gtcggagaaa aggccataga | 1200 |
| ggtgagagct ccctcgatg ccgtaaccgt tgatcagccc accaacagtg aggtcgtcga | 1260 |
| gctcggcgac gaccgcaagg gcaaggttca ttgggcaggt agctctggtt atctgaccca | 1320 |
| tgttgacaag gggctcgacc ttggcaacca tcctctcttt gtcgatctca aggatgttcc | 1380 |
| tgaaggaaga aaggtcgacc tcgaaatgcc tcgcacgctt gtagtccacg ttgcgcatgc | 1440 |
| caacagcgat ccagggcttc ctggccgtgc aaacaagacc gtccttcttc gggttcctct | 1500 |
| gcttgagccg cttcacgacc ttctgcacgt tctcgtcgtg ctgcttctgg cgcttcttct | 1560 |
| ccgacttcat ggcggaccac atgtcgccca ggaagatgtt gaagtagatc agagttgaaa | 1620 |
| taggaaggac | 1630 |

<210> SEQ ID NO 140
<211> LENGTH: 857
<212> TYPE: DNA
<213> ORGANISM: Zea mays

<400> SEQUENCE: 140

| | | | | | | |
|---|---|---|---|---|---|---|
| tctgttcatt | agctgttcaa | ttaattgagt | gatcacagag | gccaacagct | ggtgcgctaa | 60 |
| aaaaactcag | tggaagagga | tgcacgtcct | atgaaaaatt | aacagaaatg | cattaagcta | 120 |
| gttcaccagt | cttgttgcgc | ctagattttt | ttagataaaa | aatgatcaaa | gtggtgagtt | 180 |
| ccgttattga | tattcgcgta | gccatgcagc | ctgaattttc | aactaaacta | ggtggccgtg | 240 |
| gaattatcca | acaactattt | ggcagccctg | tccaaaatca | tgataccacg | agcataactt | 300 |
| aattcacaac | gtggtgctta | tgtatgctgg | cgcgcttacc | gatggtgggg | atggtggtga | 360 |
| cgatctcgcc | gagcttcagc | ttgtagagga | tggtggtctt | tccggcggcg | tcgagtccca | 420 |
| ccatcaggat | ccgcatctcc | ttcttggcga | acagccggct | gaacagcttg | gtgaacgtga | 480 |
| gccccatctc | ttccctctca | cctgcagcag | acacgaaacc | caggtcatca | ggacgccgat | 540 |
| ccatcccacg | catgtccctc | acacggccac | aggccgctag | atctacgcgt | cgcagcgccc | 600 |
| agatccacct | agggaccgaa | ccgaaggccg | gcggtacga | gatccgcagg | aaatggcgag | 660 |
| cggatcgacc | ggcacgcagc | ccagagcgcg | cgaacggtcg | gcgagagcgt | tctacctagg | 720 |
| atagatcccg | tgcgcggggg | gagcgatcct | ccgtggggga | agggagggga | ggggagcggg | 780 |
| gtaggcggga | gggcgctggt | tctcaccttg | tcggcggatc | cgattcgcgg | tgtcgggctc | 840 |
| gccggcgacg | cagccgg | | | | | 857 |

<210> SEQ ID NO 141
<211> LENGTH: 517
<212> TYPE: DNA
<213> ORGANISM: Zea mays

<400> SEQUENCE: 141

| | | | | | | |
|---|---|---|---|---|---|---|
| ggcacactaa | cccactgcca | agcacctcgt | ctgatctgat | ctgatgctga | tgcagggttg | 60 |
| gcggttccgg | gatggacgtc | aggagcaaag | ccagggtcag | tagtagtaca | cgcttttgtt | 120 |
| caccttcaat | cttatcctta | tcttggcagt | gtaaaaattt | tttgtacttt | tgttggaaga | 180 |
| tagatagata | gatatatgtg | cctttgcaag | tgtgtctctt | ttcatgggcg | tcttcttcac | 240 |
| acgaagaaaa | atgtcaaagt | gcatgacatc | tcacctgcc | ttttttttgg | gagggtactc | 300 |
| agacgctgtc | cggacctgtt | gatgacccca | gcaagcttcc | gaagtggaac | ttcgacggct | 360 |
| ccagcaccgg | ccaagctccg | ggcgacgaca | gcgaagtcat | cctttggtac | ccgcgcgctt | 420 |
| tctctccagt | ccactctccc | tccgtcttca | ctcaccttga | cgtgtgtgcc | tcactaccct | 480 |
| tgctaatgcc | acgttgcgct | gattcacctt | gactctt | | | 517 |

<210> SEQ ID NO 142
<211> LENGTH: 762
<212> TYPE: DNA
<213> ORGANISM: Zea mays

<400> SEQUENCE: 142

| | | | | | | |
|---|---|---|---|---|---|---|
| agtggttcca | tcgactatgg | agagttccta | gctgcaactt | tacatctgaa | caaagtcgag | 60 |
| cgagaagaca | acctcttcgc | agcattctca | tactttgata | aagacggcag | cggttatatt | 120 |
| actcatgatg | agctacaaaa | agcatgtgag | gaattcggta | tagaagatgc | acacctagaa | 180 |
| gatatcatcc | atgacgttga | tcaggacaat | gtaagtagat | ttgcatctca | tcatgctgtg | 240 |

| | |
|---|---|
| tgtttaaatc taaaggccaa gagttgcatc ttacttggtt atcaatccag gatggtcgga | 300 |
| tcgactacaa cgagtttgta acaatgatgc agaagggaaa taacccacta gggaaaaagg | 360 |
| ggcactgcca gatgagcttt ggtcttagag aagcattgaa gcttggctaa gtggtaactg | 420 |
| gtgttttccc tttgcacttc tttcctttt gttcgcttag caatccagta tccacatgaa | 480 |
| ttcttgtgtt tctggttcct gttccatgga ttatgctcta tggcacgtgc tcaatccaat | 540 |
| atacgctata tgcttactgt ttggttgctt ttcgcaggca tgatcaatcc tgtgtgaagt | 600 |
| gccattcggc ttcatatgcc aactttagct gatgaaacta agtccgtgaa tttgggacgc | 660 |
| cggtaccaaa ggtggagcaa gtgcgcgata cgattagctt tgggatacca actaagcagt | 720 |
| gagcatgcag gaacacattg gtgatctttc gtcgttaacc cc | 762 |

<210> SEQ ID NO 143
<211> LENGTH: 788
<212> TYPE: DNA
<213> ORGANISM: Zea mays

<400> SEQUENCE: 143

| | |
|---|---|
| ggctcgggcc caagccgtac gggctcaact cggaggcgtc gcgtgacagc gccgtcgtca | 60 |
| tcatgaccca tgccaacctc gtcgaaatcc tcatggacgt ggtatgatcc atgcacatac | 120 |
| atttgatcga tcagcagctg attatgattg ctggcttctg aactttaat tcgattttct | 180 |
| tctgcgcaga accagtatgc ggccgtgttc tcgagtatcg tgtcgagagc cgcgacgctg | 240 |
| gaggtgctat caaccggcgt ggctgggaac tacaatggtg cattgcaagt ggtgcgtgca | 300 |
| tgcatgttct gaaatttgat gacgatgcat gcatgggtgg ctactagcta gctagtcgtt | 360 |
| tgatgtcgat ctgctgtcca ttattctgca gatgtcggtg gagtttcagg tgccttcccc | 420 |
| actggtgccg accagggaaa gctacttcgt gaggtactgc aagcagaacg ccgacggaac | 480 |
| atgggccgtc gtcgacgtct cgctggacgg cctgcgcccc ggcgcagtcc tcaagtgccg | 540 |
| gcgccggccg tcgggatgcc tgatccagga aatgcccaat ggctactcga aggtgacctg | 600 |
| ggtggagcac gtcgaggtgg acgacaggtc ggtgcacagc atctacaagc tgctggtgag | 660 |
| ctcggggctg gccttcggtg cacgccgatg ggttgggacg ctggaccgcc agtgcgagcg | 720 |
| ccttgccagt gtcatggcca gcaacatccc gaccagcgac atcggtggtg agatttctga | 780 |
| gacctgca | 788 |

<210> SEQ ID NO 144
<211> LENGTH: 797
<212> TYPE: DNA
<213> ORGANISM: Zea mays

<400> SEQUENCE: 144

| | |
|---|---|
| tgcatcgcag cccaatattg aaacagataa aaatacatta accagtagag agttgtacca | 60 |
| agagagaaca gaacttactt cctgagcctg agctggggtg gcgactttgc cagttccaat | 120 |
| agcccagact ggttcatagg caagaacaac gttgctccag tccttgatct tctctgtaaa | 180 |
| acaaacagcc atttgatcca ttcagcctga ttttttcgtat agggtcaaaa aacttggtaa | 240 |
| cttcaaagca aggcactaaa tgttcacatg aacaaaacaa agggcagacc cagctcccac | 300 |
| atgaatgtgg ggtctttccc ccacaaatgc ggaaggaaa atccagcatg taaattcatc | 360 |
| caagcaacag aaacaaaaac tcggccaggg aaggaaagac cgccctcccg gtattctatt | 420 |
| aagaagagac cgaacatgg tcccggccga aaaatcccc gaaccctagc cccccatcac | 480 |
| tagttggccg acatcgcgca ctctgcaaat gcccagccgg agggtggggt gcatgacata | 540 |

```
acccgagggc gggcggggca caacgaaggg attttttaac caagcccgaa attcgccccc      600 aaggggatc gaacccggga cctggaggtg ctacttggaa gctttaacca ttacgctaaa       660
ggccctttcg cagcgacaga aacacacata agttgattcc taaactaaag ctgttacaga     720
aaaacagtaa tgtccgaact ccggatatgt agattatcta acagaactga tcaccagaag    780
caaagggcct gttcagt                                                       797

<210> SEQ ID NO 145
<211> LENGTH: 555
<212> TYPE: DNA
<213> ORGANISM: Zea mays

<400> SEQUENCE: 145
gtgacaagcc caagagtttg ggttccacgg acaagatcaa aaccataagc agtcacactg       60
ctcagggatg ttagggtcct gcattcaaaa gaacagcaag tatgatgtca tcacaaaagg     120
gtctaggagg agcaatggct gagaaaaggg tgagctagcg acataaataa catacttgta     180
ggactcagca ggaacatcag caaagtaagt ctcaacaagc acattcaatc cagaaagtac     240
agattcaagt tctgcgtatg cagcagagaa tgcagccaat ttgtcagaat caaggtcgag     300
gacaagagtg ggctcatcaa actgaatcca tgaagcccca gctgccttca actcagcaat    360
gacctcccta caatcatcaa gcatcaaatt atcaactgaa gattcgaggg ccagagcagc    420
caataacttc tttataatct tacttgtaga ctggaggat gctgctaaga agggaaagaa     480
gagggaatcc cttctccaca cccttggcag gctttgagag caacaggtac gagactggtc    540
caacaagtac tggca                                                         555

<210> SEQ ID NO 146
<211> LENGTH: 741
<212> TYPE: DNA
<213> ORGANISM: Zea mays

<400> SEQUENCE: 146
ctctgctgcc tacaatttca aacacatgag acgagacagg acgacgactc atgtgacact      60
cacgcgtgca gtggctcaca tcacatgcat gcgatgcgag tgataataca ctggagagcg    120
aggctactga gcgaagcaaa cggctaatca acaacaacct aacgacaatg gcggttggac    180
acacgacggc gacggcgaca tgaaagaaag cacaacacag gtcgcgagat ggcgcgacga    240
ccccatgtcc gcatcgcatc acacgtgcgg gttgcagtag atgatcttca tctcctggac    300
gttgcggcag tcgccgctgg gcacctggtg cacggagcag cggccctgga tggcgcagcc    360
gacggcgggg cagcggccct gcagcggcga gccgtgcggg gtgacggaga ccgggacgcg    420
ctggcccggc tgcgcgttgg gggccaggta gaaggagccg ccgtcgacgc cgacgtggaa    480
ctccacctgg cggcgtcgg gcgcgcgcag gcgccccgtc caccagcaca cggggaactc    540
ggcgtggctg cgcgggtgca gcgtgtaggt gcccgcgaac agcggcgggc tgttggccag    600
cggctccagc gtcagcgtca cgtcgtggct gcacaggttc tgcaccgtca ccttcttgtt    660
cttcacgcag ttgtcgtgcg tcaggtccgc gcgcgccagc gccagcacgg ccgccgccgc    720
caggaggagc agggccgccg a                                                  741

<210> SEQ ID NO 147
<211> LENGTH: 814
<212> TYPE: DNA
<213> ORGANISM: Zea mays
```

<400> SEQUENCE: 147

```
gcatacagat tgaccgtta gttgcacctg tttccgatcc aacgacgcat ggagacaggt    60
cagtgcagcg ccactacaca attccaattg gctccattta ttttctcgcg aagtagaaaa   120
tatcatcaga gcctgagcct ggaagctatc caggaacaaa tatagataaa tatcggcaca   180
ggttctgtgt gcagcttcca aaaccgagc caaatgactg atcgaggtta caaaaaaaac    240
atgatcattc aacagttgtg aaaaatggta cggccgtgaa aagacctgct catttgcaaa   300
tgcggctgaa caaacccttg tatattagca tatatccttt tgaaactgcc accacctcca   360
agcagtcgtc agaattgctc gttccagtgc cttacatatt acaacaacca attattctcc   420
tgtcttaaaa tccattccag gacaaaacta cagtccataa cacatactct gcttctgatt   480
ttactgccga acagatccac cgaatctcgt gtcatttgtg acaaatgtgg ggcatattac   540
aaaaaaagaa ctggccaccg accacaacct gaactcatta tgcgtatttg tacgaactcc   600
ctcataaaat acatgagaga aaactaatct agcacactat gttcattagg tttgggctaa   660
atctacccac tgccaaacct tgagctcacc agttccatcc ccggtaaaaa ataaaccacc   720
aggacccatc tgtattgccc taatttcttt tttggagaat aatctgcctc tgtcactgaa   780
cctataaaac aaacaagagt cactcccgat agca                               814
```

<210> SEQ ID NO 148
<211> LENGTH: 926
<212> TYPE: DNA
<213> ORGANISM: Zea mays

<400> SEQUENCE: 148

```
tctgtcgaat cgtgactcgt cgcttttca gtcttcaga ttttgtccat ctgtcaaatc     60
atgtggaaaa attggcatat cttcttgtat tctcttctgt ccttttaat gcctccagcg   120
gattaatttc tagctagttc cgttccattg atctgccttc agataatata acttaaattc   180
tcgctttctt atgcaagaac taaattactt gcatttcagc tgagatctcc agcatgggga   240
ggggaaggat tgagatcaag aggatcgaga acaacacgag ccggcaggtc accttctgca   300
agcgccgcaa tgggctcctc aagaaggcgt acgagctctc cgtcctctgc gacgccgagg   360
tggcgctcgt cgtcttctcc agccgcggac gcctctacga gtacgccaac aacaggtgcg   420
tgcactgcgg acctagctgt catttcatgc acaagtgatc gaatggctga ttgttgttgc   480
ctcctcatgg gtactactgg agatgtgtaa tcagcagaaa aaatgaaatg taattcattt   540
tggtagtgca gtggcctgcg cctgtacgtg ggacagattt agttcctcat ggtcgttca   600
tgaatacatt ggttagtgag gatttctata agatacaaaa tttagttttt ttttgggttc   660
attcatacat atatctccgc tagttttgat gtgttttgta aggagctggt ctcattcctc   720
ttactagcga taaagccaga tatttgtttt tcattatcca aaaagtgtta tttagattct   780
ctgagcttaa acatccatgg tctagtttaa ttaatctatt tctcgttcat catacattag   840
gttcaaccaa attgacaagg atgcattttc gtattggtgc tagatgatga agtttgccca   900
cacgtcttct gccctgtcaa atgcca                                        926
```

<210> SEQ ID NO 149
<211> LENGTH: 789
<212> TYPE: DNA
<213> ORGANISM: Zea mays

<400> SEQUENCE: 149

```
tggcaggttg gcagaacaag taccagaagg tggagagtct tccagtggcc tacttgtcaa    60
```

```
gaagggattc acatatcaga ttatggctcc tgaagatctc cgtgtgttca cgcagttatc      120
tacagctaac atcattcagc gtatcgcggt cccttactct ggatcttttg aagtcataag      180
gtacagactg aaacaaatat acgagagcgt ggagtcagca acagaggaat ctgatgttcc      240
gacgttaatc gtgcatgaaa gagtgacggt tcgcctggat tcagaaagtt atgttacact      300
gcagtggtcg tccgatccca tcagcgacat ggtgtctgat tctgtggtgg ctatggtctt      360
gaacatcggt cggaaggcc ccaaagttgt tccggtcgaa gaagcggtga agaccaaaga      420
ggagacggag aaggctgccc taaaggtggt gtatgctctt atgacatcgc ttttcggtga      480
cgttaaagtc gcagaggaag ggaaatttgt catatctgta gatgggaatg tggcgcactt      540
ggatgggagg agtggcgatg tcgaatgtga aaatgctacg ctgaaggaac ggatcaagac      600
cgccttccgt cgcatacagg gcgccgtgag accaatccca ctttcagcct cttgataact      660
tgtttgacat ttcccatttg aacaaagtag cattctctgt ttacaccaga gtaccgggtt      720
ttttttccct ctctatcgaa aggaaccca gatgccttgt acggcatgct actcaagagg      780
atttgattg                                                              789

<210> SEQ ID NO 150
<211> LENGTH: 654
<212> TYPE: DNA
<213> ORGANISM: Zea mays

<400> SEQUENCE: 150
atcggaacgg tcagttactc aattttttag ctcttttctg cacgagtcaa acacacgcat       60
atggtaccga ctgtactgtt ttggactgta cgccgtgtgg cggtgtggga acttaaaagt      120
atgacttgac atctagtgca atccagaaga agcggaaaat gtgacagcga catgtatttt      180
cttggtcgga gacgcaggtc gtagcggttg gcccaggccc cctggacgag gatggcgaga      240
ggctcgcgct gtccgtctcc gcggggagca ctgtcctgta ctccaagtac gccggcagcg      300
agttcaaggg cgccgacggc acgaactaca tcgtgctgag ggcgtcggat ctgatggccg      360
ttctctcctg aactgggctt gggctggagg acgaacgagg tgcaggtgca ggagcaggct      420
tagcaatacc gtaggattcc tcgcggcttt cccgtcccct cccccctcct acttggttgt      480
cttgtttgac tgtcttctga ggaaccgaac aacagtaata agcacaccga tgccgttcat      540
acagattaca gtctgcctgc cctgcctaca cccgtgacag ccccaacccg atcagagtac      600
cccagctgcc acaaaagaac agtcctgacc gttgcgtgcc cccaaacacc gcac            654

<210> SEQ ID NO 151
<211> LENGTH: 443
<212> TYPE: DNA
<213> ORGANISM: Zea mays

<400> SEQUENCE: 151
cagcacgcac agtacacgtt gacagaaacc cgtacagatt atcttcgcat cttcaaccca       60
atcctgaacc tagtcaacaa aaatgccaca cgttggcctg atctccccat gatcgccgac      120
aagcacgtcg gtgcggccca tcttgaccat cgccgcggcg aagtccgcgt agtactcgtc      180
gggcgacgac gccttggcca ccttctcgac gtagcctctg gtgacgggt cgtgcaggag      240 gctgccgtcg gactggaaca gcccgcccgt ggcgagcacg tggcggtagt agctcaggtc      300
gaaggtgtag ttgctgccgg ggtccaaagg caccttgacc ttcctagcat cgtcgccggg      360
tctgggaggc gggcagagct tcctgagctc ggcggcgtag gccgggtcca gcgacgggtc      420
```

```
ctggccgtcc atgttgccgg tga                                          443
```

```
<210> SEQ ID NO 152
<211> LENGTH: 738
<212> TYPE: DNA
<213> ORGANISM: Zea mays

<400> SEQUENCE: 152
caaacaaatg aataacgctt tcgatttatt tttcttttct aaagagaata tgacataaac    60
ttcattggca ttaacctttg catttggcat gtttggataa cttagatcaa gctgcttcca   120
tatcaagtct tttatccaat tctgtacact ggttaaccaa atctaagcat aaatcacatc   180
tgaaccgaca acagtaaatg caaagcaaaa tttgtttaaa cagagaatag tacagtggaa   240
gcaatagcaa atagctcagt acctgttctc ttgagttccc ctgattgcaa caattatcga   300
attcagacta tgatctacac caacaaatgc ctgttacatt attcatccaa agaacagtag   360
gtgaagggaa gaatatatct tgaaaagctt gataaagttt tatagcaaag agtcatacaa   420
cttcactgaa aaattatgat aagttaatcc aaaatgccga ggcataggta cctgcaagca   480
gttctccaca tcaacaatta gagatctcat ctcgaatccc tatttcaaca atatgaaacc   540
atatcaaaac tagaagccag ccactctaaa gaacaacttt tgttttaaa gaatttcatt   600
aagctgaaga gaacaaactt gatggtctct tacttgagtc aagtcattgc atcttgagca   660
tgtccacgta aacagagcgg ttaaatctgt catatacacc tagagacaac agaaaatcat   720
gagattaagc tcactttg                                                 738
```

```
<210> SEQ ID NO 153
<211> LENGTH: 106
<212> TYPE: DNA
<213> ORGANISM: Zea mays

<400> SEQUENCE: 153
gggtcatccc accaaatttg aggaatggat ccatgatgca ccaccatatt ttggatggaa    60
tgattcctca aaccaaacac cccctacatc tggcagttga tgatgc                  106
```

```
<210> SEQ ID NO 154
<211> LENGTH: 133
<212> TYPE: DNA
<213> ORGANISM: Zea mays

<400> SEQUENCE: 154
gacggcatgg caagcatgct tcctcgctgc atgcactcac accgccgatg atggcggtgc    60
gacgaccagt gcttcgctca cagcaccttc ttcttctttg cccctctttt tcctcttcct   120
cgacatcata cga                                                      133
```

```
<210> SEQ ID NO 155
<211> LENGTH: 156
<212> TYPE: DNA
<213> ORGANISM: Zea mays

<400> SEQUENCE: 155
ctcacagcac cttcttcttc tttgcccctc tttttcctct tcctcgacat catacgatgg    60
aaactgtgct tcacgagttc ggtgtgagtg ggccgggaac actggtcagg ccttagcttg   120
gccaatcttc ctttcttta taggcatctt ctcgtc                              156
```

```
<210> SEQ ID NO 156
<211> LENGTH: 121
```

```
<212> TYPE: DNA
<213> ORGANISM: Zea mays

<400> SEQUENCE: 156
caccagccct gcccttcttt ctgttgaata gctgattgaa aaattctgga aatccattct    60
gctgtaacat attcggaatg ataccatgag gattttttct gctgtgtttc ttgttctttg   120
g                                                                   121

<210> SEQ ID NO 157
<211> LENGTH: 120
<212> TYPE: DNA
<213> ORGANISM: Zea mays

<400> SEQUENCE: 157
tgctgcactg aggttcactc atgaagacct tgtcgcatcc ctgaacctgt gagttttcaa    60
agtgtagtaa tcctatatac ttaggcactg tatgtgactg ttatttggca gcacttgtaa   120

<210> SEQ ID NO 158
<211> LENGTH: 84
<212> TYPE: DNA
<213> ORGANISM: Zea mays

<400> SEQUENCE: 158
acgcatgaaa gaatgagcca cccggtgagc caaaaactct acaaaattgc cgccgcacga    60
agtacagtcg ctttacggct tctg                                          84

<210> SEQ ID NO 159
<211> LENGTH: 74
<212> TYPE: DNA
<213> ORGANISM: Zea mays

<400> SEQUENCE: 159
gagcatggta aaccttggca aaggtgcctt ggccaagcaa tttccccatc tcatacttgt    60
gcaagagaac gttc                                                     74

<210> SEQ ID NO 160
<211> LENGTH: 46
<212> TYPE: DNA
<213> ORGANISM: Zea mays

<400> SEQUENCE: 160
cgcccacgtc cgtgaacatc tgtgcgtagc tcgtgtcgcc ctgcct                  46

<210> SEQ ID NO 161
<211> LENGTH: 74
<212> TYPE: DNA
<213> ORGANISM: Zea mays

<400> SEQUENCE: 161
gctggcgcgc ttaccgatgg tggggatggt ggtgacgatc tcgccgagct tcagcttgta    60
gaggatggtg gtct                                                     74

<210> SEQ ID NO 162
<211> LENGTH: 87
<212> TYPE: DNA
<213> ORGANISM: Zea mays

<400> SEQUENCE: 162
agatatatgt gcctttgcaa gtgtgtctct tttcatgggc gtcttcttca cacgaagaaa    60
```

```
aatgtcaaag tgcatgacat ctcaccc                                          87

<210> SEQ ID NO 163
<211> LENGTH: 86
<212> TYPE: DNA
<213> ORGANISM: Zea mays

<400> SEQUENCE: 163
ttcgcaggca tgatcaatcc tgtgtgaagt gccattcggc ttcatatgcc aactttagct      60
gatgaaacta agtccgtgaa tttggg                                           86

<210> SEQ ID NO 164
<211> LENGTH: 131
<212> TYPE: DNA
<213> ORGANISM: Zea mays

<400> SEQUENCE: 164
gcattgcaag tggtgcgtgc atgcatgttc tgaaatttga tgacgatgca tgcatgggtg      60
gctactagct agctagtcgt ttgatgtcga tctgctgtcc attattctgc agatgtcggt     120
ggagtttcag g                                                          131

<210> SEQ ID NO 165
<211> LENGTH: 101
<212> TYPE: DNA
<213> ORGANISM: Zea mays

<400> SEQUENCE: 165
ccagcatgta aattcatcca agcaacagaa acaaaaactc ggccagggaa ggaaagaccg      60
ccctcccggt attctattaa gaagagaccg aaacatggtc c                         101

<210> SEQ ID NO 166
<211> LENGTH: 107
<212> TYPE: DNA
<213> ORGANISM: Zea mays

<400> SEQUENCE: 166
ttccacggac aagatcaaaa ccataagcag tcacactgct cagggatgtt agggtcctgc      60
attcaaaaga acagcaagta tgatgtcatc acaaaagggt ctaggag                   107

<210> SEQ ID NO 167
<211> LENGTH: 67
<212> TYPE: DNA
<213> ORGANISM: Zea mays

<400> SEQUENCE: 167
ccggctgcgc gttgggggcc aggtagaagg agccgccgtc gacgccgacg tggaactcca      60
cctgggc                                                                67

<210> SEQ ID NO 168
<211> LENGTH: 146
<212> TYPE: DNA
<213> ORGANISM: Zea mays

<400> SEQUENCE: 168
agtcgtcaga attgctcgtt ccagtgcctt acatattaca acaaccaatt attctcctgt      60
cttaaaatcc attccaggac aaaactacag tccataacac atactctgct tctgatttta    120
ctgccgaaca gatccaccga atctcg                                          146
```

```
<210> SEQ ID NO 169
<211> LENGTH: 150
<212> TYPE: DNA
<213> ORGANISM: Zea mays

<400> SEQUENCE: 169
atcgtgactc gtcgcttttt catgtcttca gattttgtcc atctgtcaaa tcatgtggaa      60
aaattggcat atcttcttgt attctcttct gtccttttta atgcctccag cggattaatt     120
tctagctagt tccgttccat tgatctgcct                                      150

<210> SEQ ID NO 170
<211> LENGTH: 66
<212> TYPE: DNA
<213> ORGANISM: Zea mays

<400> SEQUENCE: 170
ctgattctgt ggtggctatg gtcttgaaca tcggtcggga aggccccaaa gttgttccgg      60
tcgaag                                                                66

<210> SEQ ID NO 171
<211> LENGTH: 59
<212> TYPE: DNA
<213> ORGANISM: Zea mays

<400> SEQUENCE: 171
gtggcggtgt gggaacttaa aagtatgact tgacatctag tgcaatccag aagaagcgg       59

<210> SEQ ID NO 172
<211> LENGTH: 101
<212> TYPE: DNA
<213> ORGANISM: Zea mays

<400> SEQUENCE: 172
caggtcgaag gtgtagttgc tgccggggtc caaaggcacc ttgaccttcc tagcatcgtc      60
gccgggtctg ggaggcgggc agagcttcct gagctcggcg g                        101

<210> SEQ ID NO 173
<211> LENGTH: 117
<212> TYPE: DNA
<213> ORGANISM: Zea mays

<400> SEQUENCE: 173
tctacaccaa caaatgcctg ttacattatt catccaaaga acagtaggtg aagggaagaa      60
tatatcttga aaagcttgat aaagttttat agcaaagagt catacaactt cactgaa       117
```

US 10,028,458 B2

YIELD TRAITS FOR MAIZE

RELATED APPLICATION

This application claims the benefit under Title 35, United States Code, § 191(e) of U.S. patent application Ser. No. 12/536,147 filed Aug. 5, 2009 which is further incorporated by reference.

INCORPORATION OF THE SEQUENCE LISTING

A Sequence Listing is contained in the attached file named "72598-US-REG-C-NAT-1_SequenceListing_ST25", which is 77 kilobytes and was filed with U.S. patent application Ser. No. 12/536,147 filed Aug. 5, 2009 for which this application claims the benefit thereof. The Sequence Listing is attached and filed herewith and is incorporated herein by reference.

TECHNICAL FIELD

The presently disclosed subject matter relates to maize, such as maize of the species Zea mays, and methods of breeding the same. More particularly, the presently disclosed subject matter relates to maize lines, such as Zea mays lines, with one or more improved yield traits, and methods for breeding the same, which methods involve in some embodiments genetic marker analysis and/or nucleic acid sequence analysis.

BACKGROUND

A goal of plant breeding is to combine, in a single plant, various desirable traits. For field crops such as corn, these traits can include greater yield and better agronomic quality. However, genetic loci that influence yield and agronomic quality are not always known, and even if known, their contributions to such traits are frequently unclear. Thus, new loci that can positively influence such desirable traits need to be identified and/or the abilities of known loci to do so need to be discovered.

Once discovered, these desirable loci can be selected for as part of a breeding program in order to generate plants that carry desirable traits. An exemplary embodiment of a method for generating such plants includes the transfer by introgression of nucleic acid sequences from plants that have desirable genetic information into plants that do not by crossing the plants using traditional breeding techniques.

Desirable loci can be introgressed into commercially available plant varieties using marker-assisted selection (MAS) or marker-assisted breeding (MAB). MAS and MAB involves the use of one or more of the molecular markers for the identification and selection of those progeny plants that contain one or more loci that encode the desired traits. Such identification and selection can be based on selection of informative markers that are associated with desired traits. MAB can also be used to develop near-isogenic lines (NIL) harboring loci of interest, allowing a more detailed study of the effect each locus can have on a desired trait, and is also an effective method for development of backcross inbred line (BIL) populations.

What are needed, then, are new methods and compositions for genetically analyzing Zea mays varieties and for employing the information obtained for producing new Zea mays plants that have improved traits.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

The presently disclosed subject matter provides methods for introgressing an allele of interest of a locus associated with a yield trait into Zea mays germplasm. In some embodiments, the methods comprise (a) selecting a Zea mays plant that comprises an allele of interest of a locus associated with a yield trait, wherein the locus associated with the yield trait is identifiable by PCR amplification of a Zea mays nucleic acid with a pair of oligonucleotides primers selected from, but not limited to, (i) primer pair 1 represented by a primer comprising SEQ ID NO: 2 and a primer comprising SEQ ID NO: 3; (ii) primer pair 2 represented by a primer comprising SEQ ID NO: 5 and a primer comprising SEQ ID NO: 6; (iii) primer pair 3 represented by a primer comprising SEQ ID NO: 8 and a primer comprising SEQ ID NO: 9; (iv) primer pair 4 represented by a primer comprising SEQ ID NO: 11 and a primer comprising SEQ ID NO: 12; (v) primer pair 5 represented by a primer comprising SEQ ID NO: 14 and a primer comprising SEQ ID NO: 15; (vi) primer pair 6 represented by a primer comprising SEQ ID NO: 17 and a primer comprising SEQ ID NO: 18; (vii) primer pair 7 represented by a primer comprising SEQ ID NO: 20 and a primer comprising SEQ ID NO: 21; (viii) primer pair 8 represented by a primer comprising SEQ ID NO: 23 and a primer comprising SEQ ID NO: 24; (ix) primer pair 9 represented by a primer comprising SEQ ID NO: 26 and a primer comprising SEQ ID NO: 27; (x) primer pair 10 represented by a primer comprising SEQ ID NO: 29 and a primer comprising SEQ ID NO: 30; (xi) primer pair 11 represented by a primer comprising SEQ ID NO: 32 and a primer comprising SEQ ID NO: 33; (xii) primer pair 12 represented by a primer comprising SEQ ID NO: 35 and a primer comprising SEQ ID NO: 36; (xiii) primer pair 13 represented by a primer comprising SEQ ID NO: 38 and a primer comprising SEQ ID NO: 39; (xiv) primer pair 14 represented by a primer comprising SEQ ID NO: 41 and a primer comprising SEQ ID NO: 42; (xv) primer pair 15 represented by a primer comprising SEQ ID NO: 44 and a primer comprising SEQ ID NO: 45; (xvi) primer pair 16 represented by a primer comprising SEQ ID NO: 47 and a primer comprising SEQ ID NO: 48; (xvii) primer pair 17 represented by a primer comprising SEQ ID NO: 50 and a primer comprising SEQ ID NO: 51; (xviii) primer pair 18 represented by a primer comprising SEQ ID NO: 53 and a primer comprising SEQ ID NO: 54; (xix) primer pair 19 represented by a primer comprising SEQ ID NO: 56 and a primer comprising SEQ ID NO: 57; (xx) primer pair 20 represented by a primer comprising SEQ ID NO: 59 and a primer comprising SEQ ID NO: 60; (xxi) primer pair 21 represented by a primer comprising SEQ ID NO: 62 and a primer comprising SEQ ID NO: 63; and (xxii) primer pair 22 represented by a primer comprising SEQ ID NO: 65 and a primer comprising SEQ ID NO: 66; and (b) introgressing the allele of interest into Zea mays germplasm that lacks the allele. In some embodiments, the allele of interest comprises a nucleotide sequence as set forth in any of SEQ ID NOs: 67-132. In some embodiments, the yield trait comprises a starch trait, a protein trait, an oil trait, an ethanol production trait, or a combination thereof. In some embodiments, the allele of interest is a favorable allele that positively correlates with an improved starch-, oil-, and/or ethanol production-associated trait or that negatively correlates with an improved protein-associated trait.

The presently disclosed subject matter also provides methods for identifying a Zea mays plant comprising at least one allele associated with improved yield. In some embodiments, the methods comprise (a) genotyping at least one Zea mays plant with at least one nucleic acid marker selected from, but not limited to, SEQ ID NOs: 1, 4, 7, 10, 13, 16, 19, 22, 25, 28, 31, 34, 37, 40, 43, 46, 49, 52, 55, 58, 61, 64, and 111-173; and (b) selecting at least one Zea mays plant comprising an allele of at least one of the at least one nucleic acid marker that is associated with improved yield. In some embodiments, the allele associated with improved yield comprises a nucleotide sequence as set forth in any of SEQ ID NOs: 1, 4, 7, 10, 13, 16, 19, 22, 25, 28, 31, 34, 37, 40, 43, 46, 49, 52, 55, 58, 61, 64, 67-132. In some embodiments, the allele associated with improved yield is a favorable allele that positively correlates with an improved starch-, oil-, and/or ethanol production-associated trait or that negatively correlates with an improved protein-associated trait.

In some embodiments of the presently disclosed methods, the favorable allele comprises a nucleotide sequence comprising (i) an A at nucleotide position 701 of SEQ ID NO: 1 or at nucleotide position 30 of SEQ ID NO: 111; (ii) a G at nucleotide position 498 of SEQ ID NO: 4 or at nucleotide position 23 of SEQ ID NO: 112; (iii) a T at nucleotide position 587 of SEQ ID NO: 7 or at nucleotide position 33 of SEQ ID NO: 113; (iv) a G at nucleotide position 708 of SEQ ID NO: 10 or at nucleotide position 76 of SEQ ID NO: 114; (v) a C at nucleotide position 140 of SEQ ID NO: 13 or at nucleotide position 58 of SEQ ID NO: 115; (vi) an A at nucleotide position 116 of SEQ ID NO: 16 or at nucleotide position 33 of SEQ ID NO: 116; (vii) an A at nucleotide position 269 of SEQ ID NO: 19 or at nucleotide position 32 of SEQ ID NO: 117; (viii) an A at nucleotide position 280 of SEQ ID NO: 22 or at nucleotide position 23 of SEQ ID NO: 118; (ix) a T at nucleotide position 374 of SEQ ID NO: 25 or at nucleotide position 46 of SEQ ID NO: 119; (x) a G at nucleotide position 236 of SEQ ID NO: 28 or at nucleotide position 41 of SEQ ID NO: 120; (xi) a G at nucleotide position 605 of SEQ ID NO: 31 or at nucleotide position 32 of SEQ ID NO: 121; (xii) a CGA trinucleotide sequence at nucleotide positions 349-351 of SEQ ID NO: 34 or at nucleotide positions 48-50 of SEQ ID NO: 122; (xiii) a C at nucleotide position 389 of SEQ ID NO: 37 or at nucleotide position 45 of SEQ ID NO: 123; (xiv) a G at nucleotide position 66 of SEQ ID NO: 40 or at nucleotide position 44 of SEQ ID NO: 124; (xv) a T at nucleotide position 278 of SEQ ID NO: 43 or at nucleotide position 48 of SEQ ID NO: 125; (xvi) a G at nucleotide position 463 of SEQ ID NO: 46 or at nucleotide position 20 of SEQ ID NO: 126; (xvii) a G at nucleotide position 510 of SEQ ID NO: 49 or at nucleotide position 126 of SEQ ID NO: 127; (xviii) a G at nucleotide position 134 of SEQ ID NO: 52 or at nucleotide position 126 of SEQ ID NO: 128; (xix) an A at nucleotide position 367 of SEQ ID NO: 55 or at nucleotide position 32 of SEQ ID NO: 129; (xx) a G at nucleotide position 119 of SEQ ID NO: 58 or at nucleotide position 23 of SEQ ID NO: 130; (xxi) a G at nucleotide position 347 of SEQ ID NO: 61 or at nucleotide position 53 of SEQ ID NO: 131; or (xxii) and an A at nucleotide position 356 of SEQ ID NO: 64 or at nucleotide position 43 of SEQ ID NO: 132.

The presently disclosed subject matter also provides improved Zea mays plants produced by the presently disclosed methods, as well as parts, seeds, progeny, and tissue cultures thereof. In some embodiments, the part, seed, progeny, or tissue culture thereof comprises at least one allele of interest for each of at least two distinct loci associated with yield traits, and further wherein the improved plant or the part, seed, progeny, or tissue culture thereof comprises (a) a desired starch allele and a desired ethanol production allele; and/or (b) a desired starch allele and a desired protein allele. In some embodiments, the improved Zea mays plant or the part, seed, progeny, or tissue culture thereof, comprises a desired allele for increased starch and a desired allele for decreased protein.

The presently disclosed subject matter also provides elite Zea mays plants produced from the improved Zea mays plants disclosed herein.

The presently disclosed subject matter also provides biomass produced from the improved Zea mays plants disclosed herein, or from a progeny plant thereof, or from a part, seed, or tissue culture thereof.

The presently disclosed subject matter also provides isolated and purified genetic markers associated with a yield trait in Zea mays. In some embodiments, the isolated and purified genetic marker (i) comprises a nucleotide sequence as set forth in any of SEQ ID NOs: 1-173, or the reverse complement thereof, or an informative fragment thereof; and/or (ii) comprises a nucleotide sequence of an amplification product or an informative fragment thereof from a nucleic acid sample isolated from a Zea mays plant, wherein the amplification product is produced by amplifying a Zea mays nucleic acid using a pair of oligonucleotide primers selected from, but not limited to, SEQ ID NOs: 2 and 3; SEQ ID NOs: 5 and 6; SEQ ID SEQ ID NOs: 8 and 9; SEQ ID NOs: 11 and 12; SEQ ID NOs: 14 and 15; SEQ ID NOs: 17 and 18; SEQ ID NOs: 20 and 21; SEQ ID NOs: 23 and 24; SEQ ID NOs: 26 and 27; or SEQ ID NOs: 29 and 30; SEQ ID NOs: 32 and 33; SEQ ID NOs: 35 and 36; SEQ ID NOs: 38 and 39; SEQ ID NOs: 41 and 42; SEQ ID NOs: 44 and 45; SEQ ID NOs: 47 and 48; SEQ ID NOs: 50 and 51; SEQ ID NOs: 53 and 54; SEQ ID NOs: 56 and 57; SEQ ID NOs: 59 and 60; SEQ ID NOs: 62 and 63; and SEQ ID NOs: 65 and 66. In some embodiments, the isolated and purified genetic marker permits identification of a nucleotide in the genome of a Zea mays plant that corresponds to the nucleotide present at any of nucleotide position 30 of SEQ ID NO: 111; nucleotide position 23 of SEQ ID NO: 112; nucleotide position 33 of SEQ ID NO: 113; nucleotide position 76 of SEQ ID NO: 114; nucleotide position 58 of SEQ ID NO: 115; nucleotide position 33 of SEQ ID NO: 116; nucleotide position 32 of SEQ ID NO: 117; nucleotide position 23 of SEQ ID NO: 118; nucleotide position 46 of SEQ ID NO: 119; nucleotide position 41 of SEQ ID NO: 120; nucleotide position 32 of SEQ ID NO: 121; nucleotide positions 48-50 of SEQ ID NO: 122; nucleotide position 45 of SEQ ID NO: 123; nucleotide position 44 of SEQ ID NO: 124; nucleotide position 48 of SEQ ID NO: 125; nucleotide position 20 of SEQ ID NO: 126; nucleotide position 126 of SEQ ID NO: 127; nucleotide position 126 of SEQ ID NO: 128; nucleotide position 32 of SEQ ID NO: 129; nucleotide position 23 of SEQ ID NO: 130; nucleotide position 53 of SEQ ID NO: 131; and nucleotide position 43 of SEQ ID NO: 132. In some embodiments, the isolated and purified genetic marker further comprises a detectable moiety.

The presently disclosed subject matter also provides compositions comprising amplification primer pairs capable of amplifying a *Zea mays* nucleic acid to generate *Zea mays* marker amplicons. In some embodiments, the *Zea mays* marker amplicons correspond to any of SEQ ID NOs: 1, 4, 7, 10, 13, 16, 19, 22, 25, 28, 31, 34, 37, 40, 43, 46, 49, 52, 55, 58, 61, 64, and 111-173.

Thus, it is an object of the presently disclosed subject matter to provide methods for conveying one or more yield traits into maize germplasm.

An object of the presently disclosed subject matter having been stated hereinabove, and which is achieved in whole or in part by the presently disclosed subject matter, other objects will become evident as the description proceeds when taken in connection with the accompanying Figures as best described herein below.

BRIEF DESCRIPTION OF THE SEQUENCE LISTING

Figure 1:
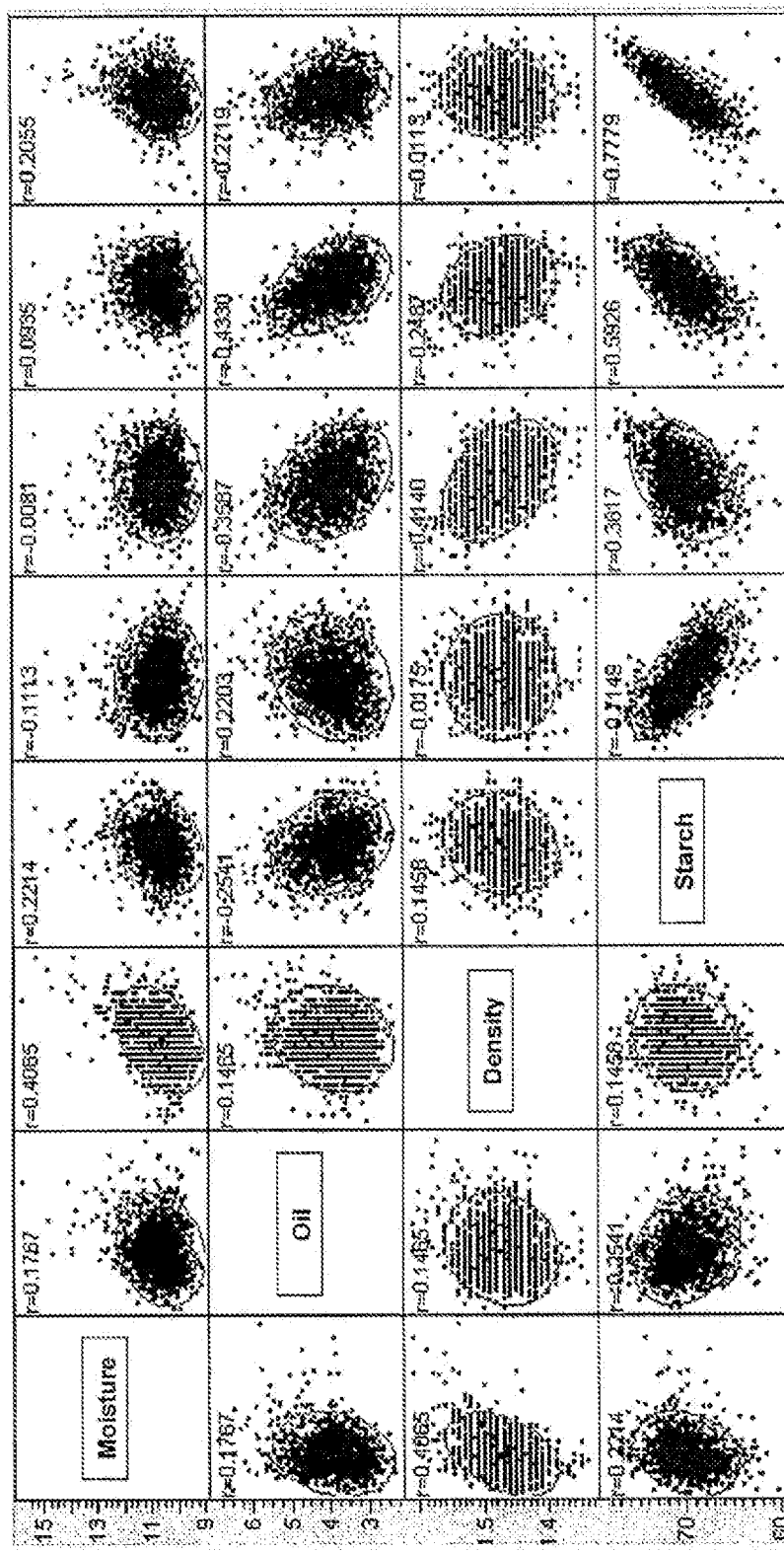
FIG. 1 shows a scatter plot correlation of yield (e.g., starch, protein, oil, and/or ethanol production) traits from the inbred platform. The numbers in the top left corner of each box present pairwise correlations between the traits (e.g., a positive correlation (r=0.2203) between oil (Oil_db) and protein (PRTNP) traits and a negative correlation (r=−0.7667) between protein (PRTNP) and digestibility at 72 hours (DGST 72)).
Figure 1:
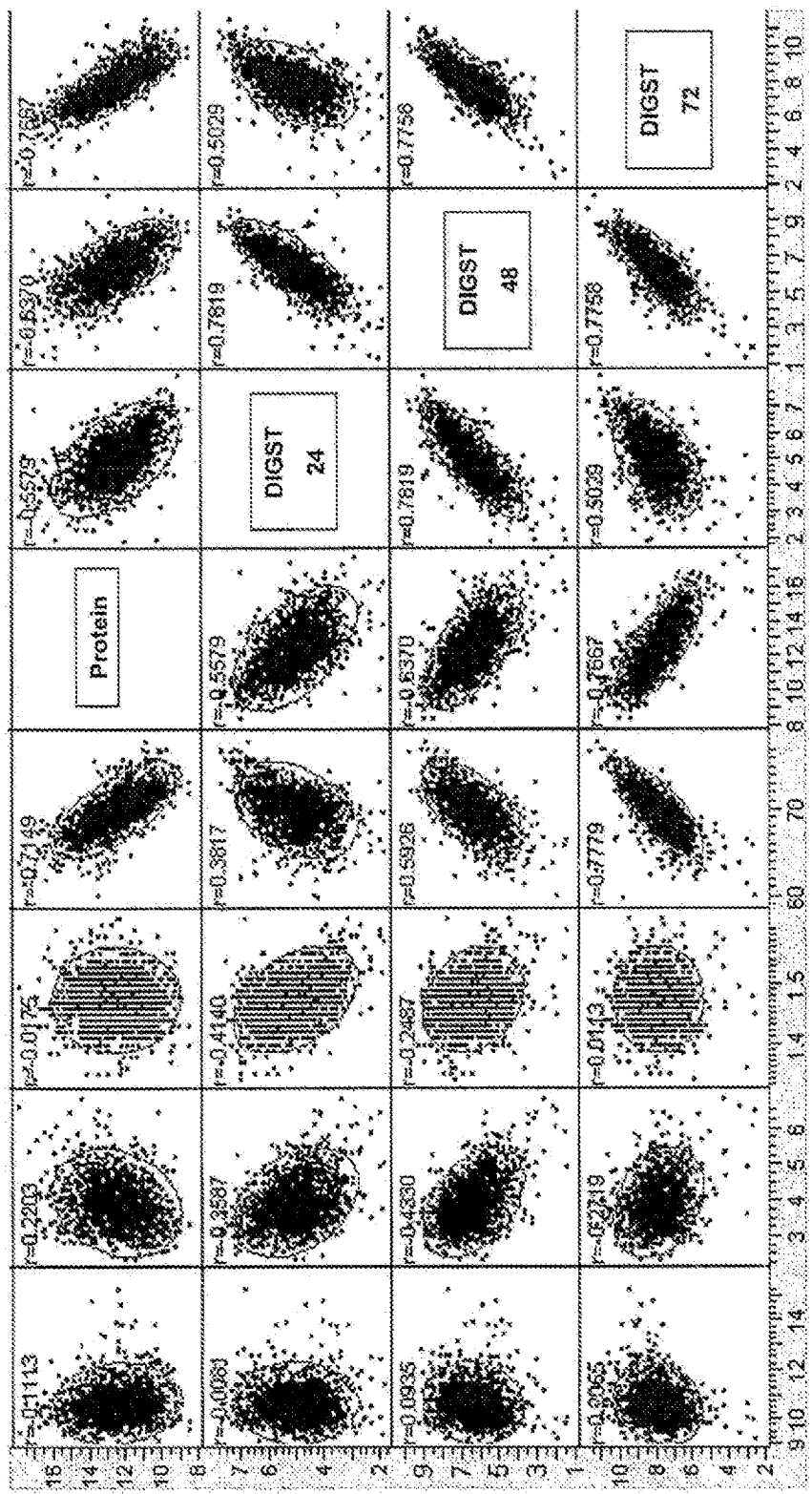

SEQ ID NO: 1 is a nucleotide sequence that is associated with the yield loci MTL1, MTPL1, and MTSL1, a subsequence of which (SEQ ID NO: 111) can be amplified from chromosome 5 of the *Zea mays* genome using the polymerase chain reaction with amplification primers comprising the nucleotide sequences set forth in SEQ ID NOs: 2 and 3.

SEQ ID NO: 4 is a nucleotide sequence that is associated with the yield loci MTL2 and MTSL2, a subsequence of which (SEQ ID NO: 112) can be amplified from chromosome 5 of the *Zea mays* genome using the polymerase chain reaction with amplification primers comprising the nucleotide sequences set forth in SEQ ID NOs: 5 and 6.

SEQ ID NO: 7 is a nucleotide sequence that is associated with the yield loci MTL3 and MTSL3, a subsequence of which (SEQ ID NO: 113) can be amplified from chromosome 5 of the *Zea mays* genome using the polymerase chain reaction with amplification primers comprising the nucleotide sequences set forth in SEQ ID NOs: 8 and 9.

SEQ ID NO: 10 is a nucleotide sequence that is associated with the yield loci MTL4, MTPL2, and MTSL4, a subsequence of which (SEQ ID NO: 114) can be amplified from chromosome 2 of the *Zea mays* genome using the polymerase chain reaction with amplification primers comprising the nucleotide sequences set forth in SEQ ID NOs: 11 and 12.

SEQ ID NO: 13 is a nucleotide sequence that is associated with the yield locus MTL5, a subsequence of which (SEQ ID NO: 115) can be amplified from chromosome 2 of the *Zea mays* genome using the polymerase chain reaction with amplification primers comprising the nucleotide sequences set forth in SEQ ID NOs: 14 and 15.

SEQ ID NO: 16 is a nucleotide sequence that is associated with the yield locus MTL6, a subsequence of which (SEQ ID NO: 116) can be amplified from chromosome 5 of the *Zea mays* genome using the polymerase chain reaction with amplification primers comprising the nucleotide sequences set forth in SEQ ID NOs: 17 and 18.

SEQ ID NO: 19 is a nucleotide sequence that is associated with the yield loci MTL7 and MTPL3, a subsequence of which (SEQ ID NO: 117) can be amplified from chromosome 7 of the *Zea mays* genome using the polymerase chain reaction with amplification primers comprising the nucleotide sequences set forth in SEQ ID NOs: 20 and 21.

SEQ ID NO: 22 is a nucleotide sequence that is associated with the yield loci MTL8 and MTPL4, a subsequence of which (SEQ ID NO: 118) can be amplified from chromosome 5 of the *Zea mays* genome using the polymerase chain reaction with amplification primers comprising the nucleotide sequences set forth in SEQ ID NOs: 23 and 24.

SEQ ID NO: 25 is a nucleotide sequence that is associated with the yield locus MTL9, a subsequence of which (SEQ ID NO: 119) can be amplified from chromosome 5 of the *Zea mays* genome using the polymerase chain reaction with amplification primers comprising the nucleotide sequences set forth in SEQ ID NOs: 26 and 27.

SEQ ID NO: 28 is a nucleotide sequence that is associated with the yield loci MTL10 and MTOL3, a subsequence of which (SEQ ID NO: 120) can be amplified from chromosome 1 of the *Zea mays* genome using the polymerase chain reaction with amplification primers comprising the nucleotide sequences set forth in SEQ ID NOs: 29 and 30.

SEQ ID NO: 31 is a nucleotide sequence that is associated with the yield locus MTL11, a subsequence of which (SEQ ID NO: 121) can be amplified from chromosome 2 of the *Zea mays* genome using the polymerase chain reaction with amplification primers comprising the nucleotide sequences set forth in SEQ ID NOs: 32 and 33.

SEQ ID NO: 34 is a nucleotide sequence that is associated with the yield locus MTL12, a subsequence of which (SEQ ID NO: 122) can be amplified from chromosome 10 of the *Zea mays* genome using the polymerase chain reaction with amplification primers comprising the nucleotide sequences set forth in SEQ ID NOs: 35 and 36.

SEQ ID NO: 37 is a nucleotide sequence that is associated with the yield loci MTL13 and MTSL5, a subsequence of which (SEQ ID NO: 123) can be amplified from chromosome 8 of the *Zea mays* genome using the polymerase chain reaction with amplification primers comprising the nucleotide sequences set forth in SEQ ID NOs: 38 and 39.

SEQ ID NO: 40 is a nucleotide sequence that is associated with the yield loci MTL14 and MTPL9, a subsequence of which (SEQ ID NO: 124) can be amplified from chromosome 1 of the *Zea mays* genome using the polymerase chain reaction with amplification primers comprising the nucleotide sequences set forth in SEQ ID NOs: 41 and 42.

SEQ ID NO: 43 is a nucleotide sequence that is associated with the yield locus MTL15, a subsequence of which (SEQ ID NO: 125) can be amplified from chromosome 5 of the *Zea mays* genome using the polymerase chain reaction with amplification primers comprising the nucleotide sequences set forth in SEQ ID NOs: 44 and 45.

SEQ ID NO: 46 is a nucleotide sequence that is associated with the yield locus MTL16, a subsequence of which (SEQ ID NO: 126) can be amplified from chromosome 1 of the *Zea mays* genome using the polymerase chain reaction with amplification primers comprising the nucleotide sequences set forth in SEQ ID NOs: 47 and 48.

SEQ ID NO: 49 is a nucleotide sequence that is associated with the yield loci MTL17 and MTPL8, a subsequence of which (SEQ ID NO: 127) can be amplified from chromosome 5 of the *Zea mays* genome using the polymerase chain reaction with amplification primers comprising the nucleotide sequences set forth in SEQ ID NOs: 50 and 51.

SEQ ID NO: 52 is a nucleotide sequence that is associated with the yield loci MTL18 and MTPL7, a subsequence of which (SEQ ID NO: 128) can be amplified from chromosome 10 of the *Zea mays* genome using the polymerase chain reaction with amplification primers comprising the nucleotide sequences set forth in SEQ ID NOs: 53 and 54.

SEQ ID NO: 55 is a nucleotide sequence that is associated with the yield locus MTOL1, a subsequence of which (SEQ ID NO: 129) can be amplified from chromosome 1 of the *Zea mays* genome using the polymerase chain reaction with amplification primers comprising the nucleotide sequences set forth in SEQ ID NOs: 56 and 57.

SEQ ID NO: 58 is a nucleotide sequence that is associated with the yield locus MTPL5, a subsequence of which (SEQ ID NO: 130) can be amplified from chromosome 4 of the *Zea mays* genome using the polymerase chain reaction with amplification primers comprising the nucleotide sequences set forth in SEQ ID NOs: 59 and 60.

SEQ ID NO: 61 is a nucleotide sequence that is associated with the yield loci MTSL6 and MTPL10, a subsequence of which (SEQ ID NO: 131) can be amplified from chromosome 6 of the *Zea mays* genome using the polymerase chain reaction with amplification primers comprising the nucleotide sequences set forth in SEQ ID NOs: 62 and 63.

SEQ ID NO: 64 is a nucleotide sequence that is associated with the yield loci MTPL6 and MTOL2, a subsequence of which (SEQ ID NO: 132) can be amplified from chromosome 7 of the *Zea mays* genome using the polymerase chain reaction with amplification primers comprising the nucleotide sequences set forth in SEQ ID NOs: 65 and 66.

SEQ ID NOs: 67-110 are nucleotide sequences of oligonucleotide probes associated with MTL 1-18, MTPL 1-9, MTSL 1-6, and MTOL 1-3 that can be employed to distinguish between alternative alleles of these loci as set forth in Table 1 below.

TABLE 1

SEQ ID NOs. for Assay Oligonucleotides

| Locus Assayed | Nucleotide Assayed | Allele Detected: Primer SEQ ID NO. |
|---|---|---|
| MTL1/MTPL1/MTSL1 (SEQ ID NO: 1) | 701 | A: SEQ ID NO: 67 G: SEQ ID NO: 68 |
| MTL2/MTSL2 (SEQ ID NO: 4) | 498 | G: SEQ ID NO: 69 A: SEQ ID NO: 70 |
| MTL3/MTSL3 (SEQ ID NO: 7) | 587 | T: SEQ ID NO: 71 C: SEQ ID NO: 72 |
| MTL4/MTPL2/MTSL4 (SEQ ID NO: 10) | 708 | G: SEQ ID NO: 73 A: SEQ ID NO: 74 |
| MTL5 (SEQ ID NO: 13) | 140 | C: SEQ ID NO: 75 T: SEQ ID NO: 76 |
| MTL6 (SEQ ID NO: 16) | 116 | A: SEQ ID NO: 77 G: SEQ ID NO: 78 |
| MTL7/MTPL3 (SEQ ID NO: 19) | 269 | A: SEQ ID NO: 79 G: SEQ ID NO: 80 |
| MTL8/MTPL4 (SEQ ID NO: 22) | 280 | A: SEQ ID NO: 81 G: SEQ ID NO: 82 |
| MTL9 (SEQ ID NO: 25) | 374 | T: SEQ ID NO: 83 G: SEQ ID NO: 84 |
| MTL10/MTOL3 (SEQ ID NO: 28) | 236 | G: SEQ ID NO: 85 A: SEQ ID NO: 86 |

TABLE 1-continued

SEQ ID NOs. for Assay Oligonucleotides

| Locus Assayed | Nucleotide Assayed | Allele Detected: Primer SEQ ID NO. |
|---|---|---|
| MTL11 (SEQ ID NO: 31) | 605 | G: SEQ ID NO: 87 A: SEQ ID NO: 88 |
| MTL12 (SEQ ID NO: 34) | 349 | C: SEQ ID NO: 89 T: SEQ ID NO: 90 |
| MTL13/MTSL5 (SEQ ID NO: 37) | 389 | C: SEQ ID NO: 91 T: SEQ ID NO: 92 |
| MTL14/MTPL9 (SEQ ID NO: 40) | 66 | G: SEQ ID NO: 93 A: SEQ ID NO: 94 |
| MTL15 (SEQ ID NO: 43) | 278 | T: SEQ ID NO: 95 C: SEQ ID NO: 96 |
| MTL16 (SEQ ID NO: 46) | 463 | G: SEQ ID NO: 97 A: SEQ ID NO: 98 |
| MTL17/MTPL8 (SEQ ID NO: 49) | 510 | G: SEQ ID NO: 99 A: SEQ ID NO: 100 |
| MTL18/MTPL7 (SEQ ID NO: 52) | 134 | G: SEQ ID NO: 101 T: SEQ ID NO: 102 |
| MTOL1 (SEQ ID NO: 55) | 367 | A: SEQ ID NO: 103 G: SEQ ID NO: 104 |
| MTPL5 (SEQ ID NO: 58) | 119 | G: SEQ ID NO: 105 C: SEQ ID NO: 106 |
| MTSL6/MTPL10 (SEQ ID NO: 61) | 347 | G: SEQ ID NO: 107 T: SEQ ID NO: 108 |
| MTPL6/MTOL2 (SEQ ID NO: 64) | 356 | A: SEQ ID NO: 109 G: SEQ ID NO: 110 |

SEQ ID NOs: 111-132 are nucleotide sequences associated with MTL 1-18, MTPL 1-9, MTSL 1-6, and/or MTOL 1-3 that can be amplified from *Zea mays* nucleic acids using sets of oligonucleotide primers as set forth in Table 2 below.

TABLE 2

SEQ ID NOs. for *Zea mays* Sequences that can be Amplified by PCR Primers and Resultant Amplicon Sizes

| SEQ ID NO: | Exemplary Amplification Primer SEQ ID NOs: | Amplicon Size (bp) |
|---|---|---|
| 111 | 2 and 3 | 106 |
| 112 | 5 and 6 | 136 |
| 113 | 8 and 9 | 160 |
| 114 | 11 and 12 | 122 |
| 115 | 14 and 15 | 120 or 121 |
| 116 | 17 and 18 | 84 |
| 117 | 20 and 21 | 74 |
| 118 | 23 and 24 | 46 |
| 119 | 26 and 27 | 74 |
| 120 | 29 and 30 | 87 |
| 121 | 32 and 33 | 86 |
| 122 | 35 and 34 | 141 or 144 |
| 123 | 38 and 39 | 101 |
| 124 | 41 and 42 | 107 |
| 125 | 44 and 45 | 227 |
| 126 | 47 and 48 | 67 |
| 127 | 50 and 51 | 146 |
| 128 | 53 and 54 | 153 |
| 129 | 56 and 57 | 66 |
| 130 | 59 and 60 | 59 |
| 131 | 62 and 63 | 107 |
| 132 | 65 and 66 | 117 |

SEQ ID NOs. 133-152 are *Zea mays* genomic DNA sequences present in the GENBANK® database that correspond to the nucleotide sequences of SEQ ID NOs: 1-124 and 126-132 as set forth in Table 3 below. Subsequences of these sequences can also be amplified using primer pairs to yield amplicons as also set forth in Table

TABLE 3

GENBANK ® Database Sequences that Correspond
to SEQ ID NOs: 1-124 and 126-132

| SEQ ID NO: | GENBANK ® Accession No. | Nucleotide Positions | Exemplary Amplification Primer SEQ ID NOs: | Amplicon SEQ ID NO. | Amplicon Size (bp) |
|---|---|---|---|---|---|
| 133 | AC209208.3 | 49,337 to 50,164 | 2 and 3 | 153 | 106 |
| 134 | AC206616.3 | 43,103 to 43,821 | 5 and 6 | 154 | 133 |
| 134 | AC206616.3 | 43,103 to 43,821 | 8 and 9 | 155 | 156 |
| 135 | AC204769.3 | 50,033 to 50,828 | 11 and 12 | 156 | 121 |
| 136 | AC214243.4 | 99,595 to 100,453 | 14 and 15 | 157 | 120 |
| 137 | AC185458.4 | 56,729 to 57,382 | 17 and 18 | 158 | 84 |
| 138 | AC211735.3 | 113,858 to 114,950 | 20 and 21 | 159 | 74 |
| 139 | AC212758.3 | 121,592 to 123,221 | 23 and 24 | 160 | 46 |
| 140 | AC203779.6 | 159,378 to 160,234 | 26 and 27 | 161 | 74 |
| 141 | AC196146.3 | 4367 to 4883 | 29 and 30 | 162 | 87 |
| 142 | AC214129.2 | 106,354 to 107,115 | 32 and 33 | 163 | 86 |
| 143 | AC183312.5 | 2608 to 3395 | 35 and 34 | 164 | 131 |
| 144 | AC194834.3 | 116,067 to 116,863 | 38 and 39 | 165 | 101 |
| 145 | AC197472.2 | 66,678 to 67,232 | 41 and 42 | 166 | 107 |
| 146 | AC197469.3 | 173,922 to 174,662 | 47 and 48 | 167 | 67 |
| 147 | AC210263.4 | 181,778 to 182,591 | 50 and 51 | 168 | 146 |
| 148 | AC203332.3 | 120,187 to 121,112 | 53 and 54 | 169 | 150 |
| 149 | AC198211.4 | 85,472 to 86,260 | 56 and 57 | 170 | 66 |
| 150 | AC191759.3 | 147,402 to 148,055 | 59 and 60 | 171 | 59 |
| 151 | AC204581.3 | 166,218 to 166,660 | 62 and 63 | 172 | 101 |
| 152 | AC212580.4 | 100,621 to 101,358 | 65 and 66 | 173 | 117 |

SEQ ID NOs: 133-152 have been added to the GENBANK® database by the Genome Sequencing Center, Washington University School of Medicine, St. Louis, Mo., United States of America. As set forth in the annotations to these database entries, the sequences were part of an effort by The Maize Sequencing Consortium to sequence the genome of *Zea mays*. Currently, the sequencing effort has not been completed, and various portions of the *Zea mays* genome remain unsequenced.

As can be seen in the above Tables, certain of the sequences of SEQ ID NOs: 1-173 are related to each other. By way of example, SEQ ID NO: 1 is a nucleotide sequence from *Zea mays*. A subsequence of SEQ ID NO: 1 can be amplified in an amplification reaction (e.g., a PCR) using oligonucleotide primers having the sequences set forth in SEQ ID NOs: 2 and 3 to yield an amplicon that in some embodiments has a nucleotide sequence as set forth in SEQ ID NO: 111, which has a size of 106 basepairs (bp). At position 701 of SEQ ID NO: 1 there is an SNP, and the specific nucleotide that is present in any nucleic acid sample at this position can be determined using oligonucleotides that have the sequences set forth in SEQ ID NOs: 67 and 68.

Additionally, GENBANK® Accession No. AC209208.3 includes a subsequence (i.e., nucleotides 49,337 to 50,164; SEQ ID NO: 133) that itself (or its reverse complement) is highly similar to SEQ ID NO: 1 and thus is present at the same locus from which SEQ ID NO: 1 is derived. The differences between the two sequences (which can be identified using a BLAST algorithm, a ClustalX algorithm, or any other appropriate method of analysis) can be attributable to normal variation within *Zea mays* populations. A subsequence of SEQ ID NO: 133 can also be amplified in an amplification reaction (e.g., a PCR) using oligonucleotide primers having the sequences set forth in SEQ ID NOs: 2 and 3 to yield an amplicon which in some embodiments has a nucleotide sequence as set forth in SEQ ID NO: 153, which has a size of 106 basepairs (bp). Oligonucleotides with the sequences set forth in SEQ ID NOs: 67 and 68 can also be used to assay the base that is present at the position that corresponds to position 701 of SEQ ID NO: 1, which in this case is also position 701 of SEQ ID NO: 133 and is position 30 of SEQ ID NO: 153.

For SEQ ID NOs: 134-173, similar interrelationships exist with SEQ ID NOs: 4-42, 46-66, 69-110, and 112-132 as are described hereinabove, and would be identifiable by one of ordinary skill in the art using routine sequence analysis techniques. It is noted that with respect to SEQ ID NOs: 43-45, the complete nucleotide sequence of a genomic clone that includes the full length sequence that corresponds to these sequences (as well as to SEQ ID NO: 125) has not been yet been added to the GENBANK® database by The Maize Sequencing Consortium. As such, a sequence from the GENBANK® database that can be amplified using primers comprising SEQ ID NOs: 44 and 45 is not included in the Tables above. It is further noted, however, that nucleotides 10,855-10,962 and 103,384-103,629 of GENBANK® Accession No. AC204604.3 correspond to subsequences of SEQ ID NOs: 43 and 125.

DETAILED DESCRIPTION

I. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. For example, the phrase "a marker" refers to one or more markers. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus; in diploids a single allele at each locus is inherited by a progeny individual separately from each parent. The term "allele" thus refers to any of one or more alternative forms of a nucleotide sequence of a gene, all of which relate to at least one trait or characteristic, in a diploid cell. Two alleles of a given gene occupy corresponding loci on a pair of homologous chromosomes, although one of ordinary skill in the art understands that the alleles in any particular individual do not necessarily represent all of the alleles that are present in the species. Since the presently disclosed subject matter relates in some embodiments to MTLs (i.e., genomic regions that can comprise one or more genes or regulatory sequences), it is in some instances more accurate to refer to a "haplotype" (i.e., an allele of a chromosomal segment) instead of "allele". However, in such instances, the term "allele" should be understood to comprise the term "haplotype".

As used herein, the phrase "associated with" refers to a recognizable and/or assayable relationship between two entities. For example, the phrase "associated with an ethanol production trait" refers to a trait, locus, MTL gene, allele, marker, phenotype, etc., or the expression thereof, the presence or absence of which can influence an extent, degree, and/or rate at which a plant that has the ethanol production trait produces ethanol. Similarly, the phrase "associated with a starch trait" refers to a trait, locus, MTL gene, allele, marker, phenotype, etc., or the expression thereof, the presence or absence of which can influence the production of starch in a plant.

As used herein, the term "backcross", and grammatical variants thereof, refers to a process in which a breeder crosses a progeny individual back to one of its parents: for example, a first generation F1 with one of the parental genotypes of the F1 individual. In some embodiments, a backcross is performed repeatedly, with a progeny individual of each successive backcross generation being itself backcrossed to the same parental genotype.

As used herein, the term "chromosome" is used in its art-recognized meaning of the self-replicating genetic structure in the cellular nucleus containing the cellular DNA and bearing in its nucleotide sequence the linear array of genes. The Zea mays chromosome numbers disclosed herein refer to those as set forth in Perin et al., 2002, which relates to a reference nomenclature system adopted by L'institut National da la Recherché Agronomique (INRA; Paris, France).

As used herein, the phrase "consensus sequence" refers to a sequence of DNA built to identify nucleotide differences (e.g., SNP and Indel polymorphisms) in alleles at a locus. A consensus sequence can be either strand of DNA at the locus and states the nucleotide(s) at one or more positions (e.g., at one or more SNPs and/or at one or more Indels) in the locus.

In some embodiments, a consensus sequence is used to design primers and probes for detecting polymorphisms in the locus.

As used herein, the terms "cultivar" and "variety" refer to a group of similar plants that by structural or genetic features and/or performance can be distinguished from other varieties within the same species.

As used herein, the phrase "elite line" refers to any line that is substantially homozygous and has resulted from breeding and selection for superior agronomic performance.

As used herein, the term "gene" refers to a hereditary unit including a sequence of DNA that occupies a specific location on a chromosome and that contains the genetic instruction for a particular characteristics or trait in an organism.

As used herein, the phrase "genetic map" refers to the ordered list of loci usually relevant to position on a chromosome.

As used herein, the phrase "genetic marker" refers to a nucleic acid sequence (e.g., a polymorphic nucleic acid sequence) that has been identified as associated with a locus or allele of interest and that is indicative of the presence or absence of the locus or allele of interest in a cell or organism. Examples of genetic markers include, but are not limited to genes, DNA or RNA-derived sequences, promoters, any untranslated regions of a gene, microRNAs, siRNAs, QTLs, transgenes, mRNAs, ds RNAs, transcriptional profiles, and methylation patterns.

As used herein, the term "genotype" refers to the genetic component of a phenotype of interest, a plurality of phenotypes of interest, or an entire cell or organism. Genotypes can be indirectly characterized using markers and/or directly characterized by nucleic acid sequencing.

As used herein, the term "heterozygous" refers to a genetic condition that exists in a cell or an organism when different alleles reside at corresponding loci on homologous chromosomes. As used herein, the term "homozygous" refers to a genetic condition existing when identical alleles reside at corresponding loci on homologous chromosomes. It is noted that both of these terms can refer to single nucleotide positions, multiple nucleotide positions, whether contiguous or not, or entire loci on homologous chromosomes.

As used herein, the term "hybrid" refers to a seed and the plant the seed develops into that result from crossing at least two genetically different plant parents.

As used herein, the term "hybrid" when used in the context of nucleic acids, refers to a double-stranded nucleic acid molecule, or duplex, formed by hydrogen bonding between complementary nucleotide bases. The terms "hybridize" and "anneal" refer to the process by which single strands of nucleic acid sequences form double-helical segments through hydrogen bonding between complementary bases.

As used herein, the phrase "ILLUMINA® GOLDENGATE® Assay" refers to a high throughput genotyping assay sold by Illumina Inc. of San Diego, Calif., United States of America that can generate SNP-specific PCR products. This assay is described in detail at the website of Illumina Inc. and in Fan et al., 2006.

As used herein, the term "improved", and grammatical variants thereof, refers to a plant or a part, progeny, or tissue culture thereof, that as a consequence of having (or lacking) a particular yield associated allele (such as, but not limited to those yield associated alleles disclosed herein) is characterized by a higher or lower content of a yield associated trait, depending on whether the higher or lower content is desired for a particular purpose.

As used herein, the term "inbred" refers to a substantially homozygous individual or line. It is noted that the term can refer to individuals or lines that are substantially homozygous throughout their entire genomes or that are substantially homozygous with respect to subsequences of their genomes that are of particular interest.

As used herein, the phrase "immediately adjacent", when used to describe a nucleic acid molecule that hybridizes to DNA containing a polymorphism, refers to a nucleic acid that hybridizes to a DNA sequence that directly abuts the polymorphic nucleotide base position. For example, a nucleic acid molecule that can be used in a single base extension assay is "immediately adjacent" to the polymorphism.

As used herein, the phrase "interrogation position" refers to a physical position on a solid support that can be queried to obtain genotyping data for one or more predetermined genomic polymorphisms.

As used herein, the terms "introgression", "introgressed", and "introgressing" refer to both a natural and artificial process whereby genomic regions of one species, variety, or cultivar are moved into the genome of another species, variety, or cultivar by crossing those species. Exemplary methods for introgressing a trait of interest include, but are not limited to breeding an individual that has the trait of interest to an individual that does not, and backcrossing an individual that has the trait of interest to a recurrent parent.

As used herein, the term "linkage" refers to a phenomenon wherein alleles on the same chromosome tend to be transmitted together more often than expected by chance if their transmission were independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

As such, "linkage" typically implies physical proximity on a chromosome. Thus, two loci are linked if they are within in some embodiments 20 centiMorgans (cM), in some embodiments 15 cM, in some embodiments 12 cM, in some embodiments 10 cM, in some embodiments 9 cM, in some embodiments 8 cM, in some embodiments 7 cM, in some embodiments 6 cM, in some embodiments 5 cM, in some embodiments 4 cM, in some embodiments 3 cM, in some embodiments 2 cM, and in some embodiments 1 cM of each other. Similarly, a Marker Trait Locus (MTL) of the presently disclosed subject matter is linked to a marker if it is in some embodiments within 20, 15, 12, 10, 9, 8, 7, 6, 5, 4, 3, 2, or 1 cM of the marker.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous with the physical entity of a chromosome, although one of ordinary skill in the art will understand that a linkage group can also be defined as corresponding to a region of (i.e., less than the entirety) of a given chromosome.

As used herein, the phrase "linkage disequilibrium" is defined as change from the expected relative frequency of gamete types in a population of many individuals in a single generation such that two or more loci act as genetically linked loci. If the frequency in a population of allele S is x, s is x', B is y, and b is y', then the expected frequency of genotype SB is xy, that of Sb is xy', that of sB is x'y, and that of sb is x'y', and any deviation from these frequencies is an example of disequilibrium.

As used herein, the term "locus" refers to an established position on a chromosome of a species, and which may encompass a single nucleotide, several nucleotides, or more in a genomic region.

As used herein, the term "maize" refers to a plant, or a part thereof, of the species *Zea mays*, also referred to herein as *Zea mays* L.

As used herein, the phrase "maize-specific DNA sequence" refers to a polynucleotide sequence having a nucleotide sequence identity of in some embodiments more than 50%, in some embodiments more than 55%, in some embodiments more than 60%, in some embodiments more than 65%, in some embodiments more than 70%, in some embodiments more than 75%, in some embodiments more than 80%, in some embodiments more than 85%, in some embodiments more than 90%, in some embodiments more than 92%, in some embodiments more than 95%, in some embodiments more than 96%, in some embodiments more than 97%, in some embodiments more than 98%, and in some embodiments more than 99% with a sequence of the genome of the species *Zea mays* that shows the greatest similarity to it. In some embodiments and in the case of markers for any of MTL1-MTL18, MTPL1-10, MTSL1-6, and MTOL1-3 of the presently disclosed subject matter, a maize-specific DNA sequence comprises a part of a genomic DNA sequence of a *Zea mays* plant that flanks one of the MTL1-MTL18, MTPL1-10, MTSL1-6, and/or MTOL1-3 loci.

As used herein, the terms "marker" and "molecular marker" are used interchangeably to refer to an identifiable position on a chromosome the inheritance of which can be monitored and/or a reagent that is used in methods for visualizing differences in nucleic acid sequences present at such identifiable positions on chromosomes. Thus, in some embodiments a marker comprises a known or detectable nucleic acid sequence. Examples of markers include, but are not limited to genetic markers, protein composition, protein levels, oil composition, oil levels, carbohydrate composition, carbohydrate levels, fatty acid composition, fatty acid levels, amino acid composition, amino acid levels, biopolymers, starch composition, starch levels, fermentable starch, fermentation yield, fermentation efficiency (e.g., captured as digestibility at 24, 48, and/or 72 hours), energy yield, secondary compounds, metabolites, morphological characteristics, and agronomic characteristics. DNA-based markers include, but are not limited to restriction fragment length polymorphisms (RFLPs), random amplified polymorphic DNA (RAPD), amplified fragment length polymorphisms (AFLPs), single strand conformation polymorphism (SSCPs), single nucleotide polymorphisms (SNPs), insertion/deletion mutations (Indels), simple sequence repeats (SSRs), microsatellite repeats, sequence-characterized amplified regions (SCARs), cleaved amplified polymorphic sequence (CAPS) markers, and isozyme markers, microarray-based technologies, TAQMAN® markers, ILLUMINA® GOLDENGATE® Assay markers, nucleic acid sequences, or combinations of the markers described herein, which define a specific genetic and chromosomal location. The phrase a "molecular marker linked to an MTL" as defined herein can thus refer in some embodiments to SNPs, Indels, AFLP markers, or any other type of marker used in the field.

In some embodiments, a marker corresponds to an amplification product generated by amplifying a Zea mays nucleic acid with two oligonucleotide primers, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself and/or naturally occurring and/ or artificial alleleic differences) as an amplification product that is generated by amplifying Zea mays genomic DNA with a particular set of primers. In some embodiments, the amplifying is by PCR, and the primers are PCR primers that are designed to hybridize to opposite strands of the Zea mays genomic DNA in order to amplify a Zea mays genomic DNA sequence present between the sequences to which the PCR primers hybridize in the Zea mays genomic DNA. The amplified fragment that results from one or more rounds of amplification using such an arrangement of primers is a double stranded nucleic acid, one strand of which has a nucleotide sequence that comprises, in 5' to 3' order, the sequence of one of the primers, the sequence of the Zea mays genomic DNA located between the primers, and the reverse-complement of the second primer. Typically, the "forward" primer is assigned to be the primer that has the same sequence as a subsequence of the (arbitrarily assigned) "top" strand of a double-stranded nucleic acid to be amplified, such that the "top" strand of the amplified fragment includes a nucleotide sequence that is, in 5' to 3' direction, equal to the sequence of the forward primer—the sequence located between the forward and reverse primers of the top strand of the genomic fragment—the reverse-complement of the reverse primer. Accordingly, a marker that "corresponds to" an amplified fragment is a marker that has the same sequence of one of the strands of the amplified fragment.

As used herein, the phrase "marker assay" refers to a method for detecting a polymorphism at a particular locus using a particular method such as but not limited to measurement of at least one phenotype (such as seed color, oil content, or a visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, TAQMAN® Assays, ILLUMINA® GOLDENGATE® Assay analysis, nucleic acid sequencing technologies, or any other technique that can be employed to identify the nucleotide sequence of a nucleic acid.

As used herein, the terms "MTL1", "MTL2", "MTL3", "MTL4", "MTL5", "MTL6", "MTL7", "MTL8", "MTL9", "MTL10", "MTL11", "MTL12", "MTL13", "MTL14", "MTL15", "MTL16", "MTL17", "MTL4", and "MTL18" refer to genomic regions linked to ethanol production traits (alternatively referred to herein as "digestibility" traits), The terms "MTPL1", "MTPL2", "MTPL3", "MTPL4", "MTPL5", "MTPL6", "MTPL7", "MTPL8", "MTPL9", and MTPL10 refer to genomic regions linked to protein traits; "MTSL1", "MTSL2", "MTSL3", "MTSL4", "MTSL5", and "MTSL6" refer to genomic regions linked to starch traits; and "MTOL1", "MTOL2", and "MTOL3", refer to genomic regions linked oil traits as defined by markers present on Zea mays chromosomes and as described in more detail herein.

As used herein, the phrase "native trait" refers to any existing monogenic or oligogenic trait in a certain crop's germplasm. When identified through molecular marker(s), the information obtained can be used for the improvement of germplasm through marker assisted breeding of MTLs or genes.

As used herein, the phrases "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence identity. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST; Altschul et al., 1990; Altschul et al., 1997) and ClustalW programs, both available on the internet. Other suitable programs include, but are not limited to, GAP, BestFit, Plot Similarity, and FASTA, which are part of the Accelrys GCG Package available from Accelrys, Inc. of San Diego, Calif., United States of America. In some embodiments, a percentage of sequence identity refers to sequence identity over the full length of one of the sequences being compared. In some embodiments, a calculation to determine a percentage of sequence identity does not include in the calculation any nucleotide positions in which either of the compared nucleic acids includes an "n" (i.e., where any nucleotide could be present at that position).

As used herein, the phrases "progeny plant" refers to any plant resulting as progeny from a vegetative or sexual reproduction from one or more parent plants or descendants thereof. For instance, a progeny plant can be obtained by cloning or selfing of a parent plant or by crossing two parental plants and include selfings as well as the F1 or F2 or still further generations. An F1 is a first-generation progeny produced from parents at least one of which is used for the first time as donor of a trait, while progeny of second generation (F2) or subsequent generations (F3, F4, and the like) are specimens produced from selfings, intercrosses, backcrosses, or other crosses of F1s, F2s, and the like. An F1 can thus be (and in some embodiments is) a hybrid resulting from a cross between two true breeding parents (i.e., parents that are true-breeding are each homozygous for a trait of interest or an allele thereof), while an F2 can be (and in some embodiments is) a progeny resulting from self-pollination of the F1 hybrids.

As used herein, the term "phenotype" refers to the detectable characteristics of a cell or organism due to genetics. Non-limiting examples include protein content, starch content, oil content, and digestibility (i.e., ethanol production) phenotypes, all of which are exemplary yield phenotypes.

As used herein, the phrase "phenotypic marker" refers to a marker that can be used to discriminate between different phenotypes.

As used herein, the term "plant" refers to an entire plant, its organs (i.e., leaves, stems, roots, flowers etc.), seeds, plant cells, and progeny of the same. The term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "polymorphism" refers to the presence of one or more variations of a nucleic acid sequence at a locus in a population of one or more individuals. The sequence variation can be a base or bases that are different, inserted, or deleted. Polymorphisms can be, for example, single nucleotide polymorphisms (SNPs), simple sequence repeats (SSRs), and Indels, which are insertions and deletions. Additionally, the variation can be in a transcriptional profile or a methylation pattern. The polymorphic sites of a nucleic acid sequence can be determined by comparing the nucleic acid sequences at one or more loci in two or more germplasm entries.

As used herein, the term "population" refers to a genetically heterogeneous collection of plants sharing a common genetic derivation.

As used herein, the term "primer" refers to an oligonucleotide which is capable of annealing to a nucleic acid target allowing a DNA polymerase to attach, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, a plurality of primers are employed to amplify Zea mays nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the term "progeny" refers to any plant that results from a natural or assisted breeding of one or more plants. For example, progeny plants can be generated by crossing two plants (including, but not limited to crossing two unrelated plants, backcrossing a plant to a parental plant, intercrossing two plants, etc.), but can also be generated by selfing a plant, creating a double haploid, or other techniques that would be known to one of ordinary skill in the art.

As used herein, the phrase "quantitative trait locus" (QTL; quantitative trait loci—QTLs) refers to a genetic locus (or loci) that control to some degree a numerically representable trait that, in some embodiments, is continuously distributed. As such, the term MTL "marker trait loci" is used herein to refer to a chromosomal region containing alleles (e.g., in the form of genes or regulatory sequences) associated with the expression of a phenotypic trait. Thus, an MTL "associated with" a yield trait (e.g., a starch, protein, oil, and/or ethanol production trait) refers to one or more regions located on one or more chromosomes that includes at least one gene the expression of which influences a level of production and/or at least one regulatory region that controls the expression of one or more genes involved in one or more yield traits. The MTLs can be defined by indicating their genetic location in the genome of a given Zea mays plant using one or more molecular genomic markers. One or more markers, in turn, indicate a specific locus. Distances between loci are usually measured by the frequency of crossovers between loci on the same chromosome. The farther apart two loci are, the more likely that a crossover will occur between them. Conversely, if two loci are close together, a crossover is less likely to occur between them. Typically, one centiMorgan (cM) is equal to 1% recombination between loci. When a QTL can be indicated by multiple markers, the genetic distance between the end-point markers is indicative of the size of the QTL.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer to a meiotic crossover.

As used herein, the term "regenerate", and grammatical variants thereof, refers to the production of a plant from tissue culture.

As used herein, the phrases "selected allele", "desired allele", and "allele of interest" are used interchangeably to refer to a nucleic acid sequence that includes a polymorphic allele associated with a desired trait. It is noted that a "selected allele", "desired allele", and/or "allele of interest" can be associated with either an increase in a desired trait or a decrease in a desired trait, depending on the nature of the phenotype sought to be generated in an introgressed plant.

As used herein, the phrase "single nucleotide polymorphism", or "SNP", refers to a polymorphism that constitutes a single base pair difference between two nucleotide sequences. As used herein, the term "SNP" also refers to differences between two nucleotide sequences that result from simple alterations of one sequence in view of the other that occurs at a single site in the sequence. For example, the term "SNP" is intended to refer not just to sequences that differ in a single nucleotide as a result of a nucleic acid substitution in one versus the other, but is also intended to refer to sequences that differ in 1, 2, 3, or more nucleotides as a result of a deletion of 1, 2, 3, or more nucleotides at a single site in one of the sequences versus the other. It would be understood that in the case of two sequences that differ from each other only by virtue of a deletion of 1, 2, 3, or more nucleotides at a single site in one of the sequences versus the other, this same scenario can be considered an addition of 1, 2, 3, or more nucleotides at a single site in one of the sequences versus the other, depending on which of the two sequences is considered the reference sequence. Single site insertions and/or deletions are thus also considered to be encompassed by the term "SNP".

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Tijssen, 1993. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the phrase "TAQMAN® Assay" refers to real-time sequence detection using PCR based on the TAQMAN® Assay sold by Applied Biosystems, Inc. of Foster City, Calif., United States of America. For an identified marker a TAQMAN® Assay can be developed for the application in the breeding program.

As used herein, the term "tester" refers to a line used in a testcross with one or more other lines wherein the tester and the line(s(tested are genetically dissimilar. A tester can be an isogenic line to the crossed line.

As used herein, the term "trait" refers to a phenotype of interest, a gene that contributes to a phenotype of interest, as well as a nucleic acid sequence associated with a gene that contributes to a phenotype of interest. For example, a "yield trait" refers to a yield phenotype as well as a gene that contributes to a yield phenotype and a nucleic acid sequence (e.g., an SNP or other marker) that is associated with a yield phenotype.

As used herein, the term "transgene" refers to a nucleic acid molecule introduced into an organism or its ancestors by some form of artificial transfer technique. The artificial transfer technique thus creates a "transgenic organism" or a "transgenic cell". It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

As used herein, the term "yield" refers to any measure of a plant, its parts, or its structure that can be measured and/or quantitated in order to assess an extent of or a rate of plant growth and development. As such, a "yield trait" is any trait that can be shown to influence yield in a plant under any set of growth conditions. Exemplary yield traits include, but are not limited to protein content, starch content, oil content, and digestibility (ethanol production) at 24, 48, or 72 hours, as those traits are described herein.

For example, starch content can be measured in a plant, and as set forth herein, can correlate with increased yield in *Zea mays*. Therefore, "starch" is a "yield trait" as that term is employed herein. Similarly, a genetic locus that is associated with increased or decreased starch content in a *Zea mays* plant (or a part thereof) is referred to herein as "associated with starch" or a "starch-associated trait", but it is also a locus that is "associated with yield" and is a "yield-associated trait". The same variations with respect to protein content, oil content, and digestibility (ethanol production) at 24, 48, or 72 hours also apply to the general terms and phrases "yield", "associated with yield", and "yield-associated" as those terms and phrases are used herein.

II. Molecular Markers, MTLs, and Compositions for Assaying Nucleic Acid Sequences Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., STS, SSR/microsatellites, AFLP, and the like.). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson, 1993; Zietkiewicz et al., 1994. The recombination frequencies of molecular markers on different chromosomes are generally 50%. Between molecular markers located on the same chromosome, the recombination frequency generally depends on the distance between the markers. A low recombination frequency typically corresponds to a small genetic distance between markers on a chromosome. Comparing all recombination frequencies results in the most logical order of the molecular markers on the chromosomes. This most logical order can be depicted in a linkage map (Paterson, 1996). A group of adjacent or contiguous markers on the linkage map that is associated with increased yield can provide the position of an MTL associated with increased yield.

II.A. Ethanol Production (Digestibility) Marker Trait Loci

In some embodiments, the presently disclosed subject matter provides markers associated with improved ethanol production traits, also referred to herein as "digestibility" (DGST) traits at 24, 48, or 72 hours. As used herein, the phrase "digestibility at 24 hours" refers to dry grind ethanol percentage after 24 hours fermentation. Similarly, the phrases "digestibility at 48 hours" and "digestibility at 72 hours" refer to dry grind ethanol percentage after 48 and 72 hours fermentation, respectively (see Table 4 below).

As set forth in Tables 5 and 6, the inbred platform and the inbred panel included over 1700 different lines that were tested for digestibility at 24, 48, and 72 hours. Summarizing the data presented therein, the mean values for digestibility at 24, 48, and 72 hours were 5.02±0.92, 6.34±1.08, and 7.88±1.01, respectively. As such, the presence of an improved ethanol production trait in a *Zea mays* plant (or in a part, progeny, or tissue culture thereof) results in the *Zea mays* plant having a digestibility at 24 hours that is greater than 5.02, 6.34, and 7.88, respectively. In non-limiting, exemplary embodiments, an improved digestibility trait can result in a plant with digestibility that is in some embodiments greater than 5.5, 6.0, 6.5, 7.0, 7.5, or 8.0 at 24 hours; in some embodiments greater than 6.5, 7.0, 7.5, 8.0, 8.5, 9.0, 9.5, or 10.0 at 48 hours; and/or in some embodiments greater than 8.0, 8.5, 9.0, 9.5, 10.0, 10.5, 11.0, or 11.5 at 72 hours. Alternatively, if a reduced digestibility is desired at 24, 48, and/or 72 hours, the digestibility of an improved plant can be in some embodiments less than 5.0, 4.5, 4.0, 3.5, 3.0, 2.5, or 2.0 at 24 hours; in some embodiments less than 6.0, 5.5, 5.0, 4.5, 4.0, 3.5, 3.0, 2.5, 2.0, or 1.5 at 48 hours; and/or in some embodiments less than 7.5, 7.0, 6.5, 6.0, 5.5, 5.0, 4.5, 4.0, 3.5, 3.0, or 2.5 at 72 hours.

In some embodiments, the markers are associated with one or more alleles that confer an ethanol production-associated trait. In some embodiments, the one or more alleles are characterized by one or more Marker Trait Loci (MTL) selected from, but not limited to, MTL1-MTL18, which are located on seven (7) different chromosomes as follows:

(i) MTL1 is defined by a first assay primer and a second assay primer, wherein said assays primers amplify a subsequence of SEQ ID NO: 1 generated by amplifying a *Zea mays* nucleic acid with a first assay primer comprising a nucleotide sequence as set forth in SEQ ID NO: 2 and a second assay primer comprising a nucleotide sequence as set forth in SEQ ID NO: 3; and further wherein MTL1 identifies alleles of an ethanol production-associated trait by identification of a single nucleic polymorphism at nucleotide position 701 of SEQ ID NO: 1 (nucleotide position 30 of SEQ ID NO: 111) and comprises any part of a DNA sequence associated within 1, 2, 3, 4, 5, 6, 7, 8, 9, 10, 15, 20, of 25 cM of SEQ ID NO: 1 on *Zea mays* chromosome 5 that confers an improved ethanol production-associated trait;

(ii) MTL2 is defined by a first assay primer and a second assay primer, wherein said assays primers amplify a subsequence of SEQ ID NO: 4 generated by amplifying a *Zea mays* nucleic acid with a first assay primer comprising a nucleotide sequence as set forth in SEQ ID NO: 5 and a second assay primer comprising a nucleotide sequence as set forth in SEQ ID NO: 6; and further wherein MTL2 identifies alleles of an ethanol production-associated trait by identification of a single nucleic polymorphism at nucleotide position 498 of SEQ ID NO: 4 (nucleotide position 23 of SEQ ID NO: 112) and comprises any part of a DNA sequence associated within 1, 2, 3, 4, 5, 6, 7, 8, 9, 10, 15, 20, of 25 cM of SEQ ID NO: 1 on *Zea mays* chromosome 5 that confers an improved ethanol production-associated trait;

(iii) MTL3 is defined by a first assay primer and a second assay primer, wherein said assay primers amplify a subsequence of SEQ ID NO: 7 generated by amplifying a *Zea mays* nucleic acid with a first assay primer comprising a nucleotide sequence as set forth in SEQ ID NO: 8 and a second assay primer comprising a nucleotide sequence as set forth in SEQ ID NO: 9; and further wherein MTL3 identifies alleles of an ethanol production-associated trait by identification of a single nucleic polymorphism at nucleotide position 587 of SEQ ID NO: 7 (nucleotide position 33 of SEQ ID NO: 113) and comprises any part of a DNA sequence associated within 1, 2, 3, 4, 5, 6, 7, 8, 9, 10, 15, 20, of 25 cM of SEQ ID NO: 7 on *Zea mays* chromosome 5 that confers an improved ethanol production-associated trait;

(iv) MTL4 is defined by a first assay primer and a second assay primer, wherein said assay primers amplify a subsequence of SEQ ID NO: 10 generated by amplifying a *Zea mays* nucleic acid with a first assay primer comprising a nucleotide sequence as set forth in SEQ ID NO: 11 and a second assay primer comprising a nucleotide sequence as set forth in SEQ ID NO: 12; and further wherein MTL4 identifies alleles of an ethanol production-associated trait by identification of a single nucleic polymorphism at nucleotide position 708 of SEQ ID NO: 10 (nucleotide position 76 of SEQ ID NO: 114) and comprises any part of a DNA sequence associated within 1, 2, 3, 4, 5, 6, 7, 8, 9, 10, 15, 20, of 25 cM of SEQ ID NO: 10 on *Zea mays* chromosome 3 that confers an improved ethanol production-associated trait;

(v) MTL5 is defined by a first assay primer and a second assay primer, wherein said assay primers amplify a subsequence of SEQ ID NO: 13 generated by amplifying a *Zea mays* nucleic acid with a first assay primer comprising a nucleotide sequence as set forth in SEQ ID NO: 14 and a second assay primer comprising a nucleotide sequence as set forth in SEQ ID NO: 15; and further wherein MTL5 identifies alleles of an ethanol production-associated trait by identification of a single nucleic polymorphism at nucleotide position 140 of SEQ ID NO: 13 (nucleotide position 58 of SEQ ID NO: 115) and comprises any part of a DNA sequence associated within 1, 2, 3, 4, 5, 6, 7, 8, 9, 10, 15, 20, of 25 cM of SEQ ID NO: 13 on *Zea mays* chromosome 2 that confers an improved ethanol production-associated trait;

(vi) MTL6 is defined by a first assay primer and a second assay primer, wherein said assay primers amplify a subsequence of SEQ ID NO: 16 generated by amplifying a *Zea mays* nucleic acid with a first assay primer comprising a nucleotide sequence as set forth in SEQ ID NO: 17 and a second assay primer comprising a nucleotide sequence as set forth in SEQ ID NO: 18; and further wherein MTL16 identifies alleles of an ethanol production-associated trait by identification of a single nucleic polymorphism at nucleotide position 116 of SEQ ID NO: 16 (nucleotide position 33 of SEQ ID NO: 116) and comprises any part of a DNA sequence associated within 1, 2, 3, 4, 5, 6, 7, 8, 9, 10, 15, 20, of 25 cM of SEQ ID NO: 16 on *Zea mays* chromosome 5 that confers an improved ethanol production-associated trait;

(vii) MTL7 is defined by a first assay primer and a second assay primer, wherein said assay primers amplify a subsequence of SEQ ID NO: 19 generated by amplifying a *Zea mays* nucleic acid with a first assay primer comprising a nucleotide sequence as set forth in SEQ ID NO: 20 and a second assay primer comprising a nucleotide sequence as set forth in SEQ ID NO: 21; and further wherein MTL7 identifies alleles of an ethanol production-associated trait by identification of a single nucleic polymorphism at nucleotide position 269 of SEQ ID NO: 19 (nucleotide position 32 of SEQ ID NO: 117) and comprises any part of a DNA sequence associated within 1, 2, 3, 4, 5, 6, 7, 8, 9, 10, 15, 20, of 25 cM of SEQ ID NO: 19 on *Zea mays* chromosome 7 that confers an improved ethanol production-associated trait;

(viii) MTL8 is defined by a first assay primer and a second assay primer, wherein said assay primers amplify a subsequence of SEQ ID NO: 22 generated by amplifying a *Zea mays* nucleic acid with a first assay primer comprising a nucleotide sequence as set forth in SEQ ID NO: 23 and a second assay primer comprising a nucleotide sequence as set forth in SEQ ID NO: 24; and further wherein MTL8 identifies alleles of an ethanol production-associated trait by identification of a single nucleic polymorphism at nucleotide position 280 of SEQ ID NO: 22 (nucleotide position 23 of SEQ ID NO: 118) and comprises any part of a DNA sequence associated within 1, 2, 3, 4, 5, 6, 7, 8, 9, 10, 15, 20, of 25 cM of SEQ ID NO: 22 on *Zea mays* chromosome 5 that confers an improved ethanol production-associated trait;

(ix) MTL9 is defined by a first assay primer and a second assay primer, wherein said assay primers amplify a subsequence of SEQ ID NO: 25 generated by amplifying a *Zea mays* nucleic acid with a first assay primer comprising a nucleotide sequence as set forth in SEQ ID NO: 26 and a second assay primer comprising a nucleotide sequence as set forth in SEQ ID NO: 27; and further wherein MTL9 identifies alleles of an ethanol production-associated trait by identification of a single nucleic polymorphism at nucleotide position 374 of SEQ ID NO: 25 (nucleotide position 46 of SEQ ID NO: 119) and comprises any part of a DNA sequence associated within 1, 2, 3, 4, 5, 6, 7, 8, 9, 10, 15, 20, of 25 cM of SEQ ID NO: 25 on *Zea mays* chromosome 5 that confers an improved ethanol production-associated trait;

(x) MTL10 is defined by a first assay primer and a second assay primer, wherein said assay primers amplify a subsequence of SEQ ID NO: 28 generated by amplifying a *Zea mays* nucleic acid with a first assay primer comprising a nucleotide sequence as set forth in SEQ ID NO: 29 and a second assay primer comprising a nucleotide sequence as set forth in SEQ ID NO: 30; and further wherein MTL10 identifies alleles of an ethanol production-associated trait by identification of a single nucleic polymorphism at nucleotide position 236 of SEQ ID NO: 28 (nucleotide position 41 of SEQ ID NO: 120) and comprises any part of a DNA sequence associated within 1, 2, 3, 4, 5, 6, 7, 8, 9, 10, 15, 20, of 25 cM of SEQ ID NO: 28 on *Zea mays* chromosome 1 that confers an improved ethanol production-associated trait;

(xi) MTL11 is defined by a first assay primer and a second assay primer, wherein said assay primers amplify a subsequence of SEQ ID NO: 31 generated by amplifying a *Zea mays* nucleic acid with a first assay primer comprising a nucleotide sequence as set forth in SEQ ID NO: 32 and a second assay primer comprising a nucleotide sequence as set forth in SEQ ID NO: 33; and further wherein MTL11 identifies alleles of an ethanol production-associated trait by identification of a single nucleic polymorphism at nucleotide position 605 of SEQ ID NO: 31 (nucleotide position 32 of SEQ ID NO: 121) and comprises any part of a DNA sequence associated within 1, 2, 3, 4, 5, 6, 7, 8, 9, 10, 15, 20, of 25 cM of SEQ ID NO: 31 on *Zea mays* chromosome 2 that confers an improved ethanol production-associated trait;

(xii) MTL12 is defined by a first assay primer and a second assay primer, wherein said assay primers amplify a subsequence of SEQ ID NO: 34 generated by amplifying a *Zea mays* nucleic acid with a first assay primer comprising a nucleotide sequence as set forth in SEQ ID NO: 35 and a second assay primer comprising a nucleotide sequence as set forth in SEQ ID NO: 36; and further wherein MTL12 identifies alleles of an ethanol production-associated trait by identification of a single nucleotide polymorphism at nucleotide position 349 of SEQ ID NO: 34 (nucleotide position 48 of SEQ ID NO: 122) and comprises any part of a DNA sequence associated within 1, 2, 3, 4, 5, 6, 7, 8, 9, 10, 15, 20, of 25 cM of SEQ ID NO: 34 on *Zea mays* chromosome 10 that confers an improved ethanol production-associated trait;

(xiii) MTL13 is defined by a first assay primer and a second assay primer, wherein said assay primers amplify a subsequence of SEQ ID NO: 37 generated by amplifying a *Zea mays* nucleic acid with a first assay primer comprising a nucleotide sequence as set forth in SEQ ID NO: 38 and a second assay primer comprising a nucleotide sequence as set forth in SEQ ID NO: 39; and further wherein MTL13 identifies alleles of an ethanol production-associated trait by identification of a single nucleic polymorphism at nucleotide position 389 of SEQ ID NO: 37 (nucleotide position 45 of SEQ ID NO: 123) and comprises any part of a DNA sequence associated within 1, 2, 3, 4, 5, 6, 7, 8, 9, 10, 15, 20, of 25 cM of SEQ ID NO: 37 on *Zea mays* chromosome 8 that confers an improved ethanol production-associated trait;

(xiv) MTL14 is defined by a first assay primer and a second assay primer, wherein said assay primers amplify a subsequence of SEQ ID NO: 40 generated by amplifying a *Zea mays* nucleic acid with a first assay primer comprising a nucleotide sequence as set forth in SEQ ID NO: 41 and a second assay primer comprising a nucleotide sequence as set forth in SEQ ID NO: 42; and further wherein MTL14 identifies alleles of an ethanol production-associated trait by identification of a single nucleic polymorphism at nucleotide position 66 of SEQ ID NO: 40 (nucleotide position 44 of SEQ ID NO: 124) and comprises any part of a DNA sequence associated within 1, 2, 3, 4, 5, 6, 7, 8, 9, 10, 15, 20, of 25 cM of SEQ ID NO: 40 on *Zea mays* chromosome 1 that confers an improved ethanol production-associated trait;

(xv) MTL15 is defined by a first assay primer and a second assay primer, wherein said assay primers amplify a subsequence of SEQ ID NO: 43 generated by amplifying a *Zea mays* nucleic acid with a first assay primer comprising a nucleotide sequence as set forth in SEQ ID NO: 44 and a second assay primer comprising a nucleotide sequence as set forth in SEQ ID NO: 45; and further wherein MTL15 identifies alleles of an ethanol production-associated trait by identification of a single nucleic polymorphism at nucleotide position 278 of SEQ ID NO: 43 (nucleotide position 48 of SEQ ID NO: 125) and comprises any part of a DNA sequence associated within 1, 2, 3, 4, 5, 6, 7, 8, 9, 10, 15, 20, of 25 cM of SEQ ID NO: 43 on *Zea mays* chromosome 5 that confers an improved ethanol production-associated trait;

(xvi) MTL16 is defined by a first assay primer and a second assay primer, wherein said assay primers amplify a subsequence of SEQ ID NO: 46 generated by amplifying a *Zea mays* nucleic acid with a first assay primer comprising a nucleotide sequence as set forth in SEQ ID NO: 47 and a second assay primer comprising a nucleotide sequence as set forth in SEQ ID NO: 48; and further wherein MTL16 identifies alleles of an ethanol production-associated trait by identification of a single nucleic polymorphism at nucleotide position 463 of SEQ ID NO: 46 (nucleotide position 20 of SEQ ID NO: 126) and comprises any part of a DNA sequence associated within 1, 2, 3, 4, 5, 6, 7, 8, 9, 10, 15, 20, of 25 cM of SEQ ID NO: 46 on *Zea mays* chromosome 1 that confers an improved ethanol production-associated trait;

(xvii) MTL17 is defined by a first assay primer and a second assay primer, wherein said assay primers amplify a subsequence of SEQ ID NO: 49 generated by amplifying a *Zea mays* nucleic acid with a first assay primer comprising a nucleotide sequence as set forth in SEQ ID NO: 50 and a second assay primer comprising a nucleotide sequence as set forth in SEQ ID NO: 51; and further wherein MTL17 identifies alleles of an ethanol production-associated trait by identification of a single nucleic polymorphism at nucleotide position 510 of SEQ ID NO: 49 (nucleotide position 126 of SEQ ID NO: 127) and comprises any part of a DNA sequence associated within 1, 2, 3, 4, 5, 6, 7, 8, 9, 10, 15, 20, of 25 cM of SEQ ID NO: 49 on *Zea mays* chromosome 5 that confers an improved ethanol production-associated trait; and (xviii) MTL18 is defined by a first assay primer and a second assay primer, wherein said assay primers amplify a subsequence of SEQ ID NO: 52 generated by amplifying a *Zea mays* nucleic acid with a first assay primer comprising a nucleotide sequence as set forth in SEQ ID NO: 53 and a second assay primer comprising a nucleotide sequence as set forth in SEQ ID NO: 54; and further wherein MTL18 identifies alleles of an ethanol production-associated trait by identification of a single nucleic polymorphism at nucleotide position 134 of SEQ ID NO: 52 (nucleotide position 126 of SEQ ID NO: 128) and comprises any part of a DNA sequence associated within 1, 2, 3, 4, 5, 6, 7, 8, 9, 10, 15, 20, of 25 cM of SEQ ID NO: 52 on *Zea mays* chromosome 10 that confers an improved ethanol production-associated trait.

II.B. Protein Marker Trait Loci

In some embodiments, the presently disclosed subject matter provides markers associated with improved protein traits.

As used herein, the phrase "protein content" refers to kernel protein content measured in percentage. As set forth in Tables 5 and 6, the inbred platform and the inbred panel included over 1700 different lines that were tested for protein content. Summarizing the data presented therein, the mean value for protein content was 12.45±1.46. As such, the presence of an improved protein trait in a *Zea mays* plant (or in a part, progeny, or tissue culture thereof) can result in the *Zea mays* plant having a protein content that is greater than 12.45. In non-limiting, exemplary embodiments, the protein content of an improved *Zea mays* plant can be in some embodiments greater than 12.5, 13.0, 13.5, 14.0, 14.5, 15.0, 15.5, 16.0, 16.5, 17.0, or 17.5. Alternatively, if a reduced protein content is desired, the protein content of an improved *Zea mays* plant can be in some embodiments less than 12.0, 11.5, 11.0, 10.5, 10.0, 9.5, 9.0, or 8.5.

In some embodiments, the markers are associated with one or more alleles that confer a protein associated trait. In some embodiments, the one or more alleles are characterized by one or more Marker Trait (Protein) Loci (MTPL) selected from, but not limited to, MTPL1-MTPL10, which are located on seven (7) different chromosomes as follows:

(i) MTPL1 is defined by a first assay primer and a second assay primer, wherein said assay primers amplify a subsequence of SEQ ID NO: 1 generated by amplifying a *Zea mays* nucleic acid with a first assay primer comprising a nucleotide sequence as set forth in SEQ ID NO: 2 and a second assay primer comprising a nucleotide sequence as set forth in SEQ ID NO: 3; and further wherein MTPL1 identifies alleles of a protein associated trait by identification of a single nucleic polymorphism at nucleotide position 701 of SEQ ID NO: 1 (nucleotide position 30 of SEQ ID NO: 111) and comprises any part of a DNA sequence associated within 1, 2, 3, 4, 5, 6, 7, 8, 9, 10, 15, 20, of 25 cM of SEQ ID NO: 1 on *Zea mays* chromosome 5 that confers a protein associated trait;

(ii) MTPL2 is defined by a first assay primer and a second assay primer, wherein said assay primers amplify a subsequence of SEQ ID NO: 10 generated by amplifying a *Zea mays* nucleic acid with a first assay primer comprising a nucleotide sequence as set forth in SEQ ID NO: 11 and a second assay primer comprising a nucleotide sequence as set forth in SEQ ID NO: 12; and further wherein MTPL2 identifies alleles of a protein associated trait by identification of a single nucleic polymorphism at nucleotide position 708 of SEQ ID NO: 10 (nucleotide position 76 of SEQ ID NO: 114) and comprises any part of a DNA sequence associated within 1, 2, 3, 4, 5, 6, 7, 8, 9, 10, 15, 20, of 25 cM of SEQ ID NO: 10 on *Zea mays* chromosome 3 that confers a protein associated trait;

(iii) MTPL3 is defined by a first assay primer and a second assay primer, wherein said assay primers amplify a subsequence of SEQ ID NO: 19 generated by amplifying a *Zea mays* nucleic acid with a first assay primer comprising a nucleotide sequence as set forth in SEQ ID NO: 20 and a second assay primer comprising a nucleotide sequence as set forth in SEQ ID NO: 21; and further wherein MTPL3 identifies alleles of a protein associated trait by identification of a single nucleic polymorphism at nucleotide position 269 of SEQ ID NO: 19 (nucleotide position 32 of SEQ ID NO: 117) and comprises any part of a DNA sequence associated within 1, 2, 3, 4, 5, 6, 7, 8, 9, 10, 15, 20, of 25 cM of SEQ ID NO: 19 on *Zea mays* chromosome 7 that confers a protein associated trait;

(iv) MTPL4 is defined by a first assay primer and a second assay primer, wherein said assay primers amplify a subsequence of SEQ ID NO: 22 generated by amplifying a *Zea mays* nucleic acid with a first assay primer comprising a nucleotide sequence as set forth in SEQ ID NO: 23 and a second assay primer comprising a nucleotide sequence as set forth in SEQ ID NO: 24; and further wherein MTPL4 identifies alleles of a protein associated trait by identification of a single nucleic polymorphism at nucleotide position 280 of SEQ ID NO: 22 (nucleotide position 23 of SEQ ID NO: 118) and comprises any part of a DNA sequence associated within 1, 2, 3, 4, 5, 6, 7, 8, 9, 10, 15, 20, of 25 cM of SEQ ID NO: 22 on *Zea mays* chromosome 5 that confers a protein associated trait;

(v) MTPL5 is defined by a first assay primer and a second assay primer, wherein said assay primers amplify a subsequence of SEQ ID NO: 58 generated by amplifying a *Zea mays* nucleic acid with a first assay primer comprising a nucleotide sequence as set forth in SEQ ID NO: 59 and a second assay primer comprising a nucleotide sequence as set forth in SEQ ID NO: 60; and further wherein MTPL5 identifies alleles of a protein associated trait by identification of a single nucleic polymorphism at nucleotide position 119 of SEQ ID NO: 58 (nucleotide position 23 of SEQ ID NO: 130) and comprises any part of a DNA sequence associated within 1, 2, 3, 4, 5, 6, 7, 8, 9, 10, 15, 20, of 25 cM of SEQ ID NO: 58 on *Zea mays* chromosome 4 that confers a protein associated trait;

(vi) MTPL6 is defined by a first assay primer and a second assay primer, wherein said assay primers amplify a subsequence of SEQ ID NO: 64 generated by amplifying a *Zea mays* nucleic acid with a first assay primer comprising a nucleotide sequence as set forth in SEQ ID NO: 65 and a second assay primer comprising a nucleotide sequence as set forth in SEQ ID NO: 66; and further wherein MTPL6 identifies alleles of a protein associated trait by identification of a single nucleic polymorphism at nucleotide position 356 of SEQ ID NO: 64 (nucleotide position 43 of SEQ ID NO: 132) and comprises any part of a DNA sequence associated within 1, 2, 3, 4, 5, 6, 7, 8, 9, 10, 15, 20, of 25 cM of SEQ ID NO: 64 on *Zea mays* chromosome 7 that confers a protein associated trait;

(vii) MTPL7 is defined by a first assay primer and a second assay primer, wherein said assay primers amplify a subsequence of SEQ ID NO: 52 generated by amplifying a *Zea mays* nucleic acid with a first assay primer comprising a nucleotide sequence as set forth in SEQ ID NO: 53 and a second assay primer comprising a nucleotide sequence as set forth in SEQ ID NO: 54; and further wherein MTPL7 identifies alleles of a protein associated trait by identification of a single nucleic polymorphism at nucleotide position 134 of SEQ ID NO: 52 (nucleotide position 126 of SEQ ID NO: 128) and comprises any part of a DNA sequence associated within 1, 2, 3, 4, 5, 6, 7, 8, 9, 10, 15, 20, of 25 cM of SEQ ID NO: 52 on *Zea mays* chromosome 10 that confers a protein associated trait;

(viii) MTPL8 is defined by a first assay primer and a second assay primer, wherein said assay primers amplify a subsequence of SEQ ID NO: 49 generated by amplifying a *Zea mays* nucleic acid with a first assay primer comprising a nucleotide sequence as set forth in SEQ ID NO: 50 and a second assay primer comprising a nucleotide sequence as set forth in SEQ ID NO: 51; and further wherein MTPL8 identifies alleles of a protein associated trait by identification of a single nucleic polymorphism at nucleotide position 510 of SEQ ID NO: 49 (nucleotide position 126 of SEQ ID NO: 127) and comprises any part of a DNA sequence associated within 1, 2, 3, 4, 5, 6, 7, 8, 9, 10, 15, 20, of 25 cM of SEQ ID NO: 49 on *Zea mays* chromosome 5 that confers a protein associated trait;

(ix) MTPL9 is defined by a first assay primer and a second assay primer, wherein said assay primers amplify a subsequence of SEQ ID NO: 40 generated by amplifying a *Zea mays* nucleic acid with a first assay primer comprising a nucleotide sequence as set forth in SEQ ID NO: 41 and a second assay primer comprising a nucleotide sequence as set forth in SEQ ID NO: 42; and further wherein MTPL9 identifies alleles of a protein associated trait by identification of a single nucleic polymorphism at nucleotide position 66 of SEQ ID NO: 40 (nucleotide position 44 of SEQ ID NO: 123) and comprises any part of a DNA sequence associated within 1, 2, 3, 4, 5, 6, 7, 8, 9, 10, 15, 20, of 25 cM of SEQ ID NO: 40 on *Zea mays* chromosome 1 that confers a protein associated trait; and (x) MTPL10 is defined by a first assay primer and a second assay primer, wherein said assay primers amplify a subsequence of SEQ ID NO: 61 generated by amplifying a *Zea mays* nucleic acid with a first assay primer comprising a nucleotide sequence as set forth in SEQ ID NO: 62 and a second assay primer comprising a nucleotide sequence as set forth in SEQ ID NO: 63; and further wherein MTSPL10 identifies alleles of a protein associated trait by identification of a single nucleic polymorphism at nucleotide position 347 of SEQ ID NO: 61 (nucleotide position 53 of SEQ ID NO: 131) and comprises any part of a DNA sequence associated within 1, 2, 3, 4, 5, 6, 7, 8, 9, 10, 15, 20, of 25 cM of SEQ ID NO: 61 on *Zea mays* chromosome 6 that confers a protein associated trait.

II.C. Starch Marker Trait Loci

In some embodiments, the presently disclosed subject matter provides markers associated with improved starch traits.

As used herein, the phrase "starch content" refers to grain starch content measured in percentage. As set forth in Tables 5 and 6, the inbred platform and the inbred panel included over 1700 different lines that were tested for starch content. Summarizing the data presented therein, the mean value for starch content was 70.03±2.37. As such, the presence of an improved starch trait in a *Zea mays* plant (or in a part, progeny, or tissue culture thereof) can result in the *Zea mays* plant having a starch content that is greater than 70.03. In non-limiting, exemplary embodiments, the starch content of an improved *Zea mays* plant can be in some embodiments greater than 71, 72, 73, 74, 75, 76, 77, or 78. Alternatively, if a reduced starch content is desired, the starch content of an improved *Zea mays* plant can be in some embodiments less than 70, 69, 68, 67, 66, 65, 64, 63, 62, 61, or 60.

In some embodiments, the markers are associated with one or more alleles that confer a starch associated trait. In some embodiments, the one or more alleles are characterized by one or more Marker Trait (Starch) Loci (MTSL) selected from, but not limited to, MTSL1-MTSL6, which are located on five (5) different chromosomes as follows:

(i) MTSL1 is defined by a first assay primer and a second assay primer, wherein said assay primers amplify a subsequence of SEQ ID NO: 1 generated by amplifying a *Zea mays* nucleic acid with a first assay primer comprising a nucleotide sequence as set forth in SEQ ID NO: 2 and a second assay primer comprising a nucleotide sequence as set forth in SEQ ID NO: 3; and further wherein MTSL1 identifies alleles of a starch associated trait by identification of a single nucleic polymorphism at nucleotide position 701 of SEQ ID NO: 1 (nucleotide position 30 of SEQ ID NO: 111) and comprises any part of a DNA sequence associated within 1, 2, 3, 4, 5, 6, 7, 8, 9, 10, 15, 20, of 25 cM of SEQ ID NO: 1 on *Zea mays* chromosome 5 that confers a starch associated trait;

(ii) MTSL2 is defined by a first assay primer and a second assay primer, wherein said assay primers amplify a subsequence of SEQ ID NO: 4 generated by amplifying a *Zea mays* nucleic acid with a first assay primer comprising a nucleotide sequence as set forth in SEQ ID NO: 5 and a second assay primer comprising a nucleotide sequence as set forth in SEQ ID NO: 6; and further wherein MTSL2 identifies alleles of a starch associated trait by identification of a single nucleic polymorphism at nucleotide position 498 of SEQ ID NO: 4 (nucleotide position 23 of SEQ ID NO: 112) and comprises any part of a DNA sequence associated within 1, 2, 3, 4, 5, 6, 7, 8, 9, 10, 15, 20, of 25 cM of SEQ ID NO: 4 on *Zea mays* chromosome 5 that confers a starch associated trait;

(iii) MTSL3 is defined by a first assay primer and a second assay primer, wherein said assay primers amplify a subsequence of SEQ ID NO: 7 generated by amplifying a *Zea mays* nucleic acid with a first assay primer comprising a nucleotide sequence as set forth in SEQ ID NO: 8 and a second assay primer comprising a nucleotide sequence as set forth in SEQ ID NO: 9; and further wherein MTSL3 identifies alleles of a starch associated trait by identification of a single nucleic polymorphism at nucleotide position 587 of SEQ ID NO: 7 (nucleotide position 33 of SEQ ID NO: 113) and comprises any part of a DNA sequence associated within 1, 2, 3, 4, 5, 6, 7, 8, 9, 10, 15, 20, of 25 cM of SEQ ID NO: 7 on *Zea mays* chromosome 5 that confers a starch associated trait;

(iv) MTSL4 is defined by a first assay primer and a second assay primer, wherein said assay primers amplify a subsequence of SEQ ID NO: 10 generated by amplifying a *Zea mays* nucleic acid with a first assay primer comprising a nucleotide sequence as set forth in SEQ ID NO: 11 and a second assay primer comprising a nucleotide sequence as set forth in SEQ ID NO: 12; and further wherein MTSL4 identifies alleles of a starch associated trait by identification of a single nucleic polymorphism at nucleotide position 708 of SEQ ID NO: 10 (nucleotide position 76 of SEQ ID NO: 114) and comprises any part of a DNA sequence associated within 1, 2, 3, 4, 5, 6, 7, 8, 9, 10, 15, 20, of 25 cM of SEQ ID NO: 10 on *Zea mays* chromosome 3 that confers a starch associated trait;

(v) MTSL5 is defined by a first assay primer and a second assay primer, wherein said assay primers amplify a subsequence of SEQ ID NO: 37 generated by amplifying a *Zea mays* nucleic acid with a first assay primer comprising a nucleotide sequence as set forth in SEQ ID NO: 38 and a second assay primer comprising a nucleotide sequence as set forth in SEQ ID NO: 39; and further wherein MTSL5 identifies alleles of a starch associated trait by identification of a single nucleic polymorphism at nucleotide position 389 of SEQ ID NO: 37 (nucleotide position 45 of SEQ ID NO: 123) and comprises any part of a DNA sequence associated within 1, 2, 3, 4, 5, 6, 7, 8, 9, 10, 15, 20, of 25 cM of SEQ ID NO: 37 on Zea mays chromosome 8 that confers a starch associated trait; and (vi) MTSL6 is defined by a first assay primer and a second assay primer, wherein said assay primers amplify a subsequence of SEQ ID NO: 61 generated by amplifying a Zea mays nucleic acid with a first assay primer comprising a nucleotide sequence as set forth in SEQ ID NO: 62 and a second assay primer comprising a nucleotide sequence as set forth in SEQ ID NO: 63; and further wherein MTSL6 identifies alleles of a starch associated trait by identification of a single nucleic polymorphism at nucleotide position 347 of SEQ ID NO: 61 (nucleotide position 53 of SEQ ID NO: 131) and comprises any part of a DNA sequence associated within 1, 2, 3, 4, 5, 6, 7, 8, 9, 10, 15, 20, of 25 cM of SEQ ID NO: 61 on Zea mays chromosome 6 that confers a starch associated trait.

II.D. Oil Marker Trait Loci

In some embodiments, the presently disclosed subject matter provides markers associated with improved oil traits. In some embodiments, the markers are associated with one or more alleles that confer an oil associated trait.

As used herein, the phrase "oil content" refers to grain oil content measured in percentage. As set forth in Tables 5 and 6, the inbred platform and the inbred panel included over 1700 different lines that were tested for oil content. Summarizing the data presented therein, the mean value for oil content was 3.93±0.62. As such, the presence of an improved oil trait in a Zea mays plant (or in a part, progeny, or tissue culture thereof) can result in the Zea mays plant having an oil content that is greater than 3.93. In non-limiting, exemplary embodiments, the oil content of an improved Zea mays plant can be in some embodiments greater than 4.0, 4.5, 5.0, 5.5, 6.0, or 6.5. Alternatively, if a reduced oil content is desired, the oil content of an improved Zea mays plant can be in some embodiments less than 3.5, 3.0, or 2.5.

In some embodiments, the one or more alleles are characterized by one or more Marker Trait (Oil) Loci (MTOL) selected from, but not limited to, MTOL1-MTOL3, which are located on two (2) different chromosomes as follows:

(i) MTOL1 is defined by a first assay primer and a second assay primer, wherein said assay primers amplify a subsequence of SEQ ID NO: 55 generated by amplifying a Zea mays nucleic acid with a first assay primer comprising a nucleotide sequence as set forth in SEQ ID NO: 56 and a second assay primer comprising a nucleotide sequence as set forth in SEQ ID NO: 57; and further wherein MTOL1 identifies alleles of an oil associated trait by identification of a single nucleic polymorphism at nucleotide position 367 of SEQ ID NO: 55 (nucleotide position 32 of SEQ ID NO: 129) and comprises any part of a DNA sequence associated within 1, 2, 3, 4, 5, 6, 7, 8, 9, 10, 15, 20, of 25 cM of SEQ ID NO: 55 on Zea mays chromosome 1 that confers an oil associated trait;

(ii) MTOL2 is defined by a first assay primer and a second assay primer, wherein said assay primers amplify a subsequence of SEQ ID NO: 64 generated by amplifying a Zea mays nucleic acid with a first assay primer comprising a nucleotide sequence as set forth in SEQ ID NO: 65 and a second assay primer comprising a nucleotide sequence as set forth in SEQ ID NO: 66; and further wherein MTOL2 identifies alleles of an oil associated trait by identification of a single nucleic polymorphism at nucleotide position 356 of SEQ ID NO: 64 (nucleotide position 43 of SEQ ID NO: 132) and comprises any part of a DNA sequence associated within 1, 2, 3, 4, 5, 6, 7, 8, 9, 10, 15, 20, of 25 cM of SEQ ID NO: 64 on Zea mays chromosome 7 that confers an oil associated trait; and (iii) MTOL3 is defined by a first assay primer and a second assay primer, wherein said assay primers amplify a subsequence of SEQ ID NO: 28 generated by amplifying a Zea mays nucleic acid with a first assay primer comprising a nucleotide sequence as set forth in SEQ ID NO: 29 and a second assay primer comprising a nucleotide sequence as set forth in SEQ ID NO: 30; and further wherein MTOL3 identifies alleles of an oil associated trait by identification of a single nucleic polymorphism at nucleotide position 236 of SEQ ID NO: 28 (nucleotide position 41 of SEQ ID NO: 120) and comprises any part of a DNA sequence associated within 1, 2, 3, 4, 5, 6, 7, 8, 9, 10, 15, 20, or 25 cM of SEQ ID NO: 28 on Zea mays chromosome 1 that confers an oil associated trait.

In some embodiments, a DNA sequence associated within 1, 2, 3, 4, 5, 6, 7, 8, 9, 10, 15, 20, or 25 cM of a marker of the presently disclosed subject matter displays a genetic recombination frequency of less than about 25%, 20%, 15%, 10%, 9%, 8%, 7%, 6%, 5%, 4%, 3%, 2%, or 1% with the marker of the presently disclosed subject matter. In some embodiments, the one or more marker loci associated with improved yield (e.g., starch, protein, oil, and/or ethanol production) traits are selected from the marker loci of increased starch and lower levels of protein. In some embodiments, the one or more marker loci associated with improved yield traits are a plurality of loci selected from the marker loci of starch and ethanol production traits, protein and ethanol production traits, or any other combination of two or more of the yield traits disclosed herein. In some embodiments, the one or more marker loci associated with improved yield traits are selected from marker loci localizing within the chromosome intervals of 25 cM or less. In some embodiments, the germplasm is a Zea mays line or variety.

The presently disclosed subject matter thus provides in some embodiments isolated and purified genetic markers associated with improved yield (e.g., starch, protein, oil, and/or ethanol production) traits in Zea mays. In some embodiments, the markers (a) are associated with starch, protein, oil, and/or digestibility (ethanol production) traits; or (b) comprise a nucleotide sequence that comprises the full length sequence of any of SEQ ID NOs: 1-173, the complement of any of SEQ ID NOs: 1-173, or informative fragments thereof; or (c) comprise a nucleotide sequence of at least 10, 15, 20, 25, or more contiguous nucleotides up to the full length of an amplification product from a DNA sample isolated from a maize, wherein the amplification product is produced by an amplification reaction using pairs of oligonucleotide primers comprising the following nucleotide sequences: SEQ ID NOs: 2 and 3; SEQ ID NOs: 5 and 6; SEQ ID SEQ ID NOs: 8 and 9; SEQ ID NOs: 11 and 12; SEQ ID NOs: 14 and 15; SEQ ID NOs: 17 and 18; SEQ ID NOs: 20 and 21; SEQ ID NOs: 23 and 24; SEQ ID NOs: 26 and 27; or SEQ ID NOs: 29 and 30; SEQ ID NOs: 32 and 33; SEQ ID NOs: 35 and 36; SEQ ID NOs: 38 and 39; SEQ ID NOs: 41 and 42; SEQ ID NOs: 44 and 45; SEQ ID NOs: 47 and 48; SEQ ID NOs: 50 and 51; SEQ ID NOs: 53 and 54; SEQ ID NOs: 56 and 57; SEQ ID NOs: 59 and 60; SEQ ID NOs: 62 and 63; or SEQ ID NOs: 65 and 66. In some embodiments, the probe comprises an isolated and purified genetic marker as disclosed herein and a detectable moiety.

The markers identified herein can be used is various aspects of the presently disclosed subject matter as set forth herein. Aspects of the presently disclosed subject matter are not to be limited to the use of the markers identified herein, however. It is stressed that the aspects can also make use of markers not explicitly disclosed herein or even yet to be identified. Other than the genetic unit "gene", on which the phenotypic expression depends on a large number of factors that cannot be predicted, the genetic unit "MTL" denotes a region on the genome that is directly related to a phenotypic quantifiable trait.

DNA fragments associated with the presence of an MTL including, but not limited to MTL1-18, MTPL1-10, MTSL1-6, and MTOL1-3, are also provided. In some embodiments, the DNA fragments associated with the presence of an MTL have a predicted length and/or nucleic acid sequence, and detecting a DNA fragment having the predicted length and/or the predicted nucleic acid sequence is performed such that the amplified DNA fragment has a length that corresponds (plus or minus a few bases; e.g., a length of one, two or three bases more or less) to the predicted length. In some embodiments, a DNA fragment is an amplified fragment and the amplified fragment has a predicted length and/or nucleic acid sequence as does an amplified fragment produced by a similar reaction with the same primers with the DNA from the plant in which the marker was first detected or the nucleic acid sequence that corresponds (i.e., as a nucleotide sequence identity of more than 80%, 90%, 95%, 97%, or 99%) to the expected sequence as based on the sequence of the marker associated with that MTL in the plant in which the marker was first detected. Upon a review of the instant disclosure, one of ordinary skill in the art would appreciate that markers that are absent in plants while they were present in at least one parent plant (so-called trans-markers), can also be useful in assays for detecting a desired trait in an progeny plant, although testing for the absence of a marker to detect the presence of a specific trait is not optimal. The detecting of an amplified DNA fragment having the predicted length or the predicted nucleic acid sequence can be performed by any of a number of techniques, including but not limited to standard gel electrophoresis techniques and/or by using automated DNA sequencers. The methods are not described here in detail as they are well known to the skilled person.

The primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including but not limited to temperature and composition (A/T vs. G/C content) of the primer.

In the context of an amplification primer, these are typically provided as one or more sets of bidirectional primers that include one or more forward and one or more reverse primers as commonly used in the art of DNA amplification such as in PCR amplification, As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing. Primers can be prepared by any suitable method. Methods for preparing oligonucleotides of specific sequence are known in the art, and include, for example, cloning, and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,068.

Primers can be labeled, if desired, by incorporating detectable moieties by for instance spectroscopic, fluorescence, photochemical, biochemical, immunochemical, or chemical moieties.

Template-dependent extension of an oligonucleotide primer is catalyzed by a polymerizing agent in the presence of adequate amounts of the four deoxyribonucleotides triphosphates (dATP, dGTP, dCTP and dTTP; i.e., dNTPs) or analogues, in a reaction medium that comprises appropriate salts, metal cations, and a pH buffering system. Suitable polymerizing agents are enzymes known to catalyze primer- and template-dependent DNA synthesis. Known DNA polymerases include, for example, *E. coli* DNA polymerase or its Klenow fragment, T4 DNA polymerase, and Taq DNA polymerase, as well as various modified versions thereof. The reaction conditions for catalyzing DNA synthesis with these DNA polymerases are known in the art. The products of the synthesis are duplex molecules consisting of the template strands and the primer extension strands, which include the target sequence. These products, in turn, can serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension can result in the exponential accumulation of the target region defined by the primers. Sufficient cycles are run to achieve the desired amount of polynucleotide containing the target region of nucleic acid. The desired amount can vary, and is determined by the function which the product polynucleotide is to serve.

The PCR method is well described in handbooks and known to the skilled person. After amplification by PCR, the target polynucleotides can be detected by hybridization with a probe polynucleotide which forms a stable hybrid with that of the target sequence under stringent to moderately stringent hybridization and wash conditions. If it is expected that the probes will be essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell, 2001. Generally, lower salt concentration and higher temperature increase the stringency of hybridization conditions.

In order to detect in a plant the presence of two MTLs on a single chromosome, chromosome painting methods can also be used. In such methods at least a first MTL and at least a second MTL can be detected in the same chromosome by in situ hybridization or in situ PCR techniques. More conveniently, the fact that two MTLs are present on a single chromosome can be confirmed by determining that they are in coupling phase: i.e., that the traits show reduced segregation when compared to genes residing on separate chromosomes.

The groups (e.g., starch, protein, oil, and ethanol production) of MTLs identified herein are located on a number of different chromosomes or linkage groups and their locations can be characterized by a number of otherwise arbitrary markers. In the present investigations, single nucleotide polymorphisms (SNPs), were used, although restriction fragment length polymorphism (RFLP) markers, amplified fragment length polymorphism (AFLP) markers, microsatellite markers (e.g., SSRs), insertion mutation markers, sequence-characterized amplified region (SCAR) markers, cleaved amplified polymorphic sequence (CAPS) markers, isozyme markers, microarray-based technologies, TAQMAN® Assays, ILLUMINA® GOLDENGATE® Assay analysis, nucleic acid sequencing technologies, or combinations of these markers might also have been used, and indeed can be used.

In general, providing complete sequence information for an MTL is unnecessary, as the way in which the MTL is first detected—through an observed correlation between the presence of a single nucleotide polymorphism and the presence of a particular phenotypic trait—allows one to trace among a population of progeny plants those plants that have the genetic potential for exhibiting a particular phenotypic trait. By providing a non-limiting list of markers, the presently disclosed subject matter thus provides for the effective use of the presently disclosed MTLs in a breeding program. In some embodiments, a marker is specific for a particular line of descent. Thus, a specific trait can be associated with a particular marker.

The markers as disclosed herein not only indicate the location of the MTL, they also correlate with the presence of the specific phenotypic trait in a plant. It is noted that a single nucleotide polymorphism that indicates where an MTL is present in the genome is non-limiting. In general, the location of an MTL is indicated by a single nucleotide polymorphism that exhibit statistical correlation to the phenotypic trait. Once a marker is found outside a single nucleotide polymorphism (i.e., one that has a LOD-score below a certain threshold, indicating that the marker is so remote that recombination in the region between that marker and the MTL occurs so frequently that the presence of the marker does not correlate in a statistically significant manner to the presence of the phenotype), the boundaries of the MTL can be considered set. Thus, it is also possible to indicate the location of the MTL by other markers located within that specified region. It is further noted that a single nucleotide polymorphism can also be used to indicate the presence of the MTL (and thus of the phenotype) in an individual plant, which in some embodiments means that it can be used in marker-assisted selection (MAS) procedures.

In principle, the number of potentially useful markers can be very large. Any marker that is linked to an MTL (e.g., falling within the physically boundaries of the genomic region spanned by the markers having established LOD scores above a certain threshold thereby indicating that no or very little recombination between the marker and the MTL occurs in crosses, as well as any marker in linkage disequilibrium to the MTL, as well as markers that represent the actual causal mutations within the MTL) can be used in the presently disclosed methods and compositions, and are within the scope of the presently disclosed subject matter. This means that the markers identified in the application as associated with the MTLs (e.g., MTL1-MTL18, MTPL1-10, MTSL1-6, and MTOL1-3) are non-limiting examples of markers suitable for use in the presently disclosed methods and compositions.

Moreover, when an MTL, or the specific trait-conferring part thereof, is introgressed into another genetic background (i.e., into the genome of another maize or another plant species), then some markers might no longer be found in the progeny although the trait is present therein, indicating that such markers are outside the genomic region that represents the specific trait-conferring part of the MTL in the original parent line only and that the new genetic background has a different genomic organization. Such markers of which the absence indicates the successful introduction of the genetic element in the progeny are called "trans markers" and can be equally suitable with respect to the presently disclosed subject matter.

Upon the identification of an MTL, the MTL effect (e.g., the trait) can for instance be confirmed by assessing trait in progeny segregating for the MTLs under investigation. The assessment of the trait can suitably be performed by using phenotypic assessment as known in the art for yield traits. For example, NIR can be employed to detect oil, ethanol, starch, and protein. Additionally, (field) trials under natural and/or irrigated conditions can be conducted to assess the traits of hybrid and/or inbred maize.

The markers provided by the presently disclosed subject matter can be used for detecting the presence of one or more yield trait alleles at MTLs of the presently disclosed subject matter in a suspected yield trait introgressed maize plant, and can therefore be used in methods involving marker-assisted breeding and selection of such yield trait bearing maize plants. In some embodiments, detecting the presence of an MTL of the presently disclosed subject matter is performed with at least one of the markers for an MTL as defined herein. The presently disclosed subject matter therefore relates in another aspect to a method for detecting the presence of an MTL for at least one of the presently disclosed yield traits, comprising detecting the presence of a nucleic acid sequence of the MTL in a trait bearing maize plant, which presence can be detected by the use of the disclosed markers.

In some embodiments, the detecting comprises determining the nucleotide sequence of a *Zea mays* nucleic acid associated with an MTL. The nucleotide sequence of an MTL of the presently disclosed subject matter can for instance be resolved by determining the nucleotide sequence of one or more markers associated with the MTL and designing internal primers for the marker sequences that can then be used to further determine the sequence of the MTL outside of the marker sequences. For instance, the nucleotide sequence of the SNP markers disclosed herein can be obtained by isolating the markers from the electrophoresis gel used in the determination of the presence of the markers in the genome of a subject plant, and determining the nucleotide sequence of the markers by, for example, dideoxy chain termination sequencing methods, which are well known in the art. In some embodiments of such methods for detecting the presence of an MTL in a trait bearing maize plant, the method can also comprise providing a oligonucleotide or polynucleotide capable of hybridizing under stringent hybridization conditions to a nucleic acid sequence of a marker linked to the MTL, in some embodiments selected from the markers disclosed herein, contacting the oligonucleotide or polynucleotide with digested genomic nucleic acid of a trait bearing maize plant, and determining the presence of specific hybridization of the oligonucleotide or polynucleotide to the digested genomic nucleic acid. In some embodiments, the method is performed on a nucleic acid sample obtained from the trait-bearing maize plant, although in situ hybridization methods can also be employed. Alternatively, one of ordinary skill in the art can, once the nucleotide sequence of the MTL has been determined, design specific hybridization probes or oligonucleotides capable of hybridizing under stringent hybridization conditions to the nucleic acid sequence of the MTL and can use such hybridization probes in methods for detecting the presence of an MTL disclosed herein in a trait bearing maize plant.

The presently disclosed subject matter also provides compositions comprising amplification primer pairs capable of initiating polymerization by a nucleic acid polymerase on *Zea mays* nucleic acid templates to generate *Zea mays* marker amplicons. In some embodiments, the *Zea mays* marker amplicons correspond to SEQ ID NOs: 1, 4, 7, 10, 13, 16, 19, 22, 25, 28, 31, 34, 37, 40, 43, 46, 49, 52, 55, 58, 61, and 64, and/or informative fragments thereof. As used herein, the phrase "informative fragment" refers to a nucleotide sequence of any length that is present within any of SEQ ID NOs: 1-173 (e.g., at least 10, 15, 20, 25, or more nucleotides up to and including the full length of any of SEQ ID NOs: 1-173) that is indicative of the presence or absence of a genetic marker associated with improved yield (e.g., starch, protein, oil, and/or ethanol production) traits in *Zea mays*. In some embodiments, an informative fragment comprises an SNP selected from among nucleotide position 701 of SEQ ID NO: 1; nucleotide position 498 of SEQ ID NO: 4; nucleotide position 587 of SEQ ID NO: 7; nucleotide position 708 of SEQ ID NO: 10; nucleotide position 140 of SEQ ID NO: 13; nucleotide position 116 of SEQ ID NO: 16; nucleotide position 269 of SEQ ID NO: 19; nucleotide position 280 of SEQ ID NO: 22; nucleotide position 374 of SEQ ID NO: 25; nucleotide position 236 of SEQ ID NO: 28; nucleotide position 605 of SEQ ID NO: 31; nucleotide position 349 of SEQ ID NO: 34; nucleotide position 389 of SEQ ID NO: 37; nucleotide position 66 of SEQ ID NO: 40; nucleotide position 278 of SEQ ID NO: 43; nucleotide position 463 of SEQ ID NO: 46; nucleotide position 510 of SEQ ID NO: 49; nucleotide position 134 of SEQ ID NO: 52; nucleotide position 367 of SEQ ID NO: 55; nucleotide position 119 of SEQ ID NO: 58; nucleotide position 347 of SEQ ID NO: 61; and nucleotide position 356 of SEQ ID NO: 64.

III. Methods for Employing Markers and MTLs to Produce Improved Maize Plants by Marker Assisted Selection and Marker Assisted Breeding The presently disclosed subject matter provides methods for conveying selected yield traits (e.g., selected starch, protein, oil, and/or ethanol production traits) into maize germplasm. In some embodiments, the methods comprise introgressing yield traits into maize using one or more nucleic acid markers for marker-assisted selection among maize lines to be used in a maize breeding program, wherein the markers are linked to yield traits. In some embodiments, the one or more nucleic acid markers are selected from the group including, but not limited to, markers for starch, protein, oil, and/or ethanol production traits. In some embodiments, the one or more nucleic acid markers are selected from the group of markers listed in SEQ ID NOs: 1-173. In some embodiments, the marker-assisted selection comprises the use of an analysis technique selected from the group including, but not limited to, single nucleotide polymorphism (SNP) analysis, random amplified polymorphic DNA (RAPD) analysis, restriction fragment-length polymorphism (RFLP) analysis, microsatellite analysis, amplified fragment length polymorphism (AFLP) analysis, TAQ-MAN® Assay analysis (Applied Biosystems, Inc., Foster City, Calif., United States of America), and ILLUMINA® GOLDENGATE® Genotyping Assay analysis (Illumina Inc., San Diego, Calif., United States of America). In some embodiments, the methods further comprise screening an introgressed maize plant for an introgressed phenotypic trait.

The presently disclosed subject matter also provides methods for reliably and predictably introgressing yield traits (e.g., starch, protein, oil, and/or ethanol production traits) into maize germplasm. In some embodiments, the methods comprise using one or more nucleic acid markers for marker-assisted selection among maize lines to be used in a maize breeding program, wherein the nucleic acid markers are selected from the group including, but not limited to, SEQ ID NOs: 1-173, and introgressing the desired trait into the non-trait carrying maize germplasm. In some embodiments, the one or more nucleic acid markers are selected from the group including, but not limited to, markers for positive or negative alleles of yield traits (e.g., starch, protein, oil, and/or ethanol production traits). In some embodiments, the marker-assisted selection comprises the use of an analysis technique selected from the group including, but not limited to, SNP analysis, RAPD analysis, RFLP analysis, microsatellite analysis, AFLP analysis, TAQ-MAN® Assay analysis, and ILLUMINA® GOLDEN-GATE® Genotyping Assay analysis.

The presently disclosed subject matter also provides methods for the production of an inbred maize plant adapted for conferring, in hybrid combination with a suitable second inbred, improved yield traits (e.g., starch, protein, oil, and/or ethanol production traits). In some embodiments, the methods comprise (a) selecting a first donor parental line possessing a desired inbred allele for a first yield trait comprising an ethanol production trait and also possessing an inbred allele for a second yield trait selected from, but not limited to, a starch trait, a protein trait, an oil trait, and/or a second ethanol production trait; (b) crossing the first donor parent line with a second parental line in hybrid combination to produce an F1 generation, and producing an F2 generation from the F1 generation, wherein the F2 generation comprises a segregating plant population; (c) screening one or more members of the segregating plant population for presence of desired chromosomal loci associated with the first yield trait and with the second yield trait; (d) identifying a plant in the F2 generation, or a selfed and/or double haploid progeny of a plant from the F2 generation, that is homozygous for at least the first yield trait at sufficient loci to produce improved ethanol production in hybrid combination; and (e) establishing from the homozygous plant identified in step (d) an inbred maize plant adapted for conferring, in hybrid combination with a suitable second inbred, a yield trait. In some embodiments, the methods further comprise screening the plants of the line that is homozygous for improved yield traits at sufficient loci to give improved yield in hybrid combination.

In some embodiments, the detecting of the desired trait comprises detecting at least one allelic form of a polymorphic simple sequence repeat (SSR) or a single nucleotide polymorphism (SNP). In some embodiments, the detecting comprises amplifying the marker locus or a portion of the marker locus and detecting the resulting amplified marker amplicon. In some embodiments, the amplifying comprises: (a) admixing an amplification primer or amplification primer pair with a nucleic acid isolated from the first *Zea mays* plant or germplasm, wherein the primer or primer pair is complementary or partially complementary to at least a portion of the marker locus, and is capable of initiating DNA polymerization by a DNA polymerase using the maize nucleic acid as a template; and (b) extending the primer or primer pair in a DNA polymerization reaction comprising a DNA polymerase and a template nucleic acid to generate at least one amplicon. In some embodiments, the nucleic acid is selected from DNA and RNA. In some embodiments, the at least one allele is an SNP allele and the method comprises detecting the SNP using allele specific hybridization (ASH) analysis. In some embodiments, the amplifying comprises employing a polymerase chain reaction (PCR) or ligase chain reaction (LCR) using a nucleic acid isolated from the first maize plant or germplasm as a template in the PCR or LCR.

As used herein, the term "favorable allele" refers to an allele the presence of which is desirable in a plant in order to achieve a desired goal. For example, a favorable allele can be an allele that is associated with higher or lower yield (e.g., starch, protein, oil, and/or ethanol production), depending on whether higher or lower levels of these traits is desired under specific circumstances. In some embodiments, a favorable allele is associated with increased ethanol production. In some embodiments, a favorable allele is associated with decreased protein production. In some embodiments, a favorable allele is associated with increased starch production.

Table 10 (below) discloses exemplary SNPs that are associated with increases and decreases of various yield traits. In some embodiments, the favorable allele comprises a nucleotide selected from, but not limited to, (a) an A at nucleotide position 701 of SEQ ID NO: 1; (b) a G at nucleotide position 498 of SEQ ID NO: 4; (c) a T at nucleotide position 587 of SEQ ID NO: 7; (d) a G at nucleotide position 708 of SEQ ID NO: 10; (e) a C at nucleotide position 140 of SEQ ID NO: 13; (f) an A at nucleotide position 116 of SEQ ID NO: 16; (g) an A at nucleotide position 269 of SEQ ID NO: 19; (h) an A at nucleotide position 280 of SEQ ID NO: 22; (i) a Tat nucleotide position 374 of SEQ ID NO: 25; (j) a G at nucleotide position 236 of SEQ ID NO: 28; (k) a G at nucleotide position 605 of SEQ ID NO: 31; (l) a CGA trinucleotide sequence at nucleotide positions 349-351 of SEQ ID NO: 34; (m) a C at nucleotide position 389 of SEQ ID NO: 37; (n) a G at nucleotide position 66 of SEQ ID NO: 40; (o) a T at nucleotide position 278 of SEQ ID NO: 43; (p) a G at nucleotide position 463 of SEQ ID NO: 46; (q) a G at nucleotide position 510 of SEQ ID NO: 49; (r) a G at nucleotide position 134 of SEQ ID NO: 52; (s) an A at nucleotide position 367 of SEQ ID NO: 55; (t) a G at nucleotide position 119 of SEQ ID NO: 58; (u) a G at nucleotide position 347 of SEQ ID NO: 61; and (v) an A at nucleotide position 356 of SEQ ID NO: 64. In some embodiments, the nucleotide present at the aforementioned positions of SEQ ID NOs: 1, 4, 7, 10, 13, 16, 19, 22, 25, 28, 31, 34, 37, 40, 43, 46, 49, 52, 55, 58, 61, and 64 is determined in a plant.

Knowledge of the nucleotides present at these positions allows one of skill to determine whether or not the plant carries an allele of interest. If so, the plant can be chosen for further breeding. Thus, one of ordinary skill in the art would understand that plants can be affirmatively chosen for further use based on identifying favorable alleles at specific genomic sites (e.g., those listed hereinabove). However, it is also noted that the absence of a favorable allele at a specific site can also be used to affirmatively reject a certain plant as a candidate for further breeding.

For example, MTL1 is associated with markers that comprise SEQ ID NO: 1 and informative fragments thereof. As set forth in Table 10 (below), an A nucleotide at position 701 of SEQ ID NO: 1 is associated with decreased protein, increased starch, and increased digestibility at 48 and 72 hours. Thus, identification of the nucleotide at position 701 of SEQ ID NO: 1 in a plant can be employed to determine whether or not the plant is likely to carry the decreased protein, increased starch, and increased digestibility at 48 and 72 hours alleles. If the plant has an A nucleotide at position 701 of SEQ ID NO: 1 in one or both of its chromosome 5s, it is a candidate for further breeding in those instances in which decreased protein, increased starch, and/or increased digestibility at 48 and 72 hours is desirable.

However, as set forth in Table 10, having a Gat nucleotide 701 of SEQ ID NO: 1 would have the opposite effect of having an A at this position. Thus, Table 10 also indicates that if increased protein, decreased starch, and/or decreased digestibility at 48 and 72 hours is desired, plants can be screened for what nucleotide is present at position 701 of SEQ ID NO: 1, and those that have a G at this position in one or both of its chromosome 5s can be chosen under these circumstances, and those that have an A at this position in one or both of its chromosome 5s can be rejected. Thus, with respect to the alleles disclosed in Table 10, allele 1 or allele 2 can be considered to have opposite effects, and either can be a favorable allele (affirmatively chosen) or an unfavorable allele (affirmatively rejected) depending on the trait that is of interest.

In some embodiments, the at least one allele is correlated with at least one improved yield trait, the method comprising introgressing the allele in the first Zea mays plant or germplasm into a second Zea mays plant or germplasm to produce an introgressed Zea mays plant or germplasm. In some embodiments, the second Zea mays plant or germplasm displays more improved yield traits as compared to the first Zea mays plant or germplasm, and wherein the introgressed Zea mays plant or germplasm displays an increased improved yield trait as compared to the second Zea mays plant or germplasm.

The presently disclosed subject matter also provides methods for producing maize plants which carry improved yield traits (e.g., improved starch, protein, oil, and/or ethanol production traits). In some embodiments, the methods comprise providing a Zea mays plant which contains one or more alleles that confer improved yield, the alleles being characterized by one or more sets of loci. These alleles can be employed individually or in combinations within a set of yield traits (e.g., any of starch, protein, oil, and ethanol production traits) or between different sets of yield traits (e.g., starch, protein, oil, and/or ethanol production traits). Alternatively, all sets of yield traits can be employed. Combinations of yield traits or sets of yield traits selected for increase or decrease of any of a number of the presently disclosed yield traits can be employed to alter yield, and combinations of these yield traits can be introgressed into a single plant (i.e., "stacked"), if desired.

In some embodiments, a marker locus associated with an improved yield trait (e.g., a starch, protein, oil, and/or ethanol production trait) displays a genetic recombination frequency of less than about 50%, 25%, 20%, 15%, 10%, 9%, 8%, 7%, 6%, 5%, 4%, 3%, 2%, or 1% with a genetic locus encoding a yield trait. In some embodiments, the marker locus associated with an improved yield trait is selected from marker loci associated with an increased starch trait and associated with a decreased protein trait. In some embodiments, the marker locus associated with improved yield comprises a plurality of loci selected from marker loci associated with starch traits and ethanol production traits. In some embodiments, the marker locus associated with improved yield is selected from, but not limited to, marker loci localizing within the chromosome intervals of 20 cM. In some embodiments, the germplasm is a *Zea mays* line or variety.

In some embodiments, the detecting of the desired trait comprises detecting at least one allelic form of a polymorphic simple sequence repeat (SSR) or a single nucleotide polymorphism (SNP). In some embodiments, the detecting comprises amplifying the marker locus or a portion of the marker locus and detecting the resulting amplified marker amplicon. In some embodiments, the amplifying comprises (a) admixing an amplification primer or amplification primer pair with a nucleic acid isolated from the first *Zea mays* plant or germplasm, wherein the primer or primer pair is complementary or partially complementary to at least a portion of the marker locus and is capable of initiating DNA polymerization by a DNA polymerase using the maize nucleic acid as a template; and (b) extending the primer or primer pair in a DNA polymerization reaction comprising a DNA polymerase and a template nucleic acid to generate at least one amplicon. In some embodiments, the nucleic acid is selected from DNA and RNA. In some embodiments, the at least one allele is an SNP allele and the methods comprise detecting the SNP using allele specific hybridization (ASH) analysis, TAQMAN® Assay Analysis (Applied Biosystems, Inc., Foster City, Calif., United States of America), and/or the ILLUMINA® GOLDENGATE® Genotyping Assay analysis (Illumina Inc., San Diego, Calif., United States of America). In some embodiments, the amplifying comprises employing a polymerase chain reaction (PCR) or ligase chain reaction (LCR) using a nucleic acid isolated from the first maize plant or germplasm as a template in the PCR or LCR.

In some embodiments, the at least one allele is a favorable allele that positively correlates with an improved yield trait (e.g., an improved starch, protein, oil, and/or ethanol production trait). In some embodiments, the at least one allele is a favorable allele that negatively correlates with an improved yield trait (e.g., a starch, protein, oil, and/or ethanol production trait). In some embodiments, the at least one allele comprises two or more alleles. In some embodiments, the at least one allele is correlated with an improved yield trait (e.g., an starch, protein, oil, and/or ethanol production trait) and the methods comprise introgressing the allele in the first *Zea mays* plant or germplasm into a second *Zea mays* plant or germplasm to produce an introgressed *Zea mays* plant or germplasm. In some embodiments, the second *Zea mays* plant or germplasm is characterized by more improved yield traits as compared to the first *Zea mays* plant or germplasm, and wherein the introgressed *Zea mays* plant or germplasm displays an increase in the number of improved yield traits as compared to the second *Zea mays* plant or germplasm.

A method for introgressing an allele associated with a pre-selected yield trait into *Zea mays* germplasm, the method comprising: (a) selecting from a population of *Zea mays* plants at least one *Zea mays* plant that comprises an allele of a yield locus associated with a pre-selected yield trait, wherein the yield locus is genetically linked to at least one marker locus that co-segregates with the yield associated trait, and further wherein the yield locus comprises a nucleotide sequence at least 85% identical to a *Zea mays* genomic sequence selected from the group including, but not limited to, nucleotides 49337-50164 of GENBANK® Accession No. AC209208.3; nucleotides 43103-43821 of GENBANK® Accession No. AC206616.3; nucleotides 50033-20828 of GENBANK® Accession No. AC204769.3; nucleotides 99595-100453 of GENBANK® Accession No. AC214243.4; nucleotides 56729-57382 of GENBANK® Accession No. AC185458.4; nucleotides 113858-114950 of GENBANK® Accession No. AC211735.3; nucleotides 121592-123221 of GENBANK® Accession No. AC212758.3; nucleotides 159378-160234 of GENBANK® Accession No. AC203779.6; nucleotides 4367-4883 of GENBANK® Accession No. AC196146.3; nucleotides 106354-107115 of GENBANK® Accession No. AC214129.2; nucleotides 2608-3395 of GENBANK® Accession No. AC183312.5; nucleotides 116067-116863 of GENBANK® Accession No. AC194834.3; nucleotides 66678-67232 of GENBANK® Accession No. AC197472.2; nucleotides 10855-10962 or nucleotides 103384-103629 of GENBANK® Accession No. AC204604.3; nucleotides 173922-174662 of GENBANK® Accession No. AC197469.3; nucleotides 181778-182591 of GENBANK® Accession No. AC210263.4; nucleotides 120187-121112 of GENBANK® Accession No. AC203332.3; nucleotides 85472-86260 of GENBANK® Accession No. AC198211.4; nucleotides 147402-148055 of GENBANK® Accession No. AC191759.3; nucleotides 166218-166660 of GENBANK® Accession No. AC204581.3; and nucleotides 100621-101358 of GENBANK® Accession No. AC212580.4; and (b) introgressing the allele of the yield locus associated with the pre-selected yield trait into *Zea mays* germplasm that lacks the allele.

A method for introgressing an allele associated with a pre-selected yield trait into *Zea mays* germplasm, the method comprising (a) selecting from a population of *Zea mays* plants at least one *Zea mays* plant comprising at least one allele associated with a pre-selected yield trait, wherein the allele comprises a nucleotide sequence selected from the group including, but not limited to, SEQ ID NOs: 67-110; and (b) introgressing the allele associated with the pre-selected yield trait into *Zea mays* germplasm that lacks the allele.

A method for introgressing an allele associated with a pre-selected yield trait into *Zea mays* germplasm, the method comprising (a) selecting from a population of *Zea mays* plants at least one *Zea mays* plant that comprises an allele of a yield locus associated with a pre-selected yield trait, wherein the yield locus is selected from the group including, but not limited to, MTL1-18, MTPL1-10, MTSL1-6, and MTOL1-3, and further wherein: (1) MTL1, MTPL1, and MTSL1 map to *Zea mays* chromosome 5 and comprise a nucleotide sequence at least 85% identical to SEQ ID NO: 1; (2) MTL2 and MTSL2 map to *Zea mays* chromosome 5 and comprise a nucleotide sequence at least 85% identical to SEQ ID NO: 4; (3) MTL3 and MTSL3 map to *Zea mays* chromosome 5 and comprise a nucleotide sequence at least 85% identical to SEQ ID NO: 7; (4) MTL4, MTPL2, and MTSL4 map to *Zea mays* chromosome 3 and comprise a nucleotide sequence at least 85% identical to SEQ ID NO: 10; (5) MTL5 maps to *Zea mays* chromosome 2 and comprises a nucleotide sequence at least 85% identical to SEQ ID NO: 13; (6) MTL6 maps to *Zea mays* chromosome 5 and comprises a nucleotide sequence at least 85% identical to SEQ ID NO: 16; (7) MTL7 and MTPL3 map to *Zea mays* chromosome 7 and comprise a nucleotide sequence at least 85% identical to SEQ ID NO: 19; (8) MTL8 and MTPL4 map to *Zea mays* chromosome 5 and comprise a nucleotide sequence at least 85% identical to SEQ ID NO: 22; (9) MTL9 maps to *Zea mays* chromosome 7 and comprises a nucleotide sequence at least 85% identical to SEQ ID NO: 25; (10) MTL10 and MTOL3 map to *Zea mays* chromosome 1 and comprise a nucleotide sequence at least 85% identical to SEQ ID NO: 28; (11) MTL11 maps to *Zea mays* chromosome 2 and comprises a nucleotide sequence at least 85% identical to SEQ ID NO: 31; (12) MTL12 maps to *Zea mays* chromosome 10 and comprises a nucleotide sequence at least 85% identical to SEQ ID NO: 34; (13) MTL13 and MTSL5 map to *Zea mays* chromosome 8 and comprise a nucleotide sequence at least 85% identical to SEQ ID NO: 37; (14) MTL14 and MTPL9 map to *Zea mays* chromosome 1 and comprise a nucleotide sequence at least 85% identical to SEQ ID NO: 40; (15) MTL15 maps to *Zea mays* chromosome 5 and comprises a nucleotide sequence at least 85% identical to SEQ ID NO: 43; (16) MTL16 maps to *Zea mays* chromosome 1 and comprises a nucleotide sequence at least 85% identical to SEQ ID NO: 46; (17) MTL17 and MTPL8 map to *Zea mays* chromosome 5 and comprise a nucleotide sequence at least 85% identical to SEQ ID NO: 49; (18) MTL18 and MTPL7 map to *Zea mays* chromosome 10 and comprise a nucleotide sequence at least 85% identical to SEQ ID NO: 52; (19) MTOL1 maps to *Zea mays* chromosome 1 and comprises a nucleotide sequence at least 85% identical to SEQ ID NO: 55; (20) MTPL5 maps to *Zea mays* chromosome 4 and comprises a nucleotide sequence at least 85% identical to SEQ ID NO: 58; (21) MTSL6 and MTPL10 map to *Zea mays* chromosome 6 and comprises a nucleotide sequence at least 85% identical to SEQ ID NO: 61; and (22) MTPL6 and MTOL2 map to *Zea mays* chromosome 7 and comprise a nucleotide sequence at least 85% identical to SEQ ID NO: 64; and (b) introgressing the allele of the yield locus into *Zea mays* germplasm that lacks the allele, whereby an allele associated with a pre-selected yield trait is introgressed into *Zea mays* germplasm. In some embodiments, the percent identity is over at least 25, 50, 75, or 100 nucleotides of the indicated SEQ ID NO. In some embodiments, the percent identity is over the full length of the indicated SEQ ID NO. In some embodiments, the percent identity excludes consideration of any position at which the indicated SEQ ID NO. includes an "n" nucleotide from the percent identity calculation.

IV. Production of Improved Trait Carrying Maize Plants by Transgenic Methods

The use of SNPs as defined or trait-conferring parts, for producing a trait carrying maize plant, which by introducing a nucleic acid sequence comprising the trait-associated allele of the SNP into a recipient plant.

A donor plant, with the nucleic acid sequence that comprises a yield/ethanol production trait allele can be transferred to the recipient plant lacking the allele. The nucleic acid sequence can be transferred by crossing an yield/ethanol production trait carrying donor plant with a non-trait carrying recipient plant (i.e., by introgression), by transformation, by protoplast transformation or fusion, by a doubled haploid technique, by embryo rescue, or by any other nucleic acid transfer system. Then if desired optionally of progeny plants comprising one or more of the presently disclosed yield/ethanol production trait alleles can be selected. A nucleic acid sequence comprising an yield/ethanol production trait allele can be isolated from the donor plant using methods known in the art, and the this isolated nucleic acid sequence can transform the recipient plant by transgenic methods. This can occur with a vector, in a gamete, or other suitable transfer element, such as a ballistic particle coated with the nucleic acid sequence.

Plant transformation generally involves the construction of an expression vector that will function in plant cells and includes nucleic acid sequence that comprises an allele associated with the yield/ethanol production trait, which vector can comprise a yield/ethanol production trait-conferring gene. This gene usually is controlled or operatively linked to one or more regulatory element, such as a promoter. The expression vector can contain one or more such operably linked gene/regulatory element combinations, provided that at least one of the genes contained in the combinations encodes yield/ethanol production trait. The vector(s) can be in the form of a plasmid, and can be used, alone or in combination with other plasmids, to provide transgenic plants that are better yield/ethanol production plants, using transformation methods known in the art, such as the *Agrobacterium* transformation system.

Transformed cells often contain a marker allow transformation identification. The marker is adapted to be recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent that can be an antibiotic or a herbicide, or genes that encode an altered target which is insensitive to the inhibitor. Several positive selection methods are known in the art, such as mannose selection. Alternatively, marker-less transformation can be used to obtain plants without the aforementioned marker genes, the techniques for which are also known in the art.

V. Improved Plants, and Plant Parts, Seeds, Tissue Cultures, and Biomass Derived Therefrom The presently disclosed subject matter also provides improved maize plants, parts, seeds, progeny, and tissue cultures produced by any of the presently disclosed methods.

In some embodiments, the presently disclosed subject matter provides improved maize plants or a part, seed, progeny, and/or tissue culture thereof, which evidences a selected yield trait (e.g., a starch, protein, oil, and/or ethanol production trait), a genome homozygous with respect to one or more genetic alleles which are present in a first parent and not present in a second parent of the improved maize plant, in some embodiments, (a) the second parent evidences a more improved yield trait (e.g., a more improved starch, protein, oil, and/or ethanol production trait) than the first parent; and (b) the improved plant comprises one or more alleles from the first parent that evidence an improved yield trait in hybrid combination in at least one locus selected from (i) a starch locus with a desired starch allele; (ii) a protein locus with a desired protein allele; (iii) a digestibility locus with a desired ethanol production allele; and/or (iv) an oil locus with a desired oil allele; and the desired trait is not significantly less than that of the first parent in the same hybrid combination and yield characteristics which are not significantly different than those of the second parent in the same hybrid combination.

In some embodiments, the improved maize plants comprise each of a starch locus and a digestibility locus, and have improved yield trait when compared to a substantially identical maize plant not comprising the loci. In some embodiments, the improved maize plants comprise each of a starch locus with an allele for increased starch and a protein locus with an allele for decreased protein, and which have improved yield traits when compared to a substantially identical maize plant not comprising the loci.

In some embodiments, the improved maize plants, or parts, seeds, progeny, and tissue cultures thereof, comprise progeny of a cross between first and second inbred or hybrid lines, wherein one or more alleles conferring selected yield traits (e.g., starch, protein, oil, and/or ethanol production traits) are present in a homozygous state in the genome of one or the other or both of the first and second inbred or hybrid lines, such that the genome of the first and second inbreds or hybrids together donate to the improved maize plant or part thereof a complement of alleles sufficient to confer the improved yield trait(s). The presently disclosed subject matter also provides hybrids, or a part thereof, formed with the presently disclosed improved maize plants.

The presently disclosed subject matter also provides maize plants, or parts, seeds, and tissue cultures thereof, formed by selfing the presently disclosed improved yield traited hybrid(s).

The presently disclosed subject matter also provides maize plants, or parts, seeds, progeny, and tissue cultures thereof, that have one or more desired yield traits produced by the presently disclosed methods. In some embodiments, the maize plants that have one or more improved yield traits are hybrid maize. The presently disclosed subject matter also provides biomass and seed produced by the presently disclosed maize plants.

As such, the presently disclosed subject matter provides improved maize plants, or parts, seeds, progeny, tissue cultures, and biomass derived thereof, which evidence a selected yield trait, optionally wherein the genome of the improved maize plant, or the part, seed, progeny, or tissue culture thereof is homozygous with respect to one or more genetic alleles associated with the selected trait.

In some embodiments, the improved maize plant, or the part, seed, progeny, or tissue culture thereof comprises a genome that is homozygous with respect to one or more genetic alleles that are present in a first parent and not present in a second parent of the improved maize plant. In some embodiments, the second parent evidences more improved yield traits than the first parent, and the improved plant comprises one or more alleles from the first parent that evidence improved yield traits in hybrid combination in at least one locus selected from, but not limited to, a starch locus with a desired starch allele, a protein locus with a desired protein allele, a digestibility locus with a desired protein allele, and/or an oil locus with a desired oil allele, and the desired trait is not significantly less than that of the first parent in the same hybrid combination and yield characteristics which are not significantly different than those of the second parent in the same hybrid combination.

In some embodiments, the improved maize plants comprise each of a starch locus and a digestibility (i.e., ethanol production) locus, and have improved yield traits when compared to a substantially identical maize plant not comprising the starch locus and the digestibility locus. In some embodiments, the improved maize plants comprise each of a starch locus with an allele for increased starch and a protein locus with an allele for decreased protein, and which have improved yield traits when compared to a substantially identical maize plant not comprising the starch locus and the protein locus.

In some embodiments, the improved maize plants or parts thereof comprise progeny of a cross between first and second inbred or hybrid lines, wherein one or more alleles conferring selected yield traits are present in a homozygous state in the genome of one or the other or both of the first and second inbred or hybrid lines, such that the genome of the first and second inbreds or hybrids together donate to the improved maize plant or part thereof a complement of alleles sufficient to confer the improved yield trait(s). The presently disclosed subject matter also provides hybrids, or a part thereof, formed with the presently disclosed improved maize plants.

The presently disclosed subject matter also provides maize plants, or a part thereof, formed by selfing the presently disclosed improved yield traited hybrids.

The presently disclosed subject matter also provides maize plants that have desired yield traits occurring in maize produced by the presently disclosed methods.

In some embodiments, the maize plants that have improved yield traits are hybrid maize. The presently disclosed subject matter also provides biomass and seed produced by the presently disclosed maize plants.

The presently disclosed subject matter also provides Zea mays plants having one or more improved yield traits associated with the presence of MTL1-18, MTPL 1-9, MTSL 1-6, and/or MTOL 1-3 as defined herein in a homozygous genetic background.

The presently disclosed subject matter also provides maize plants that have one or more yield traits, wherein the plant is a plant of the species Zea mays, and the plant comprises at least one chromosomal region that confers enhanced or decreased ethanol production traits from the chromosome group comprising chromosomes 1, 2, 3, 5, 7, 8 and 10 and further wherein the at least one chromosomal region that confers an increase or decrease in ethanol production which is linked to at least one marker selected from markers associated with one of MTL1-18.

The presently disclosed subject matter also provides maize plants that have one or more yield traits, wherein the plant is a plant of the species Zea mays, and the plant comprises at least one chromosomal region that confers decreased or increased protein production traits from the chromosome group comprising chromosomes 1, 3, 5, 7, and 10 and further wherein the at least one chromosomal region that confers an increase or decrease in protein production which is linked to at least one marker selected from markers associated with one of MTPL1-10.

The presently disclosed subject matter also provides maize plants that have one or more yield traits, wherein the plant is a plant of the species Zea mays, and the plant comprises at least one chromosomal region that confers enhanced or decreased starch traits from the chromosome group comprising chromosomes 3, 5, 6, 8, and further wherein the at least one chromosomal region that confers an increase or decrease in starch which is linked to at least one marker selected from markers associated with one of MTSL1-6.

The presently disclosed subject matter also provides maize plants that have one or more yield traits, wherein the plant is a plant of the species Zea mays, and the plant comprises at least one chromosomal region that confers enhanced or decreased oil traits from the chromosome group comprising chromosomes 1 and 7, and further wherein the at least one chromosomal region that confers an increase or decrease in oil which is linked to at least one marker selected from markers associated with one of MTOL1-3.

The presently disclosed subject matter also provides parts of the plants defined herein. In some embodiments, the plant part is pollen, ovule, leaf, embryo, root, root tip, anther, flower, fruit, stem, shoot, seed; cell, rootstock, protoplast, or callus.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Initial Plant Materials—Platform and Panel

PLATFORM DEVELOPMENT. A group of 2998 temperate, tropical, and subtropical corn inbreds were selected from substantially homozygous corn inbred material. This group was reduced to 2075 inbreds by elimination of genetically modified corn, and low seed availability of certain corn seed. This was referred to as the inbred "platform". This platform was used for association marker work and phenotypic evaluation.

PANEL DEVELOPMENT. The platform group of corn inbred material was analyzed and further selected based on flowering data and further grouped by growing degree units (GDU). 1201 lines were characterized by growing degree units and grouped as follows.

A (1270-1390)=279 Lines
B (1391-1510)=700 Lines
C (1511-1630)=222 Lines
Total=1201 Lines The 1201 lines were then filtered for allelic diversity with markers. The results eliminated the very related lines (e.g., Neis similarity greater than or equal to 0.9 were eliminated). The diverse group resulted in the selection of an inbred panel of 600 lines categorized into their flower data based growing degree unit groups.

A (1270-1390)=180 Lines
B (1391-1510)=243 Lines
C (1511-1630)=177 Lines
Total=600 Lines The inbred panel and inbred platform were used for assaying association markers and for phenotypic evaluation.

Example 2

Phenotypic Data

The inbred platform and the inbred panel were each evaluated for eight phenotypic traits: moisture, density, oil, starch, protein, and digestibility (i.e., ethanol production) at 24, 48, and 72 hours as shown in Table 4. Moisture was the grain moisture after air drying. Density was recorded as a measure of kernel density. Oil, protein, and starch were each measured by well known methods in the industry and were recorded as a percentage.

Phenotypic information for inbred lines (1765 entries) was determined. The phenotypic information for certain traits corresponded to a calibration of the Near Infrared Spectroscope (NIR) machine. The NIR provided information on the yield traits starch, protein, oil, moisture, and density. Later, phenotypic information also included NIR phenotypic data for ethanol production traits (e.g., digestibility 24, digestibility 48, and digestibility 72). The phenotypic information of those lines that were part of the inbred platform (1732 inbreds) was extracted for the analysis. The results are shown in Tables 5 and 6.

TABLE 4

Traits and Trait Definitions

| Trait | SPIRIT Trait Code | SPIRIT Trait Definition |
|---|---|---|
| Moisture | GMADP | Grain moisture after air drying |
| Oil | OIL_P | Oil % |
| Density | DEN_N | Kernel density |
| Starch | STC_P | Grain starch content % |
| Protein | PRTNP | Protein % |
| Digestibility 24 | DG24P | Dry grind ethanol % after 24 hours fermentation |
| Digestibility 48 | DG48P | Dry grind ethanol % after 48 hours fermentation |
| Digestibility 72 | DG72P | Dry grind ethanol % after 72 hours fermentation |

TABLE 5

Inbred Platform (1753 Lines Phenotyped)

| Trait | Mean | Std Dev | Mean Std Err | Min | Max | N |
|---|---|---|---|---|---|---|
| Moisture | 10.64 | 0.69 | 0.02 | 9.04 | 15.81 | 1753 |
| Oil | 3.93 | 0.63 | 0.02 | 2.36 | 6.87 | 1753 |
| Density | 1.47 | 0.04 | 0.00 | 1.34 | 1.61 | 1753 |
| Starch | 70.01 | 2.35 | 0.06 | 59.87 | 78.01 | 1732 |
| Protein | 12.46 | 1.46 | 0.04 | 8.04 | 17.75 | 1728 |
| DG24P | 5.01 | 0.91 | 0.02 | 1.83 | 8.21 | 1732 |
| DG48P | 6.33 | 1.09 | 0.03 | 1.45 | 10.36 | 1732 |
| DG72P | 7.86 | 1.02 | 0.02 | 2.49 | 11.56 | 1732 |

TABLE 6

Inbred Panel (576 Lines Phenotyped)

| Trait | Mean | Std Dev | Mean Std Err | Min | Max | N |
|---|---|---|---|---|---|---|
| Moisture | 10.67 | 0.68 | 0.03 | 9.04 | 15.26 | 569 |
| Oil | 3.91 | 0.60 | 0.03 | 2.58 | 6.10 | 569 |
| Density | 1.47 | 0.04 | 0.00 | 1.35 | 1.61 | 569 |
| Starch | 70.09 | 2.40 | 0.10 | 62.14 | 78.01 | 576 |
| Protein | 12.41 | 1.46 | 0.06 | 8.04 | 16.71 | 574 |
| DGST 24 | 5.05 | 0.93 | 0.04 | 1.83 | 8.21 | 576 |
| DGST 48 | 6.39 | 1.07 | 0.04 | 3.42 | 9.67 | 576 |
| DGST 72 | 7.93 | 0.99 | 0.04 | 4.22 | 11.56 | 576 |

A scatter plot correlation of the yield associated traits from the inbred platform is shown in FIG. 1.

Example 3

Association Mapping of Platform and Panel

The inbred platform and inbred panel were characterized by substantial allelic diversity for the assayed traits. This variability or diversity was employed in the associated mapping experiments. The associated mapping used polymorphic SNP markers and controlled the population structure of these sets of inbreds. The platform contained at least 5 maize heteroic patterns including stiff stalk, non-stiff stalk, iodent, and mixtures of heteroic patterns. An inbred platform of 1732 lines and an inbred panel of 600 of these same lines were used to identify significant marker trait associations for traits of interest for yield.

The inbred panel and the inbred platform were phenotyped for traits of interest. Linear models were applied to identify marker trait associations (MTAs) for eight traits (starch, protein, moisture, density, oil, digestibility 24, digestibility 48, and digestibility 72) and 1654 SNP markers. Principal Components were included as covariates in the models to reduce the false positive rates and increase the coefficient of determination ($R^2$) of the models by including the most explicative variables into the model. A total of 122 MTAs were significant in General Linear Models (GLM) at an experiment-wise significance level of 5%. All the 122 were also significant (p-value <0.05) in Mixed Linear Models (MLM) that included Kinship estimates as the additive relationship matrix to further dissect the genetic relatedness among the inbred lines. Nine of these associations were common to more than one trait and their allelic effects on the traits were as expected (e.g., positive correlation between the traits starch and ethanol production and negative correlation between the traits protein and starch).

Genotypic Data

TAQMAN® SNPs.

Genotypic information was extracted for 2052 inbred lines that were included in the association platform list. A total of 496 SNPs were used for association and population structure analysis.

Illumina SNPs.

The Illumina Plex1 (version 1) was composed of 1536 SNPs. For the inbred panel, 559 lines were submitted for genotyping from which data was received for 485 lines (Table 7).

TABLE 7

Summary of Illumina PLEX1 Genotyping Results

| Inbred Panel | # Lines Panel | Submitted to PLEX 1 | Data from PLEX1 | % |
|---|---|---|---|---|
| Inbred | 600 | 559 | 485 | 80.83% |
| SS | 599 | 566 | 516 | 86.14% |
| NSS | 600 | 583 | 529 | 88.17% |
| Total | 1228 | 1174 | 1068 | 86.97% |

Linear models were applied to identify marker trait associations (MTAs) for these traits and 1654 SNP markers.

Genotypic data from the Plex1 was converted to a matrix form and raw data from 1219 SNP was analyzed using PowerMarker software (Liu & Muse, 2005) and 61 monomorphic markers were removed.

Kinship Analysis

Kinship analysis was initially done using genotypic data of 496 TAQMAN® SNP assays. Four different approaches for the estimation of Kinship (or co-ancestry coefficients) were compared: Kinship as the proportion of shared alleles, Kinship according to J. Nason (described in Loiselle et al., 1995; calculated in SPAGeDi; Hardy & Vekemans, 2002), Kinship according to Ritland (1996; calculated in SPA-GeDi), and Kinship as calculated in TASSEL 2.0.1. All pairwise comparisons were highly significant (p<0.0001). Proportion of shared alleles was employed. It has been suggested that the robustness in the estimation of Kinship can be affected by the number of markers. In order to test how different the Kinship matrices might be with different sets of markers, Kinship (pShared) was calculated with the 1158 SNPs of the Illumina Plex1. The K matrix obtained with the Plex1 SNPs was used in the mixed models for the inbred panel (see Table 8).

TABLE 8

Mantel Test Comparison of Kinship Matrices Calculated with 496 TAQMAN ® SNPs and 1158 PLEX1 SNPs

| Distance A | Distance B | Correlation | p Value |
|---|---|---|---|
| K matrix (Kpshared) 496 TAQMAN ® SNPs | K matrix (Kpshared) 1158 ILLUMINA ® SNPs | 0.8750 | 0.0000 |

PCA Analysis

Principal Component Analysis (PCA) or "eigenanalysis" has been proposed as an alternative to Structure software (Pritchard et al., 2000) for inferring population structure from genotypic data (Patterson et al., 2006). PCA has some advantages over Structure such as the processing speed for large datasets and avoiding the need of selecting a specific number of sub-populations. PCA was performed using the software SMARTPCA that is part of Eigenstrat using data from the Illumina PLEX1.

Selection of PCs Based on Association with the Trait of Interest.

The utilization of Principal Components (PCs) as covariates in linear model-based association mapping has relied in the assumption that the first PC's are the best covariates because the explain most of the genetic variation found with the markers (Zhao et al., 2007). The correlation between PCs and the phenotype was dependent on the trait and sometimes large PCs did not explain much of the variation whereas minor PC's explained a considerable percentage of the variation for certain traits. Both GLM and MLM were employed to assess the significance of each of 50 PCs and to estimate the percentage of the variation explained by them.

TASSEL.

The java-based software TASSEL (Trait Analysis by aSSociation, Evolution and Linkage) incorporates linear models (both general and mixed) approaches to establish association between markers and phenotypes while controlling for population and family structure (Bradbury et al., 2007). Population structure (Q) and/or Kinship (K) estimates can be incorporated in the models to reduce the number of false positives. It is also possible to replace the Q (Structure) matrix by a PCA matrix (Eigenvalues; Price et al., 2006; Zhao et al., 2007).

Association Models in TASSEL.

The different models used in TASSEL are shown in the Table 9.

TABLE 9

Models used for association in TASSEL

| General Lineal Models | Mixed Lineal Models |
|---|---|
| 1) Phenotype = Marker + selectedPCs (Eigenvalues) | 2) Phenotype = Marker + K (pshared) + selectedPCs (Eigenvalues) |

Adjustments for Multiple Testing.

The GLM procedure in TASSEL included the option to perform permutations to find out the experiment-wise error rate that corrected for accumulation of false positives when doing multiple comparisons. A total of 1,000 permutations were used. The MLM procedure did not include correction for multiple testing. In addition, the software QVALUE (Storey, 2002) was used to calculate q-values to control for the false discovery rate (FDR). The q-values were similar to p-values since they gave each hypothesis test a measure of significance in terms of a certain error rate. The q-values were useful for assigning a measure of significance to each of many tests performed simultaneously.

Association Results in Inbred Platform.

Phenotypic data was available for 1732 lines out of the 2052 lines of the inbred platform with marker information in the TAQMAN® 496 SNP set. The use of Mixed Linear Models (MLMs) to detect marker trait associations in data sets of considerable size (>1000) was limited by the computation time required to analyze the Kinship component of the model (i.e., it takes TASSEL 2.0.1 240 computing hours to finalize a K+Q model for one trait with 1732 lines and 488 SNPs when running at a designated 1536 Mb of RAM in a Core2 Duo PC). As an alternative, refining the General Linear Models to correct for population structure as much as possible without the need of the Kinship matrix was attempted.

Comparison between several GL models showed that the selection of PCs based on trait significance helped to reduce the bias towards significance. The comparison also showed that the grouping in k=10 subpopulations according to STRUCTURE results gave skewed results towards significance.

The data from TASSEL 2.1 of the GLM for both the 496 TAQMAN® SNPs for the 8 traits and the LSmeans per locus was run. The selection of the significant PCs as covariates in the linear models helped to control the distribution of p-values (i.e. avoid large numbers of false positives). However, variation was observed between the different traits.

A total of 85 SNPs showed experiment-wise p-values of less than 0.05 in the GLM (Trait=marker+selected PCs) in the inbred platform. The traits with the highest number of significant marker trait associations (MTAs) were oil and protein with 13 and the one with least was moisture with 7. A total of 15 SNPs with significant p-values (experiment-wise p-value <5%) showed association with more than one trait (see Table 10). In most cases, the alleles that increased the level of protein decreased digestibility and/or starch (see e.g. the traits associated with SEQ ID NOs: 1, 4, 7, and 10).

TABLE 10

Loci with Experiment-Wise p-Values of Less than 0.05, Their Distribution among Traits, and the Effects of Reference Alleles on the Different Traits

| SEQ ID NO: | Pos | Allele 1 | Allele 2 | Effect of Allele 1 |
|---|---|---|---|---|
| 1 | 701 | A | G | Protein (−); Starch (+); DGST 48 (+); DGST 72 (+) |
| 4 | 498 | G | A | Starch (+); DGST 48 (+); DGST 72 (+) |
| 7 | 587 | T | C | Starch (+); DGST 48 (+); DGST 72 (+) |
| 10 | 708 | G | A | Protein (−); Starch (+); DGST 48 (+) |
| 13 | 140 | C | T | DGST 24 (+); DGST 48 (+) |
| 16 | 116 | A | G | DGST 24 (+); DGST 48 (+); DGST 72 (+) |
| 19 | 269 | A | G | Protein (−); DGST 24 (+) |
| 22 | 280 | A | G | Protein (−); DGST 48 (+) |
| 25 | 374 | T | G | Density (+); DGST 24 (−) |
| 28 | 236 | G | A | Oil (−); DGST 48 (+) |
| 31 | 605 | G | A | DGST 48 (+); DGST 72 (+) |
| 34 | 349 | C | T | Moisture (−); DGST 24 (+) |
| 37 | 389 | C | T | Starch (+), DGST 72 (+) |
| 40 | 66 | G | A | Protein (−), DGST 24 (+) |
| 43 | 278 | T | C | DGST 48 (+), DGST 72 (+) |
| 46 | 463 | G | A | Density (−), DGST 24 (+), DGST 48(+) |
| 49 | 510 | G | A | Protein (−), DGST 48 (+), DGST 72 (+) |
| 52 | 134 | G | T | Protein (−), DGST 48 (+), DGST 72 (+) |
| 55 | 367 | A | G | Moisture (−), Oil (−) |
| 58 | 119 | G | C | Density (−); Protein (−) |
| 61 | 347 | G | T | Starch(+), Protein (−) |
| 64 | 356 | A | G | Oil (+); Protein (−) |

(−): Allele 1 results in a lower level than Allele 2;
(+): Allele 1 results in a higher level than Allele 2.

With the exception of the SNPs at nucleotide position 140 of SEQ ID NO: 13 and nucleotide position 349 of SEQ ID NO: 34, the SNPs identified reflected single nucleotide differences that were limited to the stated positions. Thus, for example, the only difference between a favorable allele and an unfavorable allele (depending on the desired trait) for SEQ ID NO: 1 was whether the nucleotide at position 701 was an A or a G. It was noted, however, that SEQ ID NOs: 13 and 34 were more complex. Nucleotide position 140 of SEQ ID NO: 13, for example, is a C or a T, but review of the sequence surrounding this position in the various nucleic acid samples indicated that the C derived not from a nucleotide substitution but from a deletion. Specifically, in Allele 1 of Table 10 for SEQ ID NO: 13, the C was present at position 140 because one of the string of five Ts shown in positions 136-140 of SEQ ID NO: 13 was deleted, which moved the C that followed this string of Ts from position 141 in those embodiments of SEQ ID NO: 13 where five Ts were present to position 140 in those embodiments where only four Ts were present.

Similarly, the SNP that was found in SEQ ID NO: 34 also involved a deletion, in this case a three nucleotide deletion of the CGA sequence at positions 349-351 of SEQ ID NO: 34. Thus, Allele 1 of SEQ ID NO: 34 of Table 10 included the CGA trinucleotide, and thus had a C at position 349. Allele 2, on the other hand, had a deletion of the CGA trinucleotide, resulting in the T that is present at position 352 of SEQ ID NO: 4 being moved to position 349.

Association Results in Inbred Panel.

Phenotypic data was available for 576 out of the 600 lines that constituted the inbred panel. Information from a total of 1654 SNPs was available for the inbred panel. In addition to a larger number of SNP data, the reduced size of the inbred panel in comparison to the inbred platform allows to reduce the running time of the Mixed Linear Models.

The data was developed from TASSEL of the two models (GLM and MLM) selected for both the 496 TAQMAN® SNPs and the Illumina PLEX1, and the LSmeans per locus (from the GLM model). The selection of the significant PCs as covariates in the linear models helped to control the distribution of p-values (i.e. avoid large numbers of false positives). The inclusion of the Kinship matrix as the additive relationship matrix in the mixed model helped to reduce the false positive rate to expected levels and to increase the R2 of the models. Mean R2 values for the GLM and MLM (Trait=marker+selectedPCs+Kpshared) for the assayed traits are presented in Table 11.

TABLE 11

Mean R2 Values for the GLM and MLM for the Assayed Traits

| TRAIT | Mean R2 Model | |
|---|---|---|
| | GLM | MLM |
| Density | 0.15 | 0.20 |
| Moisture | 0.21 | 0.27 |
| Oil | 0.19 | 0.25 |
| Protein | 0.28 | 0.32 |
| Starch | 0.24 | 0.28 |
| Digestion 24 | 0.34 | 0.38 |
| Digestion 48 | 0.25 | 0.30 |
| Digestion 72 | 0.24 | 0.28 |

The correlation analysis between the p-values for the different traits suggested that there were significant correlations for several trait pairs. This correlation pattern followed the phenotypic correlations in which, for example, Starch and Protein were correlated with Digestibility at 24, 48, and 72 hours.

A total of nine SNPs with significant p-values (experiment-wise p-value <0.05) showed association with more than one trait (Table 12). For example, the loci that correspond to SEQ ID NOs: 49 and 52 showed association with Protein, Digestibility 24, and Digestibility 48. In both cases the allele that increases the level of protein decreases the yield of ethanol after both 48 and 72 hours of digestion. Only one MTA was common to Starch and Digestibility (SEQ ID NO: 37) for which, as expected, an increase in Starch represented an increase in ethanol production.

TABLE 12

Loci with Experiment-wise p-value < 0.05

| LOCUS | SNP Position | Allele 1 | Allele 2 | Effect of Allele 1 |
|---|---|---|---|---|
| MTL6 (SEQ ID NO: 16) | 116 | A | G | DGST 48 (+), DGST 72 (+) |
| MTL13/MTSL5 (SEQ ID NO: 37) | 389 | C | T | Starch (+), DGST 72 (+) |
| MTL14/MTPL9 (SEQ ID NO: 40) | 66 | G | A | Protein (−), DGST 24 (+) |
| MTL15 (SEQ ID NO: 43) | 278 | T | C | DGST 48 (+), DGST 72 (+) |
| MTL16 (SEQ ID NO: 46) | 463 | G | A | Density (−), DGST 24 (+), DGST 48(+) |
| MTL17/MTPL7 (SEQ ID NO: 49) | 510 | G | A | Protein (−), DGST 48(+), DGST 72(+) |
| MTL18/MTPL7 (SEQ ID NO: 52) | 134 | G | T | Protein (−), DGST 48(+), DGST 72(+) |
| MTOL1 (SEQ ID NO: 55) | 367 | A | G | Moisture (−), Oil (−) |
| MTSL6/MTPL10 (SEQ ID NO: 61) | 347 | G | T | Starch(+), Protein (−) |

By way of example, Table 12 indicates that MTL6, which is a locus that is associated with SEQ ID NO: 16 and that includes an SNP at position 116 of SEQ ID NO: 16. When the locus includes an A nucleotide at this position, digestibility (ethanol production) is increased at both 48 and 72 hours relative to when a G (or, for that matter, a C or T) is present at this position. Similarly, MTL15 is a locus associated with SEQ ID NO: 43 and that includes an SNP at position 278 of SEQ ID NO: 43. When the locus includes a T nucleotide at this position, digestibility (ethanol production) is increased at both 48 and 72 hours relative to when a C (or, for that matter, a G or T) is present at this position.

Additionally, MTL17/MTPL7 is a locus associated with SEQ ID NO: 49 and that includes an SNP at position 510 of SEQ ID NO: 49. When the locus includes a G nucleotide at this position, digestibility (ethanol production) is increased at both 48 and 72 hours and protein content is decreased relative to when an A (or, for that matter, a C or T) is present at this position.

Example 4

Running Assays to Select for Traits

Each of the lines was phenotyped for each of the traits. The assays using the primers to produce amplicons from which the probes could be employed to detect the allele that was present in each of these lines. The lines which had positive alleles for yield were selected and used in the next breeding generation. This marker associated selection was adapted to enhance the yield traits in the next generation of maize germplasm. The landraces and the families of these lines were different.

Figure 2:
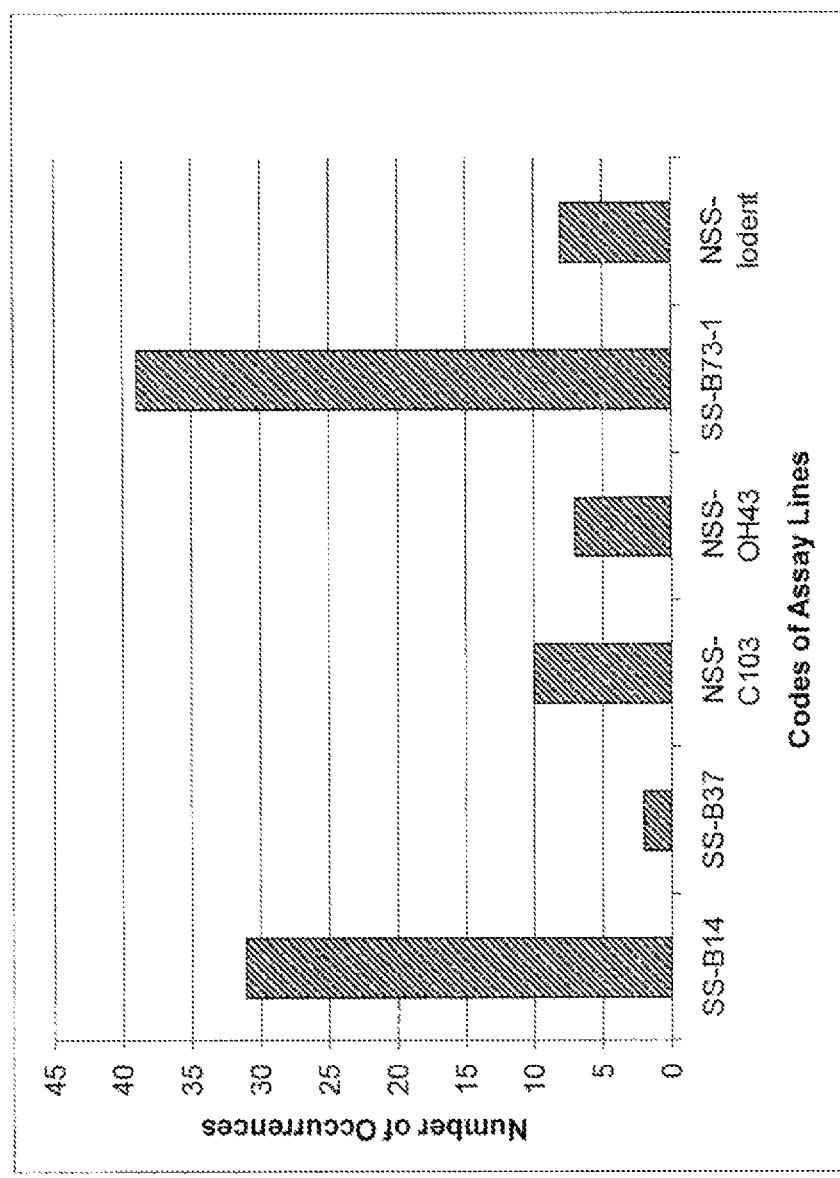
FIG. 2 is a bar graph showing a random sampling of 97 lines that were present in the inbred panel and the inbred platform described hereinbelow. For each bar, the number of occurrences represents the number of lines out of the 97 lines that had a genomic contribution that could be traced to the indicated line. SS: stiff stalk; NSS: non-stiff stalk.

The lines employed in the inbred panel and inbred platform disclosed herein represented considerable genetic diversity. A sampling of the lines in the inbred panel and the inbred platform is depicted in FIG. 2. From this sampling of the lines employed, it can be seen that various different heterotic groups were employed, demonstrating that the validations disclosed herein were performed over several different heterotic groups and/or germplasm pools.

Discussion of the Examples

Correlation of Results of Platform and Panel.

A platform of inbreds selected for diversity (approximately 1201 inbred lines) were analyzed and selected based on flowering data and grouped by growing degree units (GDU).

These lines were then filtered for allelic diversity with SNP genome wide sets of markers and related lines were identified and eliminated. A second group from the platform was selected based on being diverse. The selection resulted in an inbred panel of 600 lines, which then were also categorized into their flower data and grouped according to growing degree unit. The inbred platform and the inbred panel were subjected to phenotypic evaluation. The grain moisture, density, oil, protein, starch, and digestibility for ethanol at 24, 48 and 72 hours were taken and recorded. This phenotypic data was then correlated with the plants genotypic data based on SNPs to identity the marker trait associations with the listed traits.

Marker-assisted selection (MAS) of maize germplasm has become a common practice in breeding. The efficiency of MAS, however, depends on the accuracy in detection of markers closely linked to MTLs. Association mapping has been widely used as an alternative to linkage mapping in detecting MTLs. Association mapping takes advantage of recombination events accumulated over many generations, and thus offers potentially much higher mapping resolution than conventional linkage mapping, which is usually based on biparental crosses.

Effective association mapping in maize relies on the LD structure—sizes and distributions of LD blocks and LD strengths in the blocks on the genome. LD structure has two implications on association mapping: 1) it determines the feasibility of association mapping; 2) it determines the potential mapping resolution. This approach is based on linkage disequilibrium (LD) between linked loci. Because LD usually exists only in much narrower chromosomal regions, mapped MTLs are mapped with a higher resolution than linkage mapping. However, LD can occur between unlinked loci, which can be undesirable, and spurious LD can be caused by population structure, genotyping errors, etc. As a result, to reliably detect true LD between closed linked loci, sophisticated statistical approaches are needed to minimize false positives of various kinds.

TASSEL, developed by Buckler's lab at Cornell University (Bradbury et al. 2007), is one of the software packages that can achieve this goal. TASSEL is based on mixed linear model with population structure and genetic correlations being explicitly controlled in the models. This package was employed for association analysis with the data in these experiments.

The inbred platform and inbred panel had allelic diversity for the 8 traits. This variability or diversity was employed in the associated mapping experiments. The associated mapping used polymorphic SNP markers and controlled the population structure of these sets of inbreds. The platform contained at least 5 maize heteroic patterns including: stiff stalk, nonstiff stalk, iodent, and mixtures of heteroic patterns. An inbred platform of 1732 (~600 same as panel) lines/and an inbred panel of 600 of these same lines was used to identify significant marker trait associations for traits of interest for yield and ethanol. Linear Models identified the associations (MTLs) for eight traits with 1654 SNP markers. The models included Principal Components to reduce false positives. The MLM also included a Kinship estimate to account for genetic relatedness. The allelic effects on the traits were determined. These effects correlated with the phenotypic effects noted.

By comparing the results between the inbred panel and the inbred platform the significant 496 TAQMAN® SNPs in both data sets for the same trait or for highly correlated traits were identified.

The significant MTAs obtained in the current analysis should be considered as MTLs i.e. that they represent a region of the maize genome. A score system was adapted to rank the MTAs, the SNP assays and/or the SNP locus. This score system weighs the importance of the trait (40%), the significance in the other data set (30%) and the significance in multiple traits (30%). The total number of points that a MTA accumulate can be used to create priority lists.

Summary of Yield Associated Loci.

SNP assays were performed and contributions to variability were determined for the twenty-two loci represented by SEQ ID NOs: 1-173. The results are summarized as follows:

SEQ ID NO: 1: Two SNP assays were included in the analysis. In the inbred platform, the SNP assay was associated with the yield traits Protein (GLM p-adj=0.001), explaining 0.76% of the variation; Starch (GLM p-adj=0.001), explaining 0.53% of the variation; DGST 48 (GLM p-adj=0.005) explaining 0.47% of the variation; and DGST 72 (GLM p-adj=0.001), explaining 0.54% of the variation. In the inbred panel, the SNP assay was significantly associated with the trait DGST 48 (GLM p-adj=0.017; MLM p=0.013), explaining ~1.2% of the variation (R2=GLM 1.36%; MLM 1%). The SNP marker is located on chromosome 5 close to the loci associated with SEQ ID NOs: 16 and 49 (see below). There are NAM QTLs in this region of chromosome 5 for the yield traits Starch and Protein.

SEQ ID NOs: 4 and 7: Four SNP assays were included in the analysis. In the inbred platform, one SNP assay (located between SEQ ID NOs: 5 and 6) was significantly associated with the yield traits Starch (GLM p-adj=0.001), explaining 0.55% of the variation; DGST 48 (GLM p-adj=0.001), explaining 0.51% of the variation; and DGST 72 (GLM p-adj=0.005) explaining 0.41% of the variation. A second SNP assay (located between SEQ ID NOs: 8 and 9) was associated with the same traits: Starch (GLM p-adj=0.001), explaining 0.53% of the variation; DGST 48 (GLM p-adj=0.03), explaining 0.39% of the variation; and DGST 72 (GLM p-adj=0.001), explaining 0.57% of the variation. The SNP markers are located on chromosome 5. There is an overlapping NSS metaQTL for the yield trait Starch that explains an average of 1.2% of the variation observed for the trait.

SEQ ID NO: 10: Three SNP assays were included in the analysis. In the inbred platform, one SNP assay was significantly associated with the yield traits Protein (GLM p-adj=0.001), explaining 0.71% of the observed variation; Starch (GLM p-adj=0.001), explaining 0.54% of the observed variation; and DGST 48 (GLM p-adj=0.001), explaining 0.52% of the observed variation. The SNP is located on chromosome 3.

SEQ ID NO: 13: Four SNP assays were included in the analysis. In the inbred Platform, one SNP assay was statistically significant for the yield traits DGST 24 (GLM p-adj=9.9E-4), explaining 0.51% of the variation observed; and DGST 48 (GLM p-adj=0.048), explaining 0.37% of the variation observed. The SNP assay was also found to be statistically associated with the yield trait Starch in the Inbred Panel (GLM p-adj=0.013; MLM p=0.004), explaining ~1.35% of the variation observed (R2=GLM 1.43%; MLM 1.32%). The SNP is located on chromosome 2. There is a metaQTL for the trait DGST 72 located on chromosome 2.

SEQ ID NO: 16: Three SNP assays were included in the analysis. In the inbred platform, one SNP assay was statistically significant for the yield traits DGST 24 (GLM p-adj=0.034), explaining 0.37% of the variation observed; and DGST 48 (GLM p-adj=9.9E-4), explaining 0.54% of the variation observed. In the inbred panel, this same SNP assay was statistically significant for the yield traits DGST 48 (GLM p-adj=9.9E-4; MLM p=5.9E-4), explaining ~2% of the observed variation (R2=GLM 2.23%; MLM 1.91%); and DGST 72 (GLM p-adj=0.002; MLM p=0.0017), explaining ~1.7% of the observed variation (R2=GLM 1.77%; MLM 1.64%). The SNP is located on chromosome 5 close to the loci associated with SEQ ID NO: 1 and SEQ ID NO: 49 that are also significant for ethanol-related traits. There are NAM QTLs in this region of chromosome 5 for the yield traits Starch and Protein.

SEQ ID NO: 19: Four SNP assays were included in the analysis. In the inbred platform, one SNP assay was associated with the yield traits DGST 24 (GLM p-adj=0.019), explaining 0.4% of the observed variation; and Protein (GLM p-adj=0.043), explaining 0.41% of the observed variation. In the inbred panel, this SNP assay was statistically significant for the yield trait Oil (GLM p-adj=9.9E-4; MLM p=0.0016) explaining ~1.9% of the variation observed (R2=GLM 2.05; MLM 1.72). The SNP marker is located on chromosome 7 close to the locus associated with SEQ ID NO: 64 that was significantly associated with Protein and Oil.

SEQ ID NO: 22: Two SNP assays were included in the analysis. In the inbred platform, one SNP assay was significantly associated with the yield traits Protein (GLM p-adj=0.011), explaining 0.45% of the variation observed; and DGST 48 (GLM p-adj=0.025), explaining 0.37% of the variation. In the inbred panel, the SNP assay was also significantly associated with the yield trait DGST 48 (GLM p-adj=0.049; MLM p=0.017), explaining ~1% of the variation (R2=GLM 1.2%; MLM 0.9%). The SNP assay is located on chromosome 5.

SEQ ID NO: 25: Three SNP assays were included in the analysis. In the inbred platform the SNP assay was significantly associated with the yield trait DGST 24 (GLM p-adj=0.001) explained 0.62% of the variation observed. In the inbred panel, the SNP assay was significantly associated with the yield trait DGST 24 (MLM p=0.015), explaining 0.83% of the variation. The SNP assay is located on chromosome 7.

SEQ ID NO: 28: There were three SNP assays included in the analysis. In the inbred platform, one SNP assay was significantly associated with the yield traits DGST 48 (GLM p-adj=0.028), explaining 0.37% of the observed variation; and Oil (GLM p-adj=0.001), explaining 0.52% of the variation. The SNP is located on chromosome 1. There are two overlapping NSS metaQTLs for the yield traits Starch and DGST 72.

SEQ ID NO: 31: Three SNP assays were included in the analysis. In the inbred platform, one SNP assay was significantly associated with the yield traits DGST 48 (GLM p-adj=0.001), explaining 0.5% of the variation observed; and DGST 72 (GLM p-adj=0.022), explaining 0.4% of the variation. The SNP is located on chromosome 2.

SEQ ID NO: 34: Four SNP assays were included in the analysis. In the inbred platform, one SNP assay was significantly associated with the yield trait DGST 24: (GLM p-adj=0.001) explaining 0.6% of the variation observed. The SNP is located on chromosome 10. There is an overlapping NSS metaQTL for the yield trait Starch.

SEQ ID NO: 37: Four SNP assays were included in the analysis. In the inbred panel, one SNP assay was significantly associated with the yield traits Starch (GLM p-adj=0.007; MLM p=0.0025), explaining ~1.5% of the observed variation (R2=GLM 1.6%; MLM 1.5%); and DGST 72 (GLM p-adj=0.028; MLM p=0.0081), explaining ~1.2% of the variation (R2=GLM 1.2%; MLM 1.2%). The SNP is located on chromosome 8.

SEQ ID NO: 40: Five SNP assays were included in the analysis. In the inbred panel, one SNP was significantly associated with the yield traits DGST 24 (GLM p-adj=0.039; MLM p=0.019), explaining ~0.9% of the variation (R2=GLM 1%, MLM 0.8%); and Protein (GLM p-adj=0.004; MLM p=0.005), explaining ~1.3% of the observed variation (R2=GLM 1.4%; MLM 1.2%). The SNP marker is located on chromosome 1. There is an overlapping NSS metaMTL for the yield trait DGST 72.

SEQ ID NO: 43: There was one SNP assay included in the analysis. In the inbred panel, this SNP was significantly associated with the yield traits DGST 48 (GLM p-adj=0.007; MLM p=$3.4 \times 10^{-3}$), explaining ~1.5% of the observed variation (R2=GLM 1.6%; MLM 1.3%); and DGST 72 (GLM p-adj=0.024; MLM p=$4.3 \times 10^{-3}$), explaining ~1.3% of the variation (R2=GLM 1.4%; MLM 1.3%). The SNP is located on chromosome 5.

SEQ ID NO: 46: Four SNP assays were included in the analysis. In the inbred panel, one SNP assay was significantly associated with the yield traits DGST 24 (GLM p-adj=0.001; MLM p=$7.3 \times 10^{-4}$), explaining ~1.83% of the variation observed (R2=GLM 2.1%; MLM 1.6%); and DGST 48 (GLM p-adj=0.003; MLM p=$2.3 \times 10^{-3}$), explaining ~1.5% of the variation (R2=GLM 1.6%; MLM 1.5%). The SNP is located on chromosome 1. There is an overlapping NSS metaQTL for the trait DGST 72.

SEQ ID NO: 49: One SNP assay was included in the analysis. In the inbred panel, the SNP was significantly associated with the yield traits Protein (GLM p-adj=$9.9 \times 10^{-4}$; MLM p=$8.2 \times 10^{-4}$), explaining ~1.8% of the variation observed (R2=GLM 1.8; MLM 1.7); DGST 48 (GLM p-adj=$9.9 \times 10^{-4}$; MLM p=$1.2 \times 10^{-4}$), explaining ~2.4% of the variation (R2=GLM 2.5%; MLM 2.3%); and DGST 72 (GLM p-adj=$9.99 \times 10^{-4}$; GLM $3.8 \times 10^{-4}$), explaining ~2% of the variation (R2=GLM 2%, MLM 2%). The SNP marker is located on chromosome 5. This locus is in the vicinity of the loci associated with SEQ ID NOs: 16 and 1, also associated with ethanol-related traits. There are NAM QTLs in this region of chromosome 5 for the yield traits Starch and Protein.

SEQ ID NO: 52: One SNP assay was included in the analysis. In the inbred panel, the SNP was significantly associated with the yield traits Protein (GLM p-adj=$9.9 \times 10^{-4}$; MLM p=$2.8 \times 10^{-4}$), explaining ~2.1% of the variation (R2=GLM 2.2%; MLM 2%); DGST 48 (GLM p-adj=0.034; MLM p=$5.4 \times 10^{-4}$); explaining ~1.7% of the variation (R2=GLM 1.4%; MLM 1.9%), and DGST 72 (GLM p-adj=$9.9 \times 10^{-4}$; MLM p=$1 \times 10^{-5}$), explaining ~3.2% of the variation (R2=GLM 3.3%; MLM 3.1%). The SNP marker is located on chromosome 10. There is a NAM QTL in this region of chromosome 10 for the yield trait Starch.

SEQ ID NO: 55: In the inbred panel, the SNP was significantly associated with the yield trait Oil. The SNP marker is located on chromosome 1.

SEQ ID NO: 58: Two SNP assays were included in the analysis. In the inbred platform, one SNP assay was significantly associated with the yield trait Protein: (GLM p-adj=0.017) explaining 0.5% of the observed variation. The SNP is located on chromosome 4 (position 69.52 cM).

SEQ ID NO: 61: Two SNP assays were included in the analysis. In the inbred panel, one SNP assay was significantly associated with the yield traits Protein (GLM p-adj=0.028; MLM p=0.017), explaining ~1% of the variation observed (R2=GLM 1.2% MLM 0.9%); and Starch (GLM p-adj=0.002; MLM p=0.0037), explaining ~1.6% of the variation (R2=GLM 1.7%; MLM 1.4%). The SNP is located on chromosome 6.

SEQ ID NO: 64: Two SNPs were included in the analysis. In the inbred panel, one SNP assay was significantly associated with the yield traits Protein (GLM p-adj=0.01), explaining 0.5% of the variation observed; and Oil (GLM p-adj=0.034), explaining 0.4% of the variation. The SNP is located on chromosome 7. This locus is close to the locus associated with SEQ ID NO: 19 that was significantly associated with the yield traits Protein, DGST 24, and Oil.

The SNPs disclosed herein were consistent in the General Linear Models (GLM) and in the Mixed Linear Models (MLM) discussed hereinabove. As such, the presently disclosed subject matter provides evidence that these SNPs, and markers comprising the same, can be employed for introgression of yield traits from and into various *Zea mays* genetic backgrounds.

REFERENCES

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Altschul et al. (1990) Basic local alignment search tool. *J Mol Biol* 215:403-410.

Altschul et al. (1997) Gapped BLAST and PSI-BLAST: a new generation of protein database search programs. *Nucleic Acids Res* 25:3389-3402.

Ausubel et al. (eds.) (1999) *Short Protocols in Molecular Biology* Wiley, New York, N.Y., United States of America.

Bradbury et al. (2007) TASSEL: software for association mapping of complex traits in diverse samples. *Bioinformatics* 23:2633-2635.

Fan et al. (2006) Highly parallel genomic assays. *Nature Reviews. Genetics* 7:632-644.

Glick & Thompson (1993) *Methods in Plant Molecular Biology and Biotechnology*, CRC Press, Boca Raton. Fla., United States of America.

Hardy & Vekemans (2002) SPAGeDi: a versatile computer program to analyse spatial genetic structure at the individual or population levels. *Molecular Ecology Notes* 2:618-620.

Liu & Muse (2005) PowerMarker: an integrated analysis environment for genetic marker analysis. *Bioinformatics* 21:2128-2129.

Loiselle et al. (2005) Spatial genetic structure of a tropical understory shrub, *Psychotria officinalis* (Rubiaceae). *American Journal of Botany* 82:1420-1425.

Paterson (1996) in Paterson (ed.) *Genome Mapping in Plants*. R. G. Landes Company, Georgetown, Tex., United States of America, pages 41-54.

Patterson et al. (2006) Population Structure and Eigenanalysis. *PLoS Genetics* 2:e190.

Perin et al. (2002) A reference map of *Cucumis melo* based on two recombinant inbred line populations. *Theor Appl Genet.* 104:1017-1034.

Price et al. (2006) Principal components analysis corrects for stratification in genome-wide association studies. *Nature Genetics* 38:904-909.

Pritchard et al. (2000) Inference of Population Structure Using Multilocus Genotype Data. *Genetics* 155:945-959.

Ritland (1996) Estimators for pairwise relatedness and individual inbreeding coefficients. *Genetics Research* 67:175-186.

Sambrook & Russell (2001). *Molecular Cloning: A Laboratory Manual., Third Edition*, Cold Spring Harbor Laboratory Press, Cold Spring Harbor, N.Y., United States of America.

Storey (2002) A direct approach to false discovery rates. *Journal of the Royal Statistical Society: Series B* 64:479-498.

Tijssen (1993) in *Laboratory Techniques in Biochemistry and Molecular Biology*, Elsevier, New York, N.Y., United States of America.

U.S. Pat. No. 4,458,068.

Zhao et al. (2007) An *Arabidopsis* Example of Association Mapping in Structured Samples. *PLoS Genetics* 3:e4.

Zietkiewicz et al. (1994) Genome fingerprinting by simple sequence repeat (SSR)-anchored polymerase chain reaction amplification. *Genomics* 20:176-183.

It will be understood that various details of the presently disclosed subject matter may be changed without departing from the scope of the presently disclosed subject matter. Furthermore, the foregoing description is for the purpose of illustration only, and not for the purpose of limitation.

---

What is claimed is:

1. A method of producing a maize plant having improved digestibility, the method comprising the steps of:
   (a) isolating at least one nucleic acid from a population of maize plants;
   (b) genotyping said nucleic acid for the presence of a marker located within a chromosomal interval, wherein said chromosome interval is defined by and comprises SEQ ID NO: 16 and, wherein said chromosome interval further comprises an A allele corresponding to position 116 of SEQ ID NO: 16;
   (c) selecting a first maize plant on the basis of the presence of the marker detected in (b);
   (d) crossing the first maize plant of (c) with a second maize plant not having said chromosome interval;
   (e) collecting seed from the cross of (d); and
   (f) growing a progeny maize plant from the seed of (e), wherein said progeny maize plant comprises in its genome said chromosome interval, thereby producing a plant with improved digestibility.

2. The method of claim 1, wherein the maize progeny plant of (f) is a hybrid maize plant.

3. The method of claim 1, wherein the first or second maize plant is a inbred.

4. The method of claim 1, wherein the chromosome interval is located on *Zea mays* chromosome 5.

5. The method of claim 1, wherein the progeny maize plant is an elite maize plant.

6. The method of claim 1, wherein the maize progeny plant displays improved digestibility at any one of 24 hours, 48 hours or 72 hours as compared to a control plant.

7. The method of claim 1, wherein the chromosome interval is detected through the use of a PCR primer pair that anneals to any one of SEQ ID NOs: 16 or 116, wherein the primer pair is capable of initiating DNA polymerization by a DNA polymerase on a *Zea mays* nucleic acid template to generate a amplicon diagnostic for the presence of said chromosome interval.

8. The method of claim 7, wherein the PCR primer pair comprises SEQ ID NOS: 17 and 18.

9. The method of claim 1, wherein the maize progeny plant further comprises at least one other locus in its genome selected from the group consisting of MTL1, MTL2, MTL3, MTL4, MTL5, MTL7, MTL8, MTL9, MTL10, MTL11, MTL12, MTL13, MTL14, MTL15, MTL16, MTL17; and MTL18.

* * * * *